(12) United States Patent
Rossello et al.

(10) Patent No.: US 9,480,758 B2
(45) Date of Patent: *Nov. 1, 2016

(54) DIAGNOSTIC AGENTS SELECTIVE AGAINST METALLOPROTEASES

(75) Inventors: Armando Rossello, Pisa (IT); Elisa Nuti, Pisa (IT); Stanislava Ivanova Avramova, Pisa (IT); Fulvio Uggeri, Colleretto Giacosa (IT); Alessandro Maiocchi, Colleretto Giacosa (IT)

(73) Assignee: BRACCO IMAGING S.P.A., Milan (IT)

( * ) Notice: Subject to any disclaimer, the term of this patent is extended or adjusted under 35 U.S.C. 154(b) by 323 days.

This patent is subject to a terminal disclaimer.

(21) Appl. No.: 13/000,794

(22) PCT Filed: Jul. 21, 2009

(86) PCT No.: PCT/EP2009/059338
§ 371 (c)(1),
(2), (4) Date: Dec. 22, 2010

(87) PCT Pub. No.: WO2010/010079
PCT Pub. Date: Jan. 28, 2010

(65) Prior Publication Data
US 2011/0117015 A1    May 19, 2011

(30) Foreign Application Priority Data
Jul. 22, 2008  (EP) .................................... 08160856

(51) Int. Cl.
| | | |
|---|---|---|
| A61K 51/00 | (2006.01) |
| A61M 36/14 | (2006.01) |
| A61K 49/00 | (2006.01) |
| A61K 49/08 | (2006.01) |
| A61K 49/10 | (2006.01) |
| A61K 49/22 | (2006.01) |
| A61K 51/04 | (2006.01) |

(52) U.S. Cl.
CPC ......... A61K 49/0017 (2013.01); A61K 49/085 (2013.01); A61K 49/10 (2013.01); A61K 49/101 (2013.01); A61K 49/103 (2013.01); A61K 49/105 (2013.01); A61K 49/106 (2013.01); A61K 49/221 (2013.01); A61K 51/0497 (2013.01)

(58) Field of Classification Search
CPC ........... A61K 49/0017; A61K 49/085; A61K 49/10; A61K 49/101; A61K 49/103; A61K 49/105; A61K 49/106; A61K 49/221; A61K 51/0497
USPC ...................................................... 424/1.11
See application file for complete search history.

(56) References Cited

U.S. PATENT DOCUMENTS

| | | |
|---|---|---|
| 4,093,709 A | 6/1978 | Choi et al. |
| 4,131,648 A | 12/1978 | Choi et al. |
| 4,138,344 A | 2/1979 | Choi et al. |
| 4,180,646 A | 12/1979 | Choi et al. |
| 5,021,556 A | 6/1991 | Srinivasan |
| 5,075,099 A | 12/1991 | Srinivasan et al. |
| 5,118,797 A | 6/1992 | Jurisson et al. |
| 5,183,653 A | 2/1993 | Linder et al. |
| 5,362,476 A | 11/1994 | Sherry et al. |
| 5,364,613 A | 11/1994 | Sieving et al. |
| 5,367,080 A | 11/1994 | Toner et al. |
| 5,387,409 A | 2/1995 | Nunn et al. |
| 5,409,689 A | 4/1995 | Winchell et al. |
| 5,413,774 A | 5/1995 | Schneider et al. |
| 5,574,140 A | 11/1996 | Pollack et al. |
| 5,578,292 A | 11/1996 | Schneider et al. |
| 5,608,110 A | 3/1997 | Ramalingam et al. |
| 5,627,286 A | 5/1997 | Ramalingam et al. |

(Continued)

FOREIGN PATENT DOCUMENTS

| | | |
|---|---|---|
| EP | 230893 A2 | 8/1987 |
| EP | 458745 A1 | 11/1991 |

(Continued)

OTHER PUBLICATIONS

Faust, Andreas et al.: "Synthesis and evaluation of a novel fluorescent photoprobe for imaging matrix metalloproteinases", Bioconjugate Chemistry, vol. 19, No. 5, pp. 1001-1008, Feb. 1, 2008, XP002497488, ISSN: 1043-1802.

(Continued)

*Primary Examiner* — Michael G Hartley
*Assistant Examiner* — Sean R Donohue
(74) *Attorney, Agent, or Firm* — Vivicar Law, PLLC

(57) ABSTRACT

The invention relates to aryl-sulphonamido compounds endowed with affinity against metallo proteases MMP, having formula (I) below wherein R, $R_1$, $R_2$, $R_3$, G and n have the meanings reported in the specification, properly labelled with diagnostic imaging moieties or even radiotherapeutic moieties. The invention also refers to the process for their preparation, to pharmaceutical compositions comprising them and to their use as diagnostic imaging agents or radiotherapeutic agents.

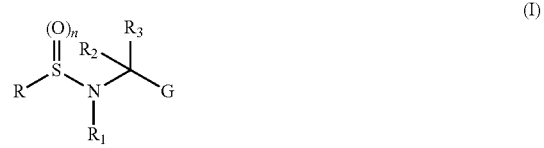

(I)

9 Claims, No Drawings

(56) References Cited

U.S. PATENT DOCUMENTS

| | | | |
|---|---|---|---|
| 5,656,254 A | 8/1997 | Ramalingam et al. | |
| 5,659,041 A | 8/1997 | Pollak et al. | |
| 5,662,885 A | 9/1997 | Pollak et al. | |
| 5,665,329 A | 9/1997 | Ramalingam et al. | |
| 5,688,487 A | 11/1997 | Linder et al. | |
| 5,711,933 A | 1/1998 | Bichon et al. | |
| 5,720,934 A | 2/1998 | Dean et al. | |
| 5,780,006 A | 7/1998 | Pollak et al. | |
| 5,840,275 A | 11/1998 | Bichon et al. | |
| 5,849,261 A | 12/1998 | Dean et al. | |
| 5,879,658 A | 3/1999 | Dean et al. | |
| 5,886,142 A | 3/1999 | Thakur et al. | |
| 5,976,495 A | 11/1999 | Pollak et al. | |
| 5,985,900 A | 11/1999 | Bender et al. | |
| 6,051,207 A | 4/2000 | Klaveness et al. | |
| 6,083,485 A | 7/2000 | Licha et al. | |
| 6,093,382 A | 7/2000 | Wedeking et al. | |
| 6,143,274 A | 11/2000 | Tweedle et al. | |
| 6,495,568 B1 | 12/2002 | Dack et al. | |
| 6,500,948 B1 | 12/2002 | Zook et al. | |
| 6,509,324 B1 | 1/2003 | Franzini et al. | |
| 6,534,041 B1 | 3/2003 | Licha et al. | |
| 6,673,804 B1 | 1/2004 | Kimura et al. | |
| 6,686,355 B2 | 2/2004 | Barvian et al. | |
| 7,067,670 B2 | 6/2006 | Boehm et al. | |
| 8,329,751 B2 * | 12/2012 | Balsamo et al. | 514/575 |
| 2005/0130973 A1 | 6/2005 | Xiang et al. | |
| 2005/0227994 A1 | 10/2005 | Gemba et al. | |
| 2005/0281741 A1 * | 12/2005 | Achilefu et al. | 424/1.69 |
| 2006/0093552 A1 * | 5/2006 | Babich et al. | 424/1.11 |

FOREIGN PATENT DOCUMENTS

| | | | |
|---|---|---|---|
| EP | 554213 A1 | 8/1993 | |
| EP | 0950656 A1 | 10/1999 | |
| JP | 2001-316254 A | 11/2001 | |
| JP | 2002-503720 A | 2/2002 | |
| JP | 2002-513409 A | 5/2002 | |
| JP | 2003-522807 A | 7/2003 | |
| JP | 2006-519216 A | 8/2006 | |
| JP | 2007-511494 A | 5/2007 | |
| JP | 2007-516245 A | 6/2007 | |
| JP | 2007-525406 A | 9/2007 | |
| RU | 2208609 C2 | 7/2003 | |
| WO | 93-06868 A1 | 4/1993 | |
| WO | 96-15815 A1 | 5/1996 | |
| WO | 96-23524 A1 | 8/1996 | |
| WO | 98-18495 A2 | 5/1998 | |
| WO | 98-18496 A2 | 5/1998 | |
| WO | 98-18497 A2 | 5/1998 | |
| WO | 98-18501 A2 | 5/1998 | |
| WO | 98/39329 A1 | 9/1998 | |
| WO | 98-39329 A1 | 9/1998 | |
| WO | 98-52618 A1 | 11/1998 | |
| WO | 98-53857 A1 | 12/1998 | |
| WO | 98-57666 A1 | 12/1998 | |
| WO | 99/42443 A1 | 8/1999 | |
| WO | 01-46207 A1 | 6/2001 | |
| WO | 01/60416 A2 | 8/2001 | |
| WO | 01-64708 A1 | 9/2001 | |
| WO | 01-70720 A2 | 9/2001 | |
| WO | 03-000830 A1 | 1/2003 | |
| WO | 2004-065407 A2 | 8/2004 | |
| WO | 2004/069365 A1 | 8/2004 | |
| WO | 2005/049005 A1 | 6/2005 | |
| WO | 2005-062828 A2 | 7/2005 | |
| WO | 2005-117832 A1 | 12/2005 | |
| WO | 2006-002873 A2 | 1/2006 | |
| WO | 2006-032911 A2 | 3/2006 | |
| WO | WO 2006067376 A2 * | 6/2006 | |
| WO | WO 2008015139 A2 * | 2/2008 | |
| WO | 2008/113756 A2 | 9/2008 | |

OTHER PUBLICATIONS

Oltenfreiter, R. et al., "Synthesis, radiosynthesis, in vitro and preliminary in vivo evaluation of biphenyl carboxylic and hydroxamic matrix metalloproteinase (MMP) inhibitors as potential tumor imaging agents", Applied Radiation and Isotopes, vol. 62, pp. 903-913, Jun. 1, 2005, XP004810523, ISSN: 0969-8043, Elsevier Ltd.

Oltenfreiter, R. et al.: "Tryptophane-based biphenylsulfonamide matrix metalloproteinase inhibitors as tumor imaging agents", Cancer Biotherapy and Radiopharmaceuticals, vol. 20, No. 6, pp. 639-647, Nov. 6, 2005, XP008096789, ISSN: 1084-9785.

Rossello, A. et al. "N-i-Propoxy-N-biphenylsulfonylaminobutylhydroxamic acids as potent and selective inhibitors of MMP-2 adn MT1-MMP", Bioorganic & Medicinal Chemistry Letters, vol. 15, No. 5, pp. 1321-1326, Jan. 12, 2005, XP004750661, ISSN: 0960-894X, Elsevier Ltd.

Rossello, A. et al.: "A new development of matrix metalloproteinase inhibitors: twin hydroxamic acids as potent inhibitors of MMPs", Bioorganic & Medicinal Chjemistry Letters, vol. 15, No. 9, pp. 2311-2314, Mar. 2, 2005, XP004851620, ISSN: 0960-894X, Elsevier Ltd.

Tamura, Y. et al.: "Highly Selective and Orally Active Inhibitors of Type IV Collagenase (MMP-9 and MMP-2): N-Sulfonylamino Acid Derivatives", Journal of Medicinal Chemistry, vol. 41, No. 4, pp. 640-649, Jan. 22, 1998, XP002072052, ISSN: 0022-2623, American Chemical Society.

Tuccinardi, T. et al.: "Amber force field implementation, molecular modelling study, synthesis adn MMP-1/MMP-2 inhibition profile of (R)- and (S)-N-hydroxy-2-(N-isopropoxybiphenyl-4-ylsulfonamido)-3-methylbutanamides", Bioorganic & Medicinal Chemistry, vol. 14, No. 12, pp. 4260-4276, Feb. 17, 2006,XP002497489, ISSN: 0968-0896, Elsevier Ltd.

Wagner, S. et al.: "Novel fluorinated derivatives of the broad-spectrum MMP inhibitors N-hydroxy-2(R)-[[4-methoxyphenyl)sulfonyl](benzyl)- and (3-picolyl)-amino]-3-methyl-butanamide as potential tools for the molecular imaging of activated MMPs with PET", Journal of Medicinal Chemistry, vol. 50, No. 23, pp. 5752-5764, Jan. 23, 2007, XP002497359, ISSN: 0022-2623, American Chemical Society.

Zheng, Q-H, et al.: "Synthesis and preliminary biological evaluation of MMP inhibitor radiotracers [11C]methyl-halo-CGS 27023A analogs, new potential PET breast cancer imaging agents", Nuclear Medicine and Biology, vol. 29, No. 7, pp. 761-770, Oct. 10, 2002, XP004388239, ISSN: 0969-8051, Elsevier Science Inc.

PCT International Search Report for PCT/EP2009/059338, mail date Oct. 28, 2009.

PCT Written Opinion of the International Searching Authority for PCT/EP2009/059338, mail date Oct. 28, 2009.

Office Action for Chinese application No. 200980128435.1, mail date Jul. 22, 2013 (English translation).

PCT International Search Report for PCT/EP2008/053078, mail date Oct. 20, 2008.

PCT Written Opinion of the International Searching Authority for PCT/EP2008/053078, mail date Oct. 20, 2008.

Rossello, A. et al.; "N-i-Propoxy-N-biphenylsulphonylamino-butylhydroxamic acids as potent and selective inhibitors of MMP- and MT1-MMP"; Bioorganic & Medicinal Chemistry Letters, Mar. 1, 2005, pp. 1321-1326, vol. 15, No. 5, XP004750661, Elsevier Science, Oxford, GB.

Rossello, A. et al.; "A new development of matrix metalloproteinase inhibitors: twin hydroxamic acids as potent inhibitors of MMPs"; Bioorganic & Medicinal Chemistry Letters, May 2, 2005, pp. 2311-2314, vol. 15, No. 9, XP004851620, Elsevier Science, Oxford, GB.

Office Action for Japanese application No. 2011-519144, mail date Aug. 13, 2013 (English translation).

Office Action for Japanese application No. 2011-519144, mail date Aug. 13, 2013 (Office Action Summary).

Alexander, Andrew L. et al., "Intracranial Black-Blood MR Angiography with High-Resolution 3D Fast Spin Echo", Magnetic Resonance in Medicine, 1998, vol. 40, No. 2, pp. 298-310, Williams & Wilkins.

(56) References Cited

OTHER PUBLICATIONS

Allcock, Harry R. et al., "Polyphosphazenes: New Polymers with Inorganic Backbone Atoms", Science, 1976, vol. 193, No. 4259, pp. 1214-1219.
Anelli, Pier Lucio et al., "L-Glutamic Acid and L-Lysine as Useful Building Blocks for the Preparation of Bifunctional DTPA-like Ligands", Bioconjugate Chemistry, 1999, vol. 10, No. 1, pp. 137-140, American Chemical Society.
Angeloni, Annino Sante et al., "The Mannich bases in polymer synthesis: 3.* Reduction of poly(β-aminoketone)s to poly(γ-aminoalcohol)s and their N-alkylation to poly(γ-hydroxy quaternary ammonium salt)s", Polymer reports, 1982, vol. 23, pp. 1693-1697, Butterworth & Col. Ltd.
Baidoo, Kwamena E. et al., "Synthesis of a Diaminedithiol Bifunctional Chelating Agent for Incorporation of Technetium-99m into Biomolecules", Bioconjugate Chem., 1990, vol. 1, No. 2, pp. 132-137, American Chemical Society.
Belien, Ann T.J. et al., "Membrane-type 1 Matrix Metalloprotease (MT1-MMP) Enables Invasive Migration of Glioma Cells in Central Nervous System White Matter", The Journal of Cell Biology, 1999, vol. 144, No. 2, pp. 373-384, The Rockefeller University Press, http://www.jcb.org.
Deguchi-Jun-O-et al., "Matrix Metalloproteinase-13/Collagenase-3 Deletion Promotes Collagen Accumulation and Organization in Mouse Atherosclerotic Plaques", Circulation, 2005, vol. 112, pp. 2708-2715, American Heart Association, Inc., http://www.circulationaha.org.
Deryugina, Elena I. et al., "Up-Regulation of Vascular Endothelial Growth Factor by Membrane-type 1 Matrix Metalloproteinase Stimulates Human Glioma Xenograft Growth and Angiogenesis", Cancer Research, 2002, vol. 62, pp. 580-588, American Association for Cancer Research, www.cancerres.aacrjournals.org.
Edelman, Robert R. et al., "Extracranial Carotid Arteries: Evaluation with "Black Blood" MR Angiography", Radiology, 1990, vol. 177, No. 1, pp. 45-50, RSNA.
Eisenwiener, Klaus-Peter et al., "A Convenient Synthesis of Novel Bifunctional Prochelators for Coupling to Bioactive Peptides for Radiometal Labelling", Bioorganic & Medicinal Chemistry Letters, 2000, vol. 10, pp. 2133-2135, Elsevier Science Ltd.
Folgueras, Alicia R. et al., "Matrix metalloproteinases in cancer: from new functions to improved inhibition strategies", Int. J. Dev. Biol., 2004, vol. 48, pp. 411-424, UBC Press, Spain, www.ijdb.ebu.es.
Frias, Juan C. et al., "Recombinant HDL-Like Nanoparticles: A Specific Contrast Agent for MRI of Atherosclerotic Plaques", J. Am. Chem. Soc., 2004, vol. 126, No. 50, pp. 16316-16317, American Chemical Society.
Golubkov, Vladislav S. et al., "Molecular Basis of Cell and Developmental Biology: Membrane Type-1 Matrix Metalloproteinase (MT1-MMP) Exhibits an Important Intracellular Cleavage Function and Causes Chromosome Iinstability", The Journal of Biological Chemistry, 2005, vol. 280, No. 26, pp. 25079-25086, The American Society for Biochemistry and Molecular Biology, Inc., doi:10.1074/jbc.M502779200.
Greene, Theodora W., "Protective Groups in Organic Synthesis", 1st Edition, Chapter 5, pp. 152-178, Chapter 7, pp. 218-223, 238-241 and 272-273, 1981, John Wiley & Sons, Inc.
Heller, J., "Controlled release of biologically active compounds from bioerodible polymers", Biomaterials, 1980, vol. 1, pp. 51-57, IPC Business Press.
Itoh, Yoshifumi et al., "Matrix metalloproteinases in cancer", Essays in Biochemistry, 2002, vol. 38, Chapter 3, pp. 21-36.
Karra, Srinivasa R. et al., "99mTc-Labeling and in Vivo Studies of a Bombesin Analogue with a Novel Water-Soluble Dithiadiphosphine-Based Bifunctional Chelating Agent", Bioconjugate Chem., 1999, vol. 10, No. 2, pp. 254-260, American Chemical Society.
Knight, C. Graham et al., "A novel coumarin-labelled peptide for sensitive continuous assays of the matrix metalloproteinases", Federation of European Biochemical Societies (FEBS Letters), 1992, vol. 296, No. 3, pp. 263-266, Elsevier Science Publishers B.V.
Koshikawa, Naohiko et al., "Role of Cell Surface Metalloprotease MT1-MMP in Epithelial Cell Migration over Laminin-5", The Journal of Cell Biology, 2000, vol. 148, No. 3, pp. 615-624, The Rockefeller University Press, http://www.jcb.org.
Liu, Shuang et al., "99mTc-Labeled Small Peptides as Diagnostic Radiopharmaceuticals", Chemical Reviews, 1999, vol. 99, No. 9, pp. 2235-2268, American Chemical Society.
Lopez-Otin, Carlos et al., "Protease Degradomics: A New Challenge for Proteomics", Nature Reviews: Molecular Cell Biology, 2002, vol. 3, pp. 509-519, Nature Publishing Group, www.nature.com/reviews/molcellbio.
Luyt, Leonard G. et al., "An N2S2 Bifunctional Chelator for Technetium-99m and Rhenium: Complexation, Conjugation, and Epimerization to a Single Isomer", Bioconjugate Chem., 1999, vol. 10, No. 3, pp. 470-479, American Chemical Society.
Maina, Theodosia et al., "Synthesis, radiochemistry and biological evaluation of a new somatostatin analogue (SDZ 219-387) labelled with technetium-99m", European Journal of Nuclear Medicine, 1994, vol. 21, No. 5, pp. 437-444, Springer-Verlag.
Mulder, Willem J. et al., "Quantum Dots with a Paramagnetic Coating as a Bimodal Molecular Imaging Probe", Nano Letters, 2006, vol. 6, No. 1, pp. 1-6, American Chemical Society, doi:10.1021/nl051935m.
Munshi, H.G. et al, "Reciprocal interactions between adhesion receptor signaling and MMP regulation", Cancer Metastasis Rev., 2006, vol. 25, pp. 45-56, Springer Science + Business Media, LLC.
Murphy, Gillian et al., "Gelatinases A and B", Methods in Enzymology, Section 28: Metallopetidases, 1995, vol. 248, pp. 470-484, Academic Press, Inc.
Neumann, Ulf et al., "Characterization of Mca-Lys-Pro-Leu-Gly-Leu-Dpa-Ala-Arg-NH2, a fluorogenic substrate with increased specificity constants for collagenases and tumor necrosis factor converting enzyme", Analytical Biochemistry, 2004, vol. 328, pp. 166-173, Elsevier Inc., www.sciencedirect.com.
Overall, Christopher M. et al., "Validating matrix metalloproteinases as drug targets and anti-targets for cancer therapy", Nature Reviews: Cancer, 2006, vol. 6, pp. 227-239, Nature Publishing Group, www.nature.com/reviews/cancer.
Rossello, Armando et al., "New N-arylsulfonyl-N-alkoxyaminoacetohydroxamic acids as selective inhibitors of gelatinase A (MMP-2)", Bioorganic & Medicinal Chjemistry Letters, vol. 12, pp. 2441-2450, 2004, Elsevier Ltd.
Rudnic, Edward, PhD et al., "Chapter 92: Oral Solid Dosage Forms", Remington: The Science and Practice of Pharmacy, 19th Edition, Alfonoso R. Gennaro, editor, 1995, pp. 1615-1649, MACK Publishing Company, Easton, Pennsylvania 18042.
Sipkins, Dorothy A. et al., "Detection of tumor angiogenesis in vivo by avβ3-targeted magnetic resonance imaging", Nature Medicine, 1998, vol. 4, No. 5, pp. 623-626, Nature Publishing Group, http://www.nature.com/naturemedicine.
Sounni, N.E. et al., "MT1-MMP expression promotes tumor growth and angiogenesis through an up-regulation of vascular endothelial growth factor expression", The FASEB Journal, 2002, vol. 16, pp. 555-564, FASEB.
Sounni, Nor Eddine et al., "Expression of Membrane Type 1 Matrix Metalloproteinase (MT1-MMP) in A2058 Melanoma Cells is Associated With MMP-2 Activation and Increased Tumor Growth and Vascularization", Int. J. Cancer, 2002, vol. 98, pp. 23-28, Wiley-Liss, Inc.
Terreno, Enzo et al., "Highly shifted LIPOCEST agents based on the encapsulation of neutral polynuclear paramagnetic shift reagents", Chem. Commun., 2008, pp. 600-602, The Royal Society of Chemistry, www.rsc.org/chemcomm.
Terreno, Enzo et al., From Spherical to Osmotically Shrunken Paramagnetic Liposomes: An Improved Generation of LIPOCEST MRI Agents with Highly Shifted Water Protons, Angewandte Chemie Int. Ed., 2007, vol. 46, pp. 966-968, Wiley-VCH Verlag GmbH & Co. KGaA, Weinheim, www.angewandte.org, doi:10.1002/anie.200604027.

(56) References Cited

OTHER PUBLICATIONS

Veprek, Pavel et al., "Peptide and Glycopeptide Dendrimers. Part I", Journal of Peptide Science, 1999, vol. 5, pp. 5-23, European Peptide Society and John Wiley & Sons, Ltd.
Veprek, Pavel et al., "Peptide and Glycopeptide Dendrimers. Part II", Journal of Peptide Science, 1999, vol. 5, pp. 203-220, European Peptide Society and John Wiley & Sons, Ltd.
Wong, Ernest et al., "Rhenium(V) and Technetium(V) Oxo Complexes of an N2N's Peptidic Chelator: Evidence of Iinterconversion between the Syn and Anti Conformations", Inorg. Chem., 1997, vol. 36, No. 25, pp. 5799-5808, American Chemical Society.
Yamamura, Norio et al., "Technetium-99m-Labeled Medium-Chain Fatty Acid Analogues Metabolized by β-Oxidation: Radiopharmaceutical for Assessing Liver Function", Bioconjugate Chem., 1999, vol. 10, No. 3, pp. 489-495, American Chemical Society.
Office Action for Australian application No. 2008228260, mail date Dec. 23, 2011.
First Office Action for Chinese application No. 200880004727.X, mail date Apr. 1, 2012 (English translation).
First Office Action for Chinese application No. 200980128435.1, mail date Apr. 13, 2012 (English translation).
Second Office Action for Chinese application No. 200980128435.1, mail date Jan. 5, 2013 (English translation).
Second Office Action for Chinese application No. 200880004727.X, mail date Jan. 17, 2013 (English translation).
Office Action for European application No. 08717820.8, mail date Jul. 24, 2012.
Final Office Action for Japanese application No. 2011-519144, mail date May 7, 2014 (English translation).
First Office Action for Russian application No. RU2009138346, mail date Dec. 28, 2011 (English translation).
Second Office Action for Russian application No. RU2009138346, mail date Aug. 1, 2012 (English translation).
Decision to Grant for Russian application No. RU2009138346, mail date Jul. 3, 2013 (English translation).

\* cited by examiner

DIAGNOSTIC AGENTS SELECTIVE AGAINST METALLOPROTEASES

This application is the national stage application of corresponding international application number PCT/EP2009/059338 filed Jul. 21, 2009, which claims priority to and the benefit of European application no. 08160856.4, filed Jul. 22, 2008, all of which are hereby incorporated by reference.

FIELD OF THE INVENTION

The present invention finds application in the field of diagnostics and, more in particular, it relates to aryl-sulphonamido metalloproteases inhibitors labelled with imaging moieties, to a process for their preparation, to pharmaceutical compositions comprising them and to their use as diagnostic imaging agents.

BACKGROUND

Many physiological and pathological processes are known to be characterised by both a significant hyperproliferation and mobility of cells. Among them are physiological processes like, for instance, embryogenesis or development and differentiation of tissues and, also, pathological processes among which are tumours or, more in general, disorders affecting a variety of body districts or organs: lungs, muscles, bones, skin as well as the nervous, lymphatic, gastrointestinal, renal, maculo-ocular, cardiovascular system, and the like.

In pathological or non-pathological conditions, high cellular proliferation and mobility mainly depends on the activity of zinc metalloproteases, a class of catalytic proteases present in humans (also referred to as proteinases) which are known to coordinate a zinc ion in their catalytic site, and which are able to hydrolyse amidic bonds within the peptidic chain of the proteins.

Among the zinc metalloproteases are extracellular matrix metalloproteases (hereinafter referred to as MMPs), ADAMS (A Disintegrin and Metalloproteases) and ADAMTs (A Disintegrin and Metalloprotease with Trombospondin Type I repeats).

Once produced, these proteases remain anchored onto the cellular membranes or are excreted in the extra-cellular matrix (ECM), an important physiological structure comprising an organized tri-dimensional network of cells of the surrounding tissues which are electrically, chemically and physically connected to each other.

As such, they may play a key role in several extracellular processes including cell-cell and cell-ECM interactions, as well as in physiological intracellular processes; e.g. growth, development and remodelling of tissues, transduction of intra- and inter-cellular signals and adhesion phenomena.

The proteolytic activity of these zinc metalloproteases, in physiological conditions, is highly and finely tuned by endogenous inhibitors known as tissue inhibitors of metalloproteases (TIMPs), which have been found to exert a fundamental role also in regulating the activity of ADAMs and ADAMTs.

Thus, the delicate equilibrium between MMPs and their inhibitors enables the proper functioning of all of the physiological roles in which MMPs are involved such as, for example, embryonic growth and development, tissue morphogenesis, cell migration and matrix remodelling, reproductive processes, i.e. menstrual cycle and ovulation, bone formation, adipogenesis, wound healing and angiogenesis or even release and processing of bioactive molecules as intra- or inter-cellular peptide signals.

Due to their diffusion in the human body and their exerted role, it is thus evident that any alteration in the regulation of even one of the above mentioned processes, for instance because of pathologies like tumours whose progression may determine either over-expression or under-expression of MMPs, would result, almost inevitably, in the occurrence of degenerative processes leading to an abnormal evolution and/or development of tissues.

Examples of the above pathologies in which over- or under-expression of MMPs may be involved, thus leading to an altered tissutal morphology with uncontrolled cell proliferation, may comprise: arthritis and connective tissue disorders; neurodegenerative disorders such as multiple sclerosis, Alzheimer's disease, stroke and ALS (Amyotrophic Lateral Sclerosis); cardiovascular disorders such as atherosclerosis, aneurism, heart failure, dilated cardiomyopathy; pulmonary diseases such as emphysema or cystic fibrosis; gastric ulcers; sepsis and autoimmune disorders.

In addition, during tissutal degeneration, the altered expression of these zinc proteases may also depend, for instance, from the cells type, the activation of their pro-enzymatic forms, genic transcription pathways as well as excretion and endocytosis mechanisms.

The extracellular and intracellular threshold of active zinc metalloproteases are often regulated onto the cell membrane surface by means of a catalytic shedding by other metalloproteases like the MMPs anchored onto the cellular membrane, known as Membrane-Type MMPs (MT-MMPS), by Tumor Necrosis Factor alpha convertase, better knows as TACE (and corresponding to ADAM-17), or by even other ADAMs or ADAMTs.

Therefore, for therapeutic purposes, when pathological affections occur as being characterized by a significant activity of metalloproteases on the cell surface of invasive and hyper-proliferating cells, it could be desirable to inhibit those MT-MMPs or some other ADAMs or ADAMTs.

So far, at least 23 different enzymes, which are known to belong to the family of MMPs, have been classified into sub-groups according to their substrate specificity. Among them are, as an example, MMP-1, MMP-8 and MMP-13 known to act on collagenase; MMP-2 and MMP-9, on the other side, known to target gelatinase; and MMP-3, MMP-10 and MMP-11 known to target stromelysin.

In addition, a fourth sub-group of membrane-type MMPs, called as MT-MMPs, have been identified and characterized so far, namely: MT1-MMP (MMP-14), MT2-MMP (MMP-15), MT3-MMP (MMP-16), MT4-MMP (MMP-17), MT5-MMP (MMP-24) and MT6-MMP (MMP-26); the exerted role, however, has been clarified for only some of them (see, for a reference, H G Munshi et al, *Cancer Metastasis Rev.*, 2006, 25, 45-56; and V S Golubkov et al., *J Biol. Chem.*, 2005, 280, 25079-25086).

As an example, MMP-14 is known to be responsible for the activation of pro-MMP-2 on the external surface of some cell types, e.g. smooth muscle cells of vascular tissue in the angiogenetic processes (see, for a reference, N. Koshikawa et al., *J. Cell. Biol.* 2000, 148, 615-624; and Y. Itoh, H. Nagase, *Essays in Biochemistry,* 2002, 38, 21-36).

In addition, MMP-14 is known to be hyper-expressed on the membranes of some types of tumoral cells, such as in melanomas (see, as a reference, NE Sounni et al., *Int. J. Cancer,* 2002, 98, 23-28), breast adenocarcinoma (see, as a reference, N E Sounni, et al., *FASEB J* 2002, 16, 555-564)

and in glyomas (A T Belien, et al., *J Cell Biol* 1999, 144, 373-384; and E I Deryugina, et al, *Cancer Res*, 2002; 62:580-588).

MMP-14 may also activate other pro-MMPs like pro-MMP-13, which hyper-expression is known to be correlated, in some cell types, to tumours, inflammation or cardiovascular and neurodegenerative disorders (see, for example, A R Folgueras et al., *Int. J. Dev. Biol.*, 2004, 48, 411-424; and J O Degushi, et al., *Circulation*, 2005, 2708-2715).

Even other MMPs are known to contribute to the activation of pro-MMP-2 and/or pro-MMP-13 and/or pro-MMP-9. As an example, MMP-15, MMP-16, MMP-17 and MMP-24 are known to activate pro-MMP-2 and pro-MMP-13; MMP-17 acts only to activate pro-MMP-2, whilst MMP-26 activates pro-MMP-2 and proMMP-9; see, as a reference, A R Folgueras et al., (*Int. J. Dev. Biol.*, 2004, 48, 411-424).

Moreover, MMP-2 and MMP-13 are produced from proliferating and invasive cells and are activated, or anyway activable, in ECM by catalytic activity of the membrane surface MT-MMPs; they represent, therefore, the prior tool for cell motility across the digestive surface permeability of ECM.

Based on previous studies on the so-called "degradomics" (see, as a reference, C Lopez-Otin et al., *Nature Rev.* 2002, 3, 509-519; and CM Overall et al., *Nature Review Cancer*, 2006, 6, 227-239), the possibility of targeting some MMPs as drug delivery candidates for cancer and other pathologies, whilst avoiding interferences with physiological roles exerted by some other MMPs, is nowadays widely acknowledged.

As such, studies are ongoing for the development of MMP inhibitors, to be used in therapy, that are able to selectively address pathological affections without the aforementioned drawbacks.

Therefore, as the activity of some MMPs should be inhibited so as to limit and counteract an occurring degenerative process, the activity of some other types of MMPs regulating physiological processes of development and morphogenesis should not be impaired, as the above may result in undesirable side effects.

Among them is, as an example, the musculoskeletal syndrome with fibroproliferative effects in the join capsule of the knee known to occur upon impairment of the normal tissue remodelling activity exerted by MMP-1. Likewise, the inhibition of some MMPs involved in tumorogenesis control such as, for instance, MMP-3, may cause an increase of cellular proliferation and invasion.

In therapy, therefore, a lack of inhibition on MMP-1 and MMP-3, considered as antitarget, is highly desirable.

On the contrary, an evident selectivity toward MMP-2 and MMP-9 was found to have pro-apoptic effects on tumor cell cultures without showing important side effects.

Therefore, the search for molecules able to specifically regulate the activity of specific MMPs, when normal mechanisms are lost, will provide useful compounds for the treatment of several diseases.

A variety of metalloproteases inhibitors, some of which referring to sulphonamido derivatives, is known in the art.

Among them are, as an example, carbocyclic side chain containing N-substituted metallo protease inhibitors, described in WO 01/70720, and pharmaceutical compositions thereof.

U.S. Pat. No. 6,686,355 discloses biphenyl derivatives possessing a cyclic nitrogen containing sulphonamido group, as MMP inhibitors.

WO 2004/069365 describes diagnostic imaging agents comprising matrix metalloproteases inhibitors bearing substituted N,N-dialkyl chain sulphonamido groups, properly labelled with a γ-emitting radionuclide.

WO 98/39329 describes sulphonamido hydroxamic acid derivatives specifically targeting MMP-2, MMP-9 and MMP-13; the several compounds therein exemplified comprise substituted N,N-dialkyl side chain sulphonamido groups.

U.S. Pat. No. 7,067,670 discloses alkyl-sulphonamido hydroxamic acid derivatives possessing inhibitory activity towards MMP-2 and MMP-13.

U.S. Pat. No. 6,500,948 discloses pyridyloxy- and pyridylthio-arylsulphonamido derivatives having MMP inhibitory activity, wherein the N atom of the sulphonamido group is part of a six membered heterocycle, bearing carbon atoms adjacent to the above N atom.

U.S. Pat. No. 6,495,568 discloses alkyl- or cycloalkyl-sulphonamido hydroxamic acid derivatives as matrix metalloproteases inhibitors.

U.S. Pat. No. 5,985,900 discloses sulphonamido derivatives being characterized by a phenyl- or phenylene-SO$_2$NH— moiety, possessing MMP inhibitory activity.

WO 99/42443 discloses sulfonylamino hydroxamic acid derivatives bearing a group aryl-SO$_2$NH—, therein indicated as matrix-degrading metalloproteinases.

Other sulphonamido MMP inhibitors are known in the art. Among them are selective inhibitors of gelatinase A (MMP-2) being disclosed by Rossello et al. in *Bioorg. & Med. Chem.* 12 (2004) 2441-2450, and having formula (A) below, wherein R is a group selected from isopropyl, allyl or p-(benzyloxy)benzyl.

Likewise, MMP-2 inhibitors showing a good MMP-2/MMP-1 selectivity were also disclosed by Tuccinardi et al (*Bioorg. & Med. Chem.* 14 (2006) 4260-4276); among the exemplified compound therein reported is the derivative of formula (B) below

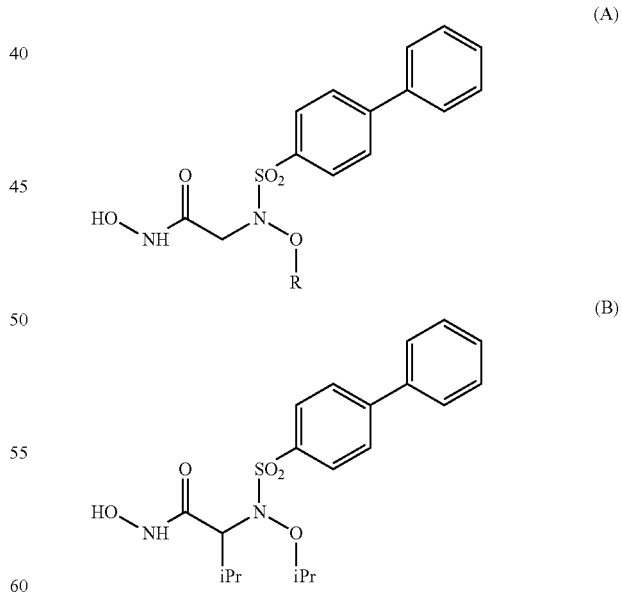

In addition to the above, previous works in this field have indicated that the use of selective MMP-2 inhibitors that spare some MMPs such as MMP-1 and MMP-3 enables to block invasion of HT1080 cells (of a highly invasive fibrosarcoma) and HUVEC (Human Umbical Vein Endothelial) cells in models of chemoinvasion and angiogenesis (A.

Rossello, et al, *Bioorg & Med. Chem.*, 2004, 12, 2441-2450; and A. Rossello, et al., *Bioorg & Med. Chem. Lett.*, 2005, 15, 1321-1326).

As reported in the aforementioned *Bioorg & Med. Chem. Lett.*, (2005), a possible anti-angiogenesis model was developed and specific compounds therein referred to as (5b) and (5c), which formulae are reported below, were synthesized

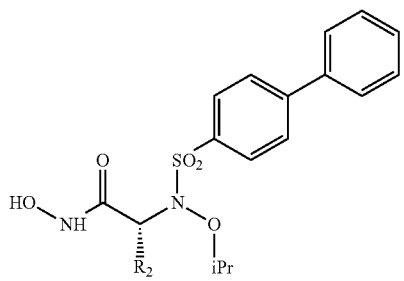

(5b) wherein $R_2$ is —$(CH_2)_2$—$NHCOOCH_2$—$C_6H_5$;
(5c) wherein $R_2$ is —$(CH_2)_2$—$NH_2$ Based on the results being obtained on isolated enzymes and according to a method described by C G Knight et al. (see, as a reference, *FEBS Lett.* 1992, 296, 263; and *Methods Enzymol.* 1995, 248, 470), the said method comprising the use of the fluorogenic substrate FS-1 (e.g. Mca-Pro-Leu-Gly-Leu-Dpa-Ala-Arg-NH$_2$) as reported by A. Rossello et al., in Bioorg. Med. Chem. Lett. 12 (2004), 2441-2450, compound (5b) proved to be a dual inhibitor of MMP-2 ($IC_{50}$ value corresponding to 0.41 nM) and of MMP-14 ($IC_{50}$ value corresponding to 7.7 nM).

A novel class of zinc metalloproteases inhibitors having aryl-sulphonamidic structure is deisclosed in WO 2008/113756 (PCT/EP2008/053078). Based on $IC_{50}$ values of inhibition tests being in the nano/subnano molar range, those compounds resulted to be particularly effective towards target enzymes, in particular MMP-2, MMP-13 and MMP-14.

Besides of being useful in the treatment of pathological conditions the said compounds may be advantageously used, in diagnostics, when suitably labelled with imaging moieties.

In this respect, the possible visualization of body tissues, organs or districts, wherein a non-physiological overexpression of given metalloproteases occur is of utmost importance, in clinical practice, as it may represent a powerful tool for the diagnosis of pathologies associated to them, for instance including inflammatory processes leading to arthritis and connective tissue disorders, as well as degenerative processes and tumours.

In this respect, MMP inhibitors labelled with imaging moieties are already known in the art as described, for instance, in WO 01/60416, WO 2004/069365, WO 2005/049005 and WO 2006/032911.

In addition, barbiturate derivatives possessing metalloproteases inhibitory activity further labelled with fluorogenic substrates are also disclosed in Bioconjugate Chem. 2008, 19, 1001-1008.

The present invention, however, refers to diagnostic agents comprising the aforementioned class of MMP inhibitors described in WO 2008/113756, further labelled with imaging moieties known in the art.

Importantly, as the metalloproteases inhibitors therein disclosed present a remarkable inhibitory activity and, also, a high degree of selectivity towards given metalloproteases, we have found that their labelling with diagnostic imaging moieties as per the invention affords a novel class of diagnostic agents with no impairment, at least to a significant extent, of affinity against the said metalloproteases.

Hence, the compounds of the invention result to maintain a very high affinity towards specific metalloproteases and allow for an optimal diagnostic visualization of the body organs, districts or tissues wherein the non physiological overexpression of those metalloproteases may occur.

Thanks to their capability to maintain the biological profile of the parent compounds from which they derive, therefore, their administration is particularly advantageous, in clinical practice, for the visualization of body areas where the compounds may target.

OBJECT OF THE INVENTION

Therefore, it is a first object of the present invention an imaging agent comprising one or more residues of the metalloproteases inhibitors of formula (I), labelled with one or more imaging moieties

wherein:
R is a group of formula —Ar—X—Ar' (II) wherein Ar is an arylene, heteroarylene, aryl or heteroaryl group and Ar', the same or different and independently from Ar, is an aryl or heteroaryl group or H; the said Ar and Ar' being optionally substituted by one or more groups selected from:
  (i) straight or branched alkyl, alkoxy, hydroxyalkyl, alkoxyalkyl, amino, aminoalkyl, alkylamino, aminoacyl, acylamino, carboxy or perfluorinated alkyl, each of which having from 1 to 4 carbon atoms in the alkyl chain;
  (ii) straight or branched $C_2$-$C_6$ alkenyl or alkynyl group;
  (iii) halogen or a cyano (—CN) group;
X is a single bond or it is a divalent linker selected from a straight or branched $C_1$-$C_4$ alkylene chain, —O—, —S—, —S(O)$_2$—, —CO—, —NR'—, —NR'CO— or —CONR'—, wherein R' is H or a straight or branched $C_1$-$C_4$ alkyl group;
$R_1$ is hydrogen, hydroxy or a group —Ra or —ORa wherein Ra is selected from straight or branched $C_1$-$C_4$ alkyl or $C_2$-$C_4$ alkenyl groups; or Ra is a group of formula (III)

wherein p is zero or an integer from 1 to 4; Z is a single bond or a divalent linker selected from —O—, —NR'—, —NR'CO— or —CONR'—, wherein R' is as above defined; r is zero or an integer from 1 to 4; and W is phenyl or a 5 or 6 membered heterocycle, each of which being optionally substituted by one or more groups selected from —NH$_2$, —COR', —CONHR', —COOR' or —SO$_2$NHR' wherein R' is as above defined, by aryl or heteroaryl or by one or more of the above groups from (i) to (ii);
$R_2$ and $R_3$ are, the same or different and each independently, H, a straight or branched $C_1$-$C_4$ alkyl group optionally substituted by hydroxyl or $C_1$-$C_4$ alkoxy groups, or a zinc binding group selected from —COOH, —COORb, —CON- HOH, —CONHORb, —CONRbOH, —CONHS(O)$_2$Rb, —CONH$_2$, —CONHRb or —P(O)(OH)$_2$, wherein Rb is a straight or branched alkyl, arylalkyl or heteroarylalkyl group having from 1 to 4 carbon atoms in the alkyl chain; or any of the above R$_2$ or R$_3$ groups is linked to R$_1$ so as to form a 5 to 7 membered heterocyclic ring, optionally substituted by one or more oxo groups (=O);

G is a group selected from straight or branched C$_1$-C$_6$ alkyl, aryl, heteroaryl or arylalkyl or it is a group —(CH$_2$)$_m$—N(R$_4$)(R$_5$);

R$_4$ is H or a group selected from —CORc, —COORc, —S(O)$_2$Rc, —CONHRc or —S(O)$_2$NHRc, wherein Rc is a group selected from C$_3$-C$_6$ cycloalkyl, straight or branched alkyl, aryl, heteroaryl, arylalkyl, heteroarylalkyl, alkylaryl, alkylheteroaryl, a 5 or 6 membered heterocyclyl, alkylheterocyclyl or heterocycloalkyl having from 1 to 4 carbon atoms in the alkyl chain;

R$_5$ is H or, together with the N atom to which they are bonded, R$_4$ and R$_5$ form an optionally benzocondensed 4 to 6 membered heterocycle, optionally substituted by a group Ra as above defined and/or by one or more oxo (=O) groups;

n is 1 or 2;

m is an integer from 1 to 6;

and the pharmaceutically acceptable salts thereof.

Upon administration of the compounds of the invention, the labelled imaging moieties can be thus detected according to conventional diagnostic imaging techniques, as set forth in more details below.

The compounds of formula (I) may have one or more asymmetric carbon atom, otherwise referred to as chiral carbon atom, and may thus exist in the form of single enantiomers, racemates, diastereoisomers and any mixture thereof, all to be intended as comprised within the scope of the present invention.

As set forth above, the imaging agents of the invention comprise one or more residues of the metalloproteases inhibitors of formula (I) properly labelled with one or more imaging moieties.

As reported in more details below, the terms "moiety" or "moieties" or even "residue" or "residues" are herewith intended to define the residual portion of a given molecule once properly attached or conjugated, either directly or through any suitable linker, to the rest of the molecule.

In this respect, and unless otherwise provided, when imaging agents of the invention comprise two or more residues of the metalloproteases inhibitors of formula (I), the said residues may be the same or different from each other.

The type of the substituents within the compounds of formula (I), the type of imaging moiety or moieties, as well as their means of attachment so as to give rise to the imaging agents of the invention, are all reported in more details below.

As set forth above, within the compounds of formula (I), R is a group of formula —Ar—X—Ar' (II) wherein Ar represents an arylene or heteroarylene group linked to —X—Ar' or, when X represents a single bond and Ar' is H, an aryl or heteroaryl group. In this context, despite the fact that arylene and heteroarylene are presently intended so as to define a divalent radical group (e.g. phenylene —C$_6$H$_4$—), both terms aryl and arylene (and thus heteroaryl and heteroarylene) are herewith used interchangeably unless otherwise provided.

In the present description, and unless otherwise provided, with the term aryl group (and thus of arylene group) we intend a carbocyclic aromatic group.

With the term heteroaryl (and thus heteroarylene) we intend a 5 or 6 membered aromatic heterocycle with from 1 to 3 heteroatoms or heteroatomic groups selected from N, NH, O or S.

Suitable examples of aryl of heteroaryl groups, when referring to Ar and Ar' and, also, to any other aryl or heteroaryl group being present within the compounds of formula (I), may thus include phenyl, pyrrolyl, furyl, thienyl, pyrazolyl, imidazolyl, oxazolyl, isoxazolyl, pyridyl, pyrimidinyl, thiazolyl, and the like.

As far as formula (II) is concerned, it is clear to the skilled person that both Ar and Ar' may be directly linked to each other, when X represents a single bond so as to give rise to a group —Ar—Ar' or, alternatively, they may be linked to each other through any suitable divalent linker among those above indicated thus providing, as an example, R groups corresponding to —Ar—O—Ar', —Ar—S—Ar', —Ar—CONR'—Ar', and the like.

In addition, and when referring to Ar' as corresponding to a hydrogen atom H, any of the above R groups could be identified, respectively, by —Ar itself (when X is a bond) or by a group —Ar—OH, —Ar—SH, —Ar—CONR'H, and the like.

As formerly reported, any of the above Ar and/or Ar' groups may be optionally further substituted, in any free position, by one or more groups as defined in items from (i) to (iii).

Among the optional substituents, and unless otherwise provided, with straight or branched alkyl with from 1 to 4 carbon atoms in the chain we intend any of the C$_1$-C$_4$ alkyl groups thus including methyl, ethyl, n-propyl, isopropyl, n-butyl, isobutyl, sec-butyl and tert-butyl.

Likewise, when referring to alkoxy we intend any of the corresponding alkyl-oxy groups such as methoxy, ethoxy, n-propoxy, isopropoxy, and the like.

From the above, the alkyl groups may be further substituted by hydroxyl (—OH), amino (—NH$_2$) or even by the aforementioned alkoxy (—OAlk) groups so as to give rise to hydroxyalkyl (HO-Alk-), aminoalkyl (H$_2$N-Alk-) or alkoxyalkyl (Alk-O-Alk-) groups, respectively.

By analogy, with the terms alkylamino we refer to an amino group being further substituted by any of the aforementioned alkyl groups, so as to give rise to Alk-NH-groups.

With the term acyl, unless otherwise provided, we intend any of the groups conventionally identifiable as Alk(CO)—groups wherein the Alk residue just represents any straight or branched C$_1$-C$_4$ alkyl group.

Suitable examples of acyl groups may thus include acetyl (CH$_3$CO—), propionyl (CH$_3$CH$_2$CO—), butirryl [CH$_3$(CH$_2$)$_2$CO—], isobutirryl [(CH$_3$)$_2$CHCO—], valeryl [CH$_3$(CH$_2$)$_3$CO—], and the like.

From the above, aminoacyl groups may thus include H$_2$NCO— as well as any of the above acyl groups wherein the alkyl chain is properly substituted by amino such as, for instance, aminoacetyl (H$_2$NCH$_2$CO—), aminopropionyl [H$_2$NCH$_2$CH$_2$CO— or CH$_3$CH(NH$_2$)CO—], and the like.

By analogy, unless otherwise provided, acylamino groups may be suitably represented by carboxamido groups wherein any of the former acyl groups is bonded to —NH— such as, for instance, acetamido (CH$_3$CONH—), propionamido (CH$_3$CH$_2$CONH—), butirramido [CH$_3$(CH$_2$)$_2$CONH—], and the like.

With the term perfluorinated alkyl we intend any of the former alkyl groups wherein all of the hydrogen atoms are replaced by fluorine atoms like, for instance, trifluoromethyl, —C$_2$F$_5$, —C$_3$F$_7$ or —C$_4$F$_9$ groups.

With the term straight or branched $C_2$-$C_6$ alkenyl or alkynyl group we intend any of the $C_2$-$C_6$ hydrocarbon chains comprising at least one double bond or triple bond, respectively.

Suitable examples of alkenyl or alkynyl groups according to the invention thus comprise vinyl, allyl, propenyl, isopropenyl, butenyl, isobutenyl, hexenyl, ethynyl, propynyl, butyryl, and the like.

Finally, with the term halogen atom we intend any of the fluorine, chlorine, bromine or iodine atoms.

According to a first embodiment of the invention, within the compounds of formula (I), R represents a group of formula (II) wherein Ar represents an optionally substituted phenylene group, X represents a single bond or a divalent linker selected from —O—, —S— or —NH— and Ar' represents H or an optionally substituted phenyl group.

Preferred substituents, in this class, are straight or branched $C_1$-$C_4$ alkyl or alkoxy groups or halogen atoms.

Even more preferably, within the compounds of formula (I), R represents a group of formula (II) wherein Ar represents a phenylene group, X represents a single bond or —O— and Ar' represents H or a phenyl group, the phenylene and phenyl groups being optionally substituted by straight or branched $C_1$-$C_4$ alkyl or alkoxy groups or by halogen atoms.

Still more preferred, within this class, are the compounds of formula (I) wherein R is a group selected from biphenyl-4-yl, 4-bromophenyl, 4-(4'-methoxyphenyl)-phenyl, 4-(4'-ethoxyphenyl)-phenyl, 4-phenoxy-phenyl, 4-(4' methoxyphenoxy)-phenyl and 4-(4' ethoxyphenoxy)-phenyl According to a different aspect of the invention, within the compounds of formula (I), $R_1$ is hydrogen, hydroxy or a group —Ra or —ORa, wherein Ra is alkyl or alkenyl or it is a group of formula (III) wherein p, Z and r are as above defined and W is phenyl or a 5 or 6 membered heterocycle, each of which being optionally further substituted as above indicated.

In the present description, and unless otherwise provided, with the term 5 or 6 membered heterocycle or heterocyclic group we intend any 5 or 6 membered aromatic or non aromatic heterocycle, hence including saturated, partly unsaturated or even fully unsaturated rings, with from 1 to 3 heteroatoms or heteroatomic groups selected from N, NH, O or S.

From the above, it is clear to the skilled person that the aforementioned definition of heterocycle or heterocyclic group also encompasses any fully unsaturated heterocycle, also known as heteroaryl group.

Suitable examples of heterocyclic groups, not including those already reported as falling within the definition of heteroaryl, may thus comprise tetrahydrofuran, pyrroline, pyrrolidine, morpholine, thiomorpholine, piperidine, piperazine, and the like.

According to a preferred embodiment of the invention, within the compounds of formula (I), $R_1$ is a group —ORa, wherein Ra is an alkyl or alkenyl group as above defined, or it is a group of formula (III) wherein p is 1 or 2, Z is a single bond or a divalent group selected from —O— or —NH—, r is 0, 1 or 2, and W is an optionally substituted phenyl or heterocyclic group as above defined.

Still more preferred, within this class, are the compounds of formula (I) wherein $R_1$ is selected from isopropoxy, benzyloxy, 4-phenyl-benzyloxy, allyloxy, 2-[2(piperazinyl-1-yl)ethoxy]ethoxy or 2-[2(4(ethylcarbonyl)piperazinyl-1-yl)ethoxy]ethoxy.

As far as $R_2$ and $R_3$ are concerned, in formula (I), they independently represent H, an optionally substituted alkyl group or a zinc binding group among those formerly reported.

Alternatively, $R_2$ or $R_3$ may be linked to $R_1$ so as to give rise to a 5 to 7 membered heterocyclic ring at least comprising one N heteroatom or, even more preferably, two adjacent N—O heteroatoms, e.g. the N atom being bonded to S, in formula (I), and the O atom being part of $R_1$ itself.

As a non limiting example, suitable compounds of formula (I) wherein one of $R_2$ or $R_3$ (e.g. $R_2$) is linked to $R_1$ so as to give rise to a 5 to 7 membered heterocyclic ring at least comprising two adjacent N—O heteroatoms, are reported below:

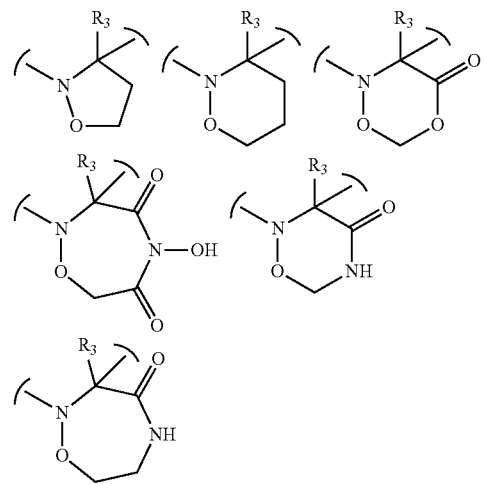

wherein the above adjacent N—O heteroatoms are represented in bold.

According to a preferred embodiment of the invention, $R_2$ and $R_3$ are selected, each independently, from H, straight or branched $C_1$-$C_4$ alkyl, —COOH, —COORb, —CONHOH or —CONHORb, wherein Rb is a straight or branched alkyl, arylalkyl or heteroarylalkyl group having from 1 to 4 carbon atoms in the alkyl chain.

Still more preferably, within this class, $R_2$ and $R_3$ are both H atoms or one of them is H and the remaining one of $R_2$ or $R_3$ is —COOH or —CONHOH.

As formerly reported, G is a group selected from straight or branched $C_1$-$C_6$ alkyl, aryl, heteroaryl or arylalkyl, the said groups being as above defined or, alternatively, G is a group of formula —$(CH_2)_m$—N($R_4$)($R_5$), wherein m, $R_4$ and $R_5$ are as set forth above.

With respect to the meanings of $R_4$, the said group may represent a hydrogen atom H or a carbonyl, carboxyl, sulphonyl, carboxamido or sulphonamido group, further derivatized through the above indicated Rc groups.

When referring to Rc, and unless otherwise provided, with the term $C_3$-$C_6$ cycloalkyl we intend any 3 to 6 membered cycloaliphatic ring such as cyclopropyl, cyclobutyl, cyclopentyl and cyclohexyl.

From the above, having defined the meanings of alkyl, aryl, heteroaryl and heterocycle (or heterocyclyl), any composite-name group such as arylalkyl, alkylaryl, heteroarylalkyl, alkylheteroaryl, alkylheterocyclyl or heterocyclylalkyl, should be clear to the skilled person.

Just as an example, and unless otherwise provided, with the term alkylaryl we intend any aryl group further substituted by alkyl: e.g. p-ethyl-phenyl ($pC_2H_5$—$C_6H_4$—); with the term arylalkyl we instead refer to an alkyl group further substituted by aryl: e.g. 2-phenyl-ethyl ($C_6H_5$—$CH_2$—$CH_2$—); and the like.

From all of the above it should be clear to the skilled person that analogous consideration may apply for heteroarylalkyl, alkylheteroaryl, heterocycloalkyl or alkylheterocyclyl groups.

With respect to $R_5$, in formula (I), it represents H or, alternatively, $R_4$ and $R_5$ together with the N atom to which they are bonded form an optionally benzocondensed 4 to 6 membered heterocycle, as above reported.

Suitable examples of the said heterocycles, for instance substituted by Ra and oxo groups, may thus comprise:

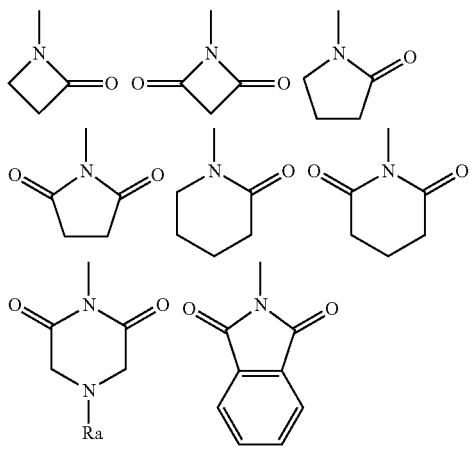

According to an additional preferred embodiment of the invention, G is a straight or branched $C_1$-$C_6$ alkyl group, preferably isopropyl, or it is a group of formula —$(CH_2)_m$—$N(R_4)(R_5)$, wherein $R_4$ is selected from —CORc, —COORc or —$S(O)_2Rc$, wherein Rc is aryl, straight or branched alkyl or an arylalkyl group having from 1 to 4 carbon atoms in the alkyl chain; and $R_5$ is H.

Even more preferred, within this class, are the compounds of formula (I) wherein $R_4$ is selected from acetyl, benzoyl, phenacetyl, 4-phenylbutanoyl, benzyloxycarbonyl, methanesulphonyl, phenylsulphonyl or benzylsulphonyl, and $R_5$ is H.

According to a still different embodiment of the invention, $R_4$ and $R_5$ together with the N atom to which they are bonded, form an N-phthalimido group.

Finally, according to an additional preferred embodiment of the invention, within the compounds of formula (I), n and m are both 2.

As formerly reported the imaging agents of the invention, otherwise referable to as contrast imaging agents, comprise one or more residues of the metalloproteases inhibitors of formula (I), further labelled with one or more imaging moieties.

In the present description, and unless otherwise provided, with the terms "contrast imaging agent" or "contrast agent", as used herein interchangeably, we refer to any detectable entity that can be used to visualize or detect, either in vitro or in vivo, a biological element including cells, biological fluids and biological tissues originating from a live mammal patient and, preferably, a human patient, as well as human body organs, regions or tissues affected by a non-physiological overexpression of metalloproteases, when the said detectable entity is used in association with a suitable diagnostic imaging technique.

As such, and unless otherwise provided, with the terms "imaging detectable moiety" and "imaging moiety or moieties", as used herein interchangeably, we intend any moiety detectable by imaging procedures, that is to say any moiety able to provide, to improve or, in any way, to advantageously modify the signal detected by an imaging diagnostic technique today in use. Among them are, for instance, magnetic resonance imaging, radioimaging, ultrasound imaging, x-ray imaging, light imaging and the like, all of which enabling the registration of diagnostically useful, preferably contrasted, images when used in association with the said techniques.

Suitable examples of the said imaging detectable moieties may thus include, for instance, chelated gamma ray or positron emitting radionuclides; paramagnetic metal ions in the form of chelated or polychelated complexes as well as of micellar systems, liposomes and microspheres; magnetic, diamagnetic or superparamagnetic coated particles, microparticles and nanoparticles; hyperpolarized NMR-active nuclei; X-ray absorbing agents including atoms of atomic number higher than 20; bubbles, microbubbles, balloons and microemulsions including biocompatible echogenic gas; reporters suitable for optical imaging including dyes, fluorescent or phosphorescent molecules, molecules absorbing in the UV spectrum, molecules capable of absorption within near or far infrared radiations, a quantum dot and, in general, all moieties which generate a detectable substance.

Further, and unless otherwise provided, the term "labelled with" means that the imaging moieties are attached, either directly or through suitable spacers or linkers, to the metalloproteases inhibitors of formula (I).

Alternatively, the MMP inhibitors of formula (I) may comprise the imaging moiety itself, as part of its chemical structure. This is the case, for instance, when the chemical structure of formula (I) comprises an isotope, either radioactive or non radioactive, which is present at levels significantly higher than those naturally observed for the said isotope. We refer, just as an example, to compounds of formula (I) comprising alkyl or fluoroalkyl groups enriched of $^{13}C$, $^{11}C$ or $^{18}F$ isotopes, known to be detectable according to conventional techniques.

According to a preferred embodiment of the invention, however, the contrast imaging agents of the invention comprise one or more residues of the metalloproteases inhibitors of formula (I) labelled with one or more imaging moieties attached to each other, either directly or through any suitable linker.

As such, just as an example, an imaging moiety could be represented by the residue of a known diagnostic agent, for instance of a chelated complex of a paramagnetic metal ion, having formula below:

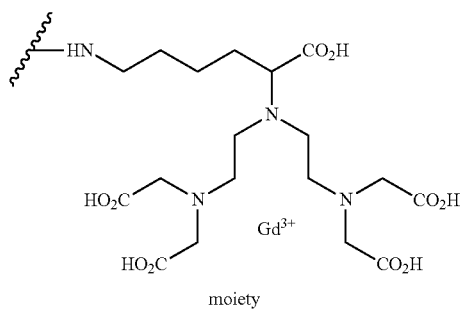

moiety

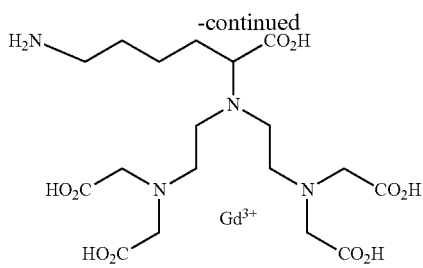

wherein the dotted line ⌇⌇⌇⌇ just represents the position of attachment of this moiety with the rest of the molecule.

Likewise, the residue or moiety referring to the metalloproteases inhibitors of formula (I) could be represented, as an example, by the following formula wherein R, $R_1$, $R_2$, $R_3$, $R_4$, n and m, as well as the line ⌇⌇⌇⌇ have the above reported meanings

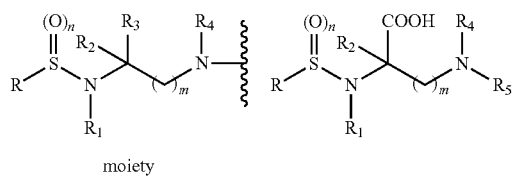

moiety

From all of the above, it should be clear to the skilled person that the compounds of the invention could be represented by a variety of formulae, all of which being characterized by one or more residues of the metalloproteases inhibitors of formula (I) labelled with one or more imaging moieties, either directly or through a linker Here below a few specific non limiting examples:

i) the residue MMP-NH— of a metalloproteases inhibitor (I) MMP-NH$_2$, directly labelled with the imaging moiety IMAGING-CO— deriving from the imaging agent IMAGING-COOH:

MMP-NHCO-IMAGING;

ii) the residue MMP-CO— of a metalloproteases inhibitor (I) MMP-COOH, directly labelled with the imaging moiety IMAGING-NH— deriving from the imaging agent IMAGING-NH$_2$:

MMP-CONH-IMAGING;

iii) the residue MMP-NH— of a metalloproteases inhibitor (I) MMP-NH$_2$, labelled with the imaging moiety IMAGING-NH— deriving from the imaging agent IMAGING-NH$_2$, through a linker —OC-link-CO— deriving from a dicarboxylic acid derivative HOOC-link-COOH:

MMP-NHCO-link-CONH-IMAGING;

iv) the residue MMP-CO— of a metalloproteases inhibitor (I) MMP-COOH labelled with more imaging moieties, for instance two imaging moieties, IMAGING-CO— deriving from the imaging agent IMAGING-COOH, through a triamino linker, for instance —HN—CH$_2$—CH(CH$_2$NH—)$_2$ deriving from H$_2$N—CH$_2$—CH(CH$_2$NH$_2$)$_2$:

MMP-CONH—CH$_2$—CH(CH$_2$—NHCO-IMAGING)$_2$ v) more residues, for instance three residues, MMP-NH— of a metalloproteases inhibitor (I) MMP-NH$_2$, labelled with one imaging moiety IMAGING-NH— deriving from the imaging agent IMAGING-NH$_2$, through a tetracarboxylic acid linker, for instance C(CH$_2$CO—)$_4$ deriving from C(CH$_2$COOH)$_4$:

IMAGING-NHCO—CH$_2$—C(CH$_2$—CONH-MMP)$_3$;

(vi) more residues, for instance two residues, MMP-NH— of a metalloproteases inhibitor (I) MMP-NH$_2$, labelled with an imaging moiety bearing two reactive functional groups, for instance two carboxylic groups —CO-IMAGING-CO— and deriving from HOOC-IMAGING-COOH:

MMP-NHCO-IMAGING-CONH-MMP;

(vii) more residues, for instance two distinct residues, MMP-CO— and MMP'-CO— of the metalloproteases inhibitors of formula (I) MMP-COOH and MMP'-COOH respectively, linked to each other through a linker —NH-link(CO—)—NH— deriving from a diamino compound further bearing a reactive carboxy functional group H$_2$N-link(COOH)—NH$_2$, the said latter reactive functional group enabling for the labelling with an imaging moiety —NH-IMAGING:

MMP-CONH-link(CONH-IMAGING)-NHCO-MMP' and the like.

The above compounds of the invention have been conveniently represented by imaging moieties "IMAGING" and by metalloproteases inhibitors of formula (I) "MMP", conjugated to each other, either directly or through a linker, so as to form carboxamido bonds.

Unless otherwise provided, the reactive functional groups allowing for the above labelling or conjugation do comprise, for instance, thiol, hydroxy, hydroxamate, phosphonic, amino and carboxy groups being present in the moiety of the metalloproteases inhibitors of formula (I), in the imaging moiety as well is in the optional linker.

Preferred reactive functional groups allowing for the above labelling or conjugation, however, comprise amino and carboxy groups leading to the formation of carboxamido linkages.

Details concerning the kind of linker, the means of attachment and, hence, the kind of conjugation between the moieties, and their position of attachment so as to give rise to the compounds of the invention, are all specifically reported in the following section.

From all of the above, as a wide range of materials detectable by diagnostic imaging modalities is known in the art, the imaging modality to be used may be selected according to the imaging detectable moiety the diagnostic compounds of the invention include.

Optical Imaging

In a preferred embodiment of the invention, within the contrast imaging agents, the labelling imaging moiety or moieties are represented by optically active imaging moieties.

Accordingly, the present invention relates to imaging agents comprising one or more residues of the metalloproteases inhibitors of formula (I) labelled with one or more optically active imaging moieties.

Suitable optically active imaging moieties include, for instance, optical dyes such as organic chromophores or fluorophores, having extensive delocalized ring systems and absorption or emission maxima in the range of 400-1500 nm; fluorescent molecules such as fluorescein; phosphorescent molecules; molecules absorbing in the UV spectrum; a quantum dot (e.g. fluorescent nanocrystals); or molecules capable of absorption of near or far infrared radiations.

Optical parameters to be detected in the preparation of an image may include, as an example, transmitted radiation, absorption, fluorescent or phosphorescent emission, light reflection, changes in absorbance amplitude or maxima, and elastically scattered radiation. For example, the biological tissue is relatively translucent to light in the near infrared (NIR) wavelength range of 650-1000 nm. NIR radiations can penetrate tissues up to several centimeters, permitting the use of the diagnostic agents of the invention comprising a NIR moiety to image target-containing tissues in vivo.

Near infrared dyes may include, for example, cyanine or indocyanine compounds such as, Cy5.5, IRDye800, indocyanine green (ICG) and derivatives thereof, including the tetrasulfonic acid substituted indocyanine green (TS-ICG), and combinations thereof. In another embodiment, the compounds of the invention may include photolabels, such as optical dyes, including organic chromophores or fluorophores, having extensively conjugated and hence delocalized ring systems and having absorption or emission maxima in the range of 400-1500 nm. The compounds of the invention may alternatively be derivatized with bioluminescent molecules. The preferred range of absorption maxima for photolabels is between 600 and 1000 nm to minimize interference with the signal from hemoglobin. Preferably, photoadsorption labels have large molar absorptivities, e.g. $>10^5$ cm$^{-1}$M$^{-1}$, while fluorescent optical dyes have high quantum yields. Examples of optical dyes include, but are not limited to, those described in U.S. Pat. No. 6,051,207, U.S. Pat. No. 6,083,485, U.S. Pat. No. 6,534,041, WO 96/23524 and references cited therein.

As an example, after injection of the optically-labelled diagnostic derivative of the invention, the patient is scanned with one or more light sources (e.g., a laser) in the appropriate wavelength range for the photolabel thus employed. The light used may be monochromatic or polychromatic either continuous or pulsed. Transmitted, scattered, or reflected light is detected via a photodetector tuned to one or multiple wavelengths to determine the location of the target-containing tissue, organ or district (for instance the body area characterized by a non-physiological overexpression of metalloproteases) in the subject. Changes in the optical parameter may be also monitored over time to detect accumulation of the optically-labelled derivative at the target site. Standard image processing and detecting devices may be used in conjunction with the optical imaging derivatives of the present invention.

In an embodiment of the invention, the labelling moiety for optical imaging is selected from the group of cyanine, indocyanines, phthalocyanines, naphthocyanines, porphyrins, pyrilium, azulenium or azo dyes, anthraquinones, naphthoquinones.

Preferably, within this class are fluorescein, 5-carboxyfluorescein, indocyanine green, Cy5, Cy5.5, and derivatives thereof.

The optical imaging agents described above may also be used for acousto-optical or sonoluminescent imaging performed with optically labelled imaging agents according to known methods (see, as an example, U.S. Pat. No. 5,171, 298, WO 98/57666 and references cited therein). In acousto-optical imaging, ultrasound radiation is applied to the subject so as to affect the optical parameters of the transmitted, emitted or reflected light. In sonoluminescent imaging, the applied ultrasound actually generates the light detected.

As a preferred example, the above conjugation or labelling may occur between a carboxyl or amino function of the optically active imaging moiety, and the amino or carboxyl function of the metalloproteases inhibitor of formula (I) or, optionally, with the ending amino or carboxyl functions of a linker between them.

In any case, any of the functional groups involved in the said conjugation reactions so as to give rise to the imaging agents of the invention are suitably selected in order not to reduce or modify the imaging capability of the optically active agent, nor to impair the affinity of the inhibitor against metalloproteases.

MRI Contrast Agents

In an additional preferred embodiment of the invention, within the contrast imaging agents the labelling imaging moiety or moieties are MRI detectable moieties.

Accordingly, the present invention also relates to imaging agents comprising one or more residues of the metalloproteases inhibitors of formula (I), labelled with one or more MRI detectable moieties.

The said MRI detectable moiety may thus comprise the residue of a chelating ligand that is labelled, in its turn, with a paramagnetic metal element detectable by MRI techniques.

Preferred paramagnetic metal elements are those having atomic number ranging between 20 and 31, 39, 42, 43, 44, 49 and between 57 and 83.

More preferred are paramagnetic metal ions selected from the following: Fe$^{(2+)}$, Fe$^{(3+)}$, Cu$^{(2+)}$, Ni$^{(2+)}$, Rh$^{(2+)}$, Co$^{(2+)}$, Cr$^{(3+)}$, Gd$^{(3+)}$, Eu$^{(3+)}$, Dy$^{(3+)}$, Tb$^{(3+)}$, Pm$^{(3+)}$, Nd$^{(3+)}$, Tm$^{(3+)}$, Ce$^{(3+)}$, Y$^{(3+)}$, Ho$^{(3+)}$, Er$^{(3+)}$, La$^{(3+)}$, Yb$^{(3+)}$, Mn$^{(3+)}$, Mn$^{(2+)}$; Gd$^{(3+)}$ being the most preferred one.

With the term "chelator", "chelating ligand" or "chelating agent", as used herein interchangeably, we intend chemical moieties, agents, compounds or molecules characterized by the presence of polar groups able to a form a complex containing more than one coordinated bond with a transition metal or another metal entity. In a preferred aspect of the invention the said chelating ligand includes cyclic or linear polyamino, polycarboxylic or polyphosphonic acids. The said ligands comprise, in addition, groups that allow for the conjugation (i.e. labelling) with the rest of the molecule. Typically, the said groups include thiol, amino or carboxyl functions either present as such or as optionally activated functions.

As a preferred example, the above conjugation or labelling may occur between a carboxyl or amino function of the chelating ligand and the amino or carboxyl function of the metalloproteases inhibitor of formula (I) or, optionally, with the ending amino or carboxyl functions of the linker between them.

In any case, any of the functional groups involved in the said conjugation reactions so as to give rise to the compounds of the invention are suitably selected in order not to reduce or modify the chelating capability of the ligand residue, nor to impair the selectivity of the inhibitor against metalloproteases.

As formerly reported, for MRI purposes, the chelating ligands are in their turn labelled with the selected paramagnetic metal, so as to form a chelate or coordinate complex with that metal.

Suitable chelating ligands include those selected from the group consisting of: polyaminopolycarboxylic acids and derivative thereof comprising, for example, diethylenetriamine pentaacetic acid (DTPA), benzo-DTPA, dibenzo-DTPA, phenyl-DTPA, diphenyl-DTPA, benzyl-DTPA, dibenzyl DTPA, N,N-Bis[2-[(carboxymethyl)[(methylcarbamoyl)methyl]ethyl]-glycine (DTPA-BMA), N-[2-[bis(carboxymethyl)amino]-3-(4-ethoxyphenyl)propyl)]-N-[2-[bis(carboxymethyl) amino]ethyl]glycine (EOB-DTPA), 4-carboxy-5,8,11-tris(carboxymethyl)-1-phenyl-2-oxa-5,8, 11-triazamidecan-13-oic acid (BOP TA), N,N-bis[2-[bis(carboxymethyl)amino]ethyl]L-glutamic acid (DTPA-GLU) and DTPA-Lys; ethylenediaminotetraacetic acid (EDTA); 1,4,7,10-teraazacyclododecane-1,4,7,-triacetic acid (DO3A) and derivatives thereof including, for example, [10-(2-hydroxypropyl)-1,4,7,10-teraazacyclododecane-1,4,7,-triacetic acid (HPDO3A); 1,4,7-triazacyclononane-N,N',N''-triacetic acid (NOTA); 6-[bis(carboxymethyl)amino]

tetrahydro-6-methyl-1H-1,4-diazepine-1,4(5H)-diacetic acid (AAZTA) and derivative thereof, for instance including those disclosed in WO 03/008390, incorporated herein by reference, 1,4,7,10-tetraazacyclotetradecane-1,4,7,10-tetraacetic acid (DOTA) and derivatives thereof including, for instance, benzo-DOTA, dibenz o-DOTA, (α,α',α",α'")-tetramethyl-1,4,7,10-tetraazacyclo-tetradecane-1,4,7,10-tetraacetic acid (DOTMA); and 1,4,8,11-tetraazacyclotetradecane-N,N',N",N'"-tetraacetic acid (TETA); or corresponding compounds wherein one or more of the carboxylic groups is replaced by a phosphonic and/or phosphinic group including, for instance, N,N'-bis-(pyridoxal-5-phosphate)-ethylenediamine-N,N'-diacetic acid (DPDP); ethylenedinitrilotetrakis(methylphosphonic) acid (EDTP), 1,4,7,10-tetraazacyclotetradecane-1,4,7,10-tetra (methylenephosphonic) acid (DOTP), the phosphonoalkyl-polyaza macrocyclic compounds disclosed in U.S. Pat. No. 5,362,476 and U.S. Pat. No. 5,409,689; the linear phosphonoalkyl derivatives disclosed in U.S. Pat. No. 6,509,324; as well as macrocyclic chelants such as texaphirines, porphyrins and phthalocyanines.

Preferred chelating ligands according to the present invention include DTPA and derivatives thereof comprising, for instance, DTPA-Glu and DTPA-Lys; DOTA and derivatives thereof; AAZTA and derivatives thereof; EDTA and derivatives thereof; TETA and derivatives thereof [see, for a general reference, Bioconj. Chem. (1999), 10, 137; Bioorg. Chem. Lett. (2000), 10, 2133; WO 93/06868; WO 01/046207; WO 01/64708; WO 04/065407; WO 05/062828; and WO 06/002873]. More specifically, the said chelating ligands preferably comprise those having the following formulae:

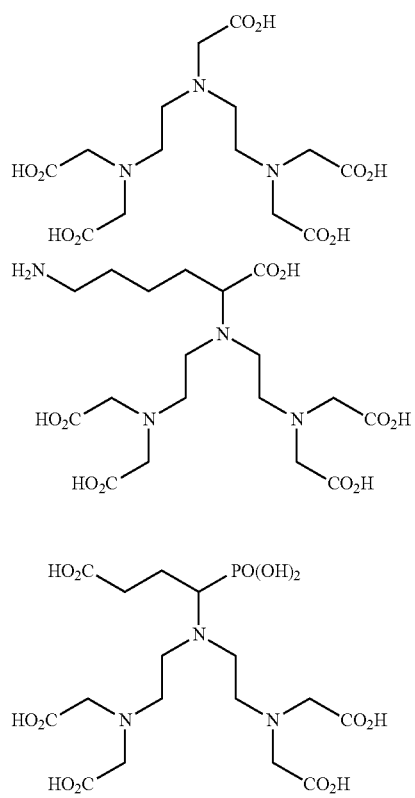

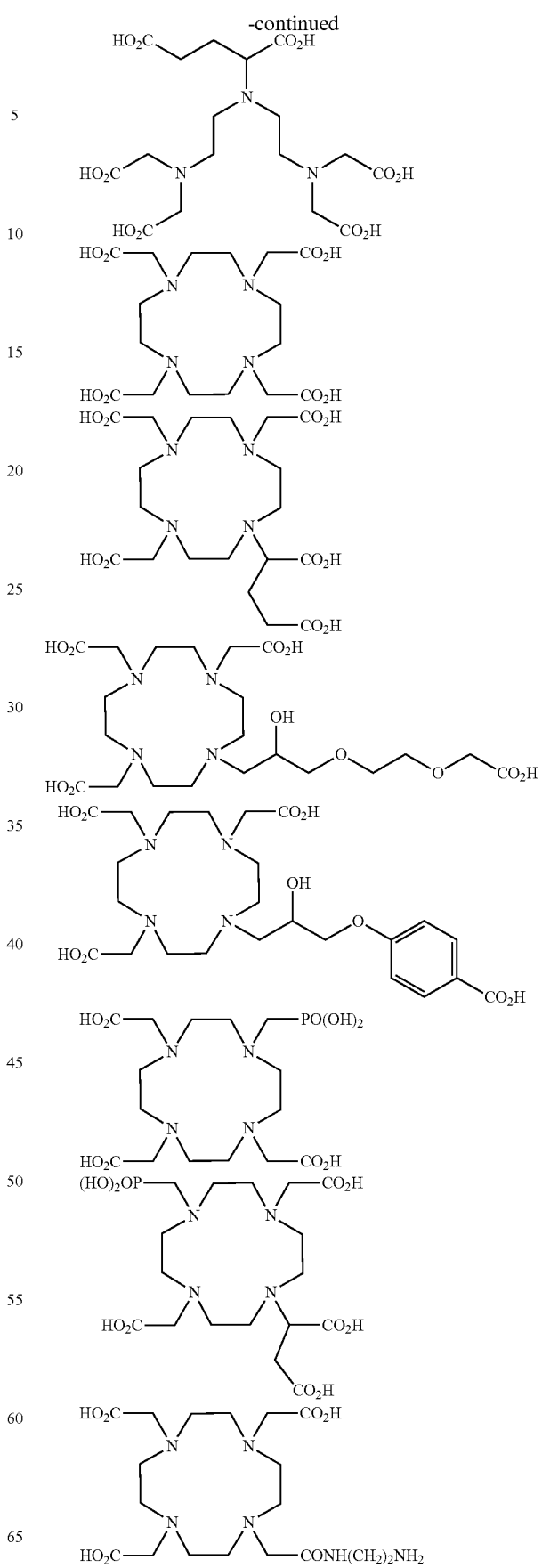

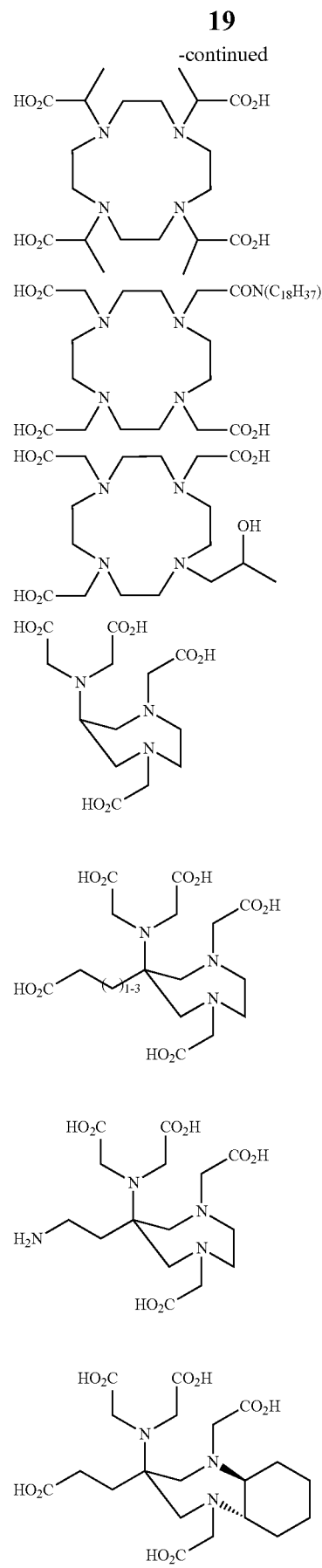

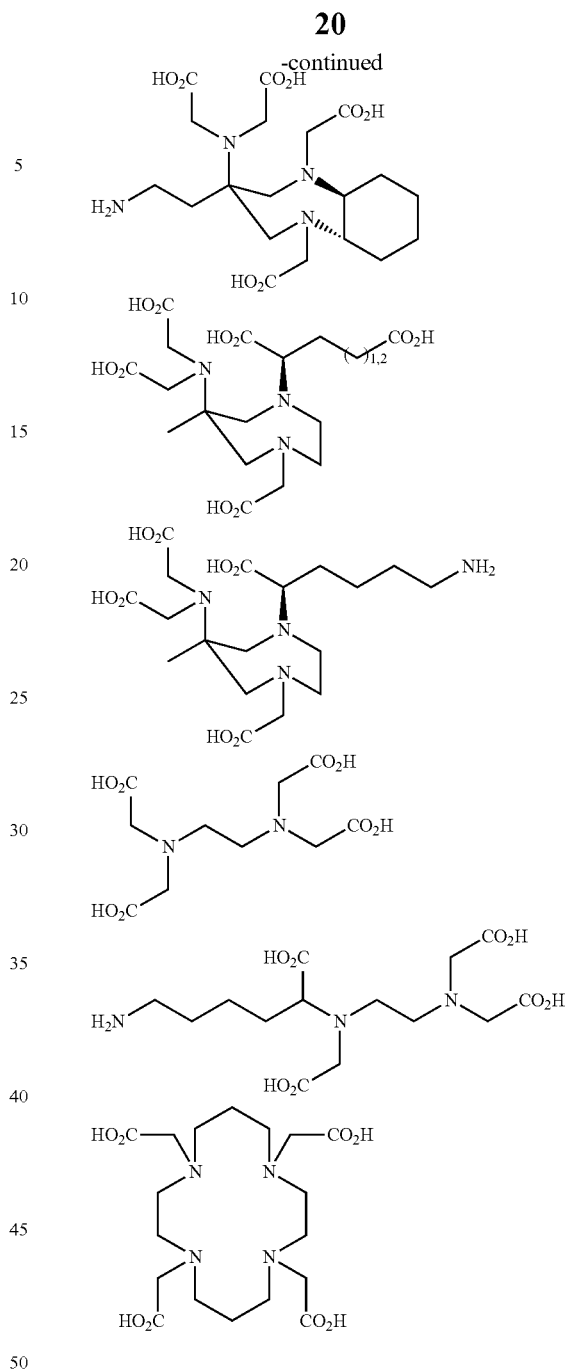

According to an additional embodiment of the invention, the labelling moiety may comprise a ligand able to chelate or form a complex with a radionuclide. In this respect, and according to the kind of radionuclide, to the chelating agent and to technique thus employed, the compounds of the invention may be used either in diagnostics, for instance in the presence of radioimaging detectable moieties, and also in therapy, when labelling occurs with radiotherapeutic moieties, as reported in more details below.

Nuclear Imaging (Radionuclide Imaging) and Radiotherapy

Therefore, the present invention also relates to novel contrast agents for radioimaging and novel radiotherapeutic agents.

As such, according to an additional embodiment of the invention, there are provided imaging agents comprising one or more residues of the metalloproteases inhibitors of formula (I), labelled with one or more radioimaging detectable moieties.

In addition, also provided are radiotherapeutic agents comprising one or more residues of the metalloproteases inhibitors of formula (I), labelled with one or more radiotherapeutic moieties.

Unless otherwise provided, with the term "radioimaging detectable moiety", as used herein, we refer to a moiety that is detectable by imaging techniques known in the art such as, for instance, scintigraphic imaging, Single Photon Emission Computed Tomography (SPECT) and Positron Emission Tomography (PET).

As such, the said radioimaging detectable moiety may comprise the residue of a chelating agent or ligand labelled with a radionuclide detectable by the above scintigraphic, SPECT or PET imaging techniques.

On the other side, when referring to radiotherapeutic moieties we rely, in particular, to the residue of a chelating agent or ligand labelled with a therapeutically active radionuclide.

As far as the terms "moiety or moieties" and "residue or residues" of chelating agents or ligands are concerned, see the aforementioned paragraphs and comments thereof.

Suitable chelating ligands are those above reported for MRI imaging techniques and further include linear or macrocyclic ligands purposely intended for radionuclides. Suitable examples, among these latter, are: terpyridine and $N_3S$, $N_2S_2$, $N_2S_3$, $N_2S_4$, $N_3S_3$ or $N_4$ chelators comprising, for instance, those disclosed in U.S. Pat. No. 5,367,080, U.S. Pat. No. 5,364,613, U.S. Pat. No. 5,021,556, U.S. Pat. No. 5,075,099 and U.S. Pat. No. 5,886,142. Other examples are known in the art and include, for instance, 6-hydrazinopyridine-3-carboxylic acid (HYNIC), 1,4,8,11-tetraazacyclotetradecane-N,N',N'',N'''-tetraacetic acid (TETA), and bis-amino bis-thiol (BAT) chelators such as those disclosed in U.S. Pat. No. 5,720,934.

$N_4$ chelating ligands are also described, for instance, in U.S. Pat. No. 5,608,110, U.S. Pat. No. 5,665,329, U.S. Pat. No. 5,656,254 and U.S. Pat. No. 5,688,487. Certain $N_3S$ or $N_2S_2$ chelators are described, for instance, in U.S. Pat. No. 5,659,041, U.S. Pat. No. 5,574,140, U.S. Pat. No. 5,780,006, U.S. Pat. No. 5,662,885 and U.S. Pat. No. 5,976,495. The chelators may also include derivatives of the chelating ligand mercapto-acetyl-acetyl-glycyl-glycine (MAG3), which contains an $N_3S$ and $N_2S_2$ system such as MAMA (monoamidemonoaminedithiols), DADS ($N_2S$ diaminedithiols), CODADS, and the like. These ligand systems, and a variety of others, are described by Liu Edwards et al., in Chem Rev, 1999, 99, 2235-2268, and cited references therein.

The chelators may also include complexes containing ligand atoms that are not donated to the metal in a tetradentate array such as, for instance, the boronic acid adducts of technetium and rhenium dioximes described in U.S. Pat. No. 5,183,653, U.S. Pat. No. 5,387,409 and U.S. Pat. No. 5,118,797.

Preferred radionuclides according to the present invention include, for instance: $^{99m}Tc$, $^{51}Cr$, $^{67}Ga$, $^{68}Ga$, $^{47}Sc$, $^{167}Tm$, $^{141}Ce$, $^{111}In$, $^{113}In$, $^{168}Yb$, $^{175}Yb$, $^{140}La$, $^{90}Y$, $^{88}Y$, $^{153}Sm$, $^{166}Ho$, $^{165}Dy$, $^{166}Dy$, $^{61}Cu$, $^{62}Cu$, $^{64}Cu$, $^{67}Cu$, $^{97}Ru$, $^{103}Ru$, $^{186}Re$, $^{188}Re$, $^{203}Pb$, $^{211}Bi$, $^{212}Bi$, $^{213}Bi$, $^{214}Bi$, $^{105}Rh$, $^{109}Pd$, $^{117m}Sn$, $^{149}Pm$, $^{161}Tb$, $^{177}Lu$, $^{198}Au$, $^{111}Ag$, $^{199}Au$, $^{51}Mn$, $^{52m}Mn$, $^{52}Fe$, $^{60}Cu$, $^{72}As$, $^{94m}Tc$, or $^{110}In$, $^{142}Pr$, $^{159}Gd$.

The choice of the radionuclide will be based on the desired therapeutic or diagnostic application.

For example, for therapeutic purposes (for instance to provide radiotherapy for primary tumours and metastasis), the radioactive nuclide is known to emit ionizing radiations such as beta particles, alpha particles and Auger or Coster-Kroning electrons and is preferably selected from the group consisting of: $^{64}Cu$, $^{90}Y$, $^{105}Rh$, $^{111}In$, $^{117m}$, $^{149}Pm$, $^{153}Sm$, $^{161}Tb$, $^{166}Dy$, $^{166}Ho$, $^{175}Yb$, $^{177}Lu$, $^{186/188}Re$, and $^{199}Au$; with $^{186/188}Re$, $^{177}Lu$ and $^{90}Y$ being particularly preferred.

In this respect, it is known to the skilled person that the selection of a proper radionuclide, for use in a particular radiotherapeutic application, may depend on several factors, including:
a. Physical half-life—This should be long enough to allow synthesis and purification of the radiotherapeutic construct from the radiometal and the conjugate, and delivery of said construct to the site of administration (injection), without significant radioactive decay prior to injection. Preferably, the radionuclide should have a physical half-life between about 0.5 and about 8 days.
b. Energy of the emission(s) from the radionuclide—Radionuclides that are particle emitters (such as alpha emitters, beta emitters and Auger electron emitters) are particularly useful, as they emit highly energetic particles that deposit their energy over short distances, thereby producing a highly localized damage. Beta emitting radionuclides are particularly preferred, as the energy from beta particle emissions from these isotopes is deposited within about 5 to about 150 cell diameters. Radiotherapeutic agents prepared from these nuclides are capable of killing diseased cells that are relatively close to their site of localization, but cannot travel long distances to damage adjacent normal tissues such as bone marrow.
c. Specific activity (i.e. radioactivity per mass of the radionuclide)—Radionuclides that have high specific activity (e.g., generator produced $^{90}Y$, $^{111}In$ or $^{177}Lu$) are particularly preferred. The specific activity of a radionuclide is determined by its method of production, the particular target for which it is produced and the properties of the isotope under consideration.

Many of the lanthanides and lanthanoids include radio-isotopes that have nuclear properties that make them suitable for use as radiotherapeutic agents, as they emit beta particles. Some of these are listed in the following table.

| Isotope | Half-Life (days) | Max b-energy (MeV) | Gamma energy (keV) | Approximate range of b-particle (cell diameters) |
|---|---|---|---|---|
| $^{149}$-Pm | 2.21 | 1.1 | 286 | 60 |
| $^{153}$-Sm | 1.93 | 0.69 | 103 | 30 |
| $^{166}$-Dy | 3.40 | 0.40 | 82.5 | 15 |
| $^{166}$-Ho | 1.12 | 1.8 | 80.6 | 117 |
| $^{175}$-Yb | 4.19 | 0.47 | 396 | 17 |
| $^{177}$-Lu | 6.71 | 0.50 | 208 | 20 |
| $^{90}$-Y | 2.67 | 2.28 | — | 150 |
| $^{111}$-In | 2.810 | Auger electron emitter | 173, 247 | <5 * m | wherein: Pm is Promethium, Sm is Samarium, Dy is Dysprosium, Ho is Holmium, Yb is Ytterbium, Lu is Lutetium, Y is Yttrium, In is Indium.

The use of radioactive rhenium isotope as an alternative to the above lanthanides and lanthanoids is well known in the art.

Particularly, $^{186/188}$Re isotopes have proved to be of particular interest in nuclear medicine, having a large number of applications in radiopharmaceutical therapy.

Because of the targeting capability of the compounds of the invention towards given metalloproteases, the radiotherapeutic agents of the invention enable to bring the chelated radioactive isotopes to the pathological tissues overexpressing metalloproteases and being thus characterized by a pathological condition, for instance a degenerative process including tumours. Hence, because of the cytotoxic amount of ionizing radiations from the beta- or alpha-particles emitting radioisotopes, targeted therein, tumoral cell death may thus occur.

For diagnostic purposes instead (for instance to locate tissues overexpressing metalloproteases) the preferred radionuclides may include $^{64}$Cu, $^{67}$Ga, $^{68}$Ga, $^{99m}$Tc, and $^{111}$In. $^{99m}$Tc is particularly preferred for diagnostic applications because of its low cost, availability, imaging properties and high specific activity. In particular, the nuclear and radioactive properties of $^{99m}$Tc make this isotope an ideal scintigraphic imaging agent. This isotope, in fact, has a single photon energy of 140 keV and a radioactive half-life of about 6 hours, and is readily available from a $^{99}$Mo-$^{99m}$Tc generator.

Preferred metal radionuclides for use in PET imaging are positron emitting metal ions such as, for instance, $^{51}$Mn, $^{52}$Fe, $^{60}$Cu, $^{68}$Ga, $^{72}$As, $^{94m}$Tc or $^{110}$In.

The choice of the suitable ligand residue depends on the radionuclide used for the ligand labelling. Thus, in the case of $^{111}$In and radioactive lanthanides such as, for instance, $^{177}$Lu, $^{90}$Y, $^{153}$Sm, $^{166}$Ho, $^{67}$Ga, $^{68}$Ga, $^{61}$Cu, $^{62}$Cu, $^{64}$Cu or $^{67}$Cu, preferred residues include those above reported for MRI. Additional radionuclide chelants, for instance to be intended for radioactive $^{99m}$Tc, $^{186}$Re and $^{188}$Re, are those disclosed in Bioconj. Chem., 1999, 10, 489; Bioconj. Chem., 1999, 10, 470; Bioconj. Chem., 1990, 1, 132; Bioconj. Chem., 1999, 10, 254; Eur. J. Nucl. Med. 1994, 21, 437; Inorg. Chem. 1997, 36, 5799; U.S. Pat. No. 5,608,110; U.S. Pat. No. 6,143,274; U.S. Pat. No. 6,093,382; U.S. Pat. No. 5,627,286; U.S. Pat. No. 5,662,885; U.S. Pat. No. 5,780,006; and U.S. Pat. No. 5,976,495, which are incorporated by reference herein in their entirety.

In addition to the above, it is well known in the art that imaging techniques like PET may be also accomplished by means of sugar moieties labelled with non-metal radionuclides including g, as an example, $^{124}$I, $^{125}$I, $^{131}$I, $^{123}$I, $^{77}$Br, $^{76}$Br, and $^{18}$F; $^{18}$F being as particularly preferred.

Therefore, the present invention also relates to agents for PET imaging techniques comprising one or more residues of metalloproteases inhibitor of formula (I) labelled with one or more sugar moieties that are, in their turn, labelled with halogen radionuclides.

As far as the possible means of conjugation or labelling between the metalloproteases inhibitors and the radioimaging detectable or radiotherapeutic moiety, either directly or through a suitable linker, see the above considerations reported for MRI agents.

Ultrasound Contrast Agents

According to an additional embodiment of the invention, the compounds of formula (I) possessing MMP inhibitory activity may be properly labelled with a moiety that, though not directly interacting with a detection system, enables the formation of larger arrays of molecules that can be conversely detected by equipments or apparatus.

We refer, in this respect, to compounds of formula (I) suitably conjugated with a moiety, for instance a lipid or phospholipid moiety or even a polymeric material that enables, upon agitation (e.g., shaking, stirring, etc.), the formation of liposomes, micellar systems, vesicles or microspheres suitably including an echogenic gas, thus providing a macromolecular compound for use in ultrasound imaging techniques.

See, for a general reference, WO 98/53857, WO 98/18498, WO 98/18495, WO 98/18497, WO 98/18496 and WO 98/18501, incorporated herein by reference in their entirety.

Therefore, according to an additional object of the invention, there are provided compounds comprising the residue of a metalloproteases inhibitor of formula (I) labelled with a moiety enabling for the formation of the above liposomes, microbubbles, microballoons, microspheres or emulsions, wherein the moiety is selected from the group consisting of surfactants, sphingolipids, oligolipids, phospholipids, proteins, polypeptides, carbohydrates, synthetic or natural polymeric materials and mixtures thereof.

Preferably, herewith provided are compounds comprising the residue of a metalloproteases inhibitor of formula (I) labelled with a lipidic or phospholipidic component enabling for the formation of the above liposomes, microbubbles, microballoons, microspheres or emulsions.

Interestingly, as the said liposomes are formed according to conventional techniques by properly agitating these latter compounds, the liposomes thus formed will comprise, on their surface, a high number of metalloproteases inhibitor targeting moieties.

A further embodiment of the invention is thus represented by an ultrasound contrast agent in the form of liposomes, microbubbles, microballoons, microspheres or even emulsions, containing a material capable of generating an echogenic gas, further labelled with a plurality of residues of the metalloproteases inhibitors of formula (I).

In the present description, and unless otherwise provided, with the term "lipid", "phospholipid" or "lipidic/phospholipidic component", as used herein, we intend a synthetic or naturally-occurring amphipatic compound which comprises a hydrophilic component and a hydrophobic component. Lipids include, for example, fatty acids, neutral fats, phosphatides, glycolipids, aliphatic alcohols and waxes, terpenes and steroids.

Examples of suitable lipids according to the invention include: phosphatidylcholines such as dioleoylphosphatidylcholine, dimyristoylphosphatidylcholine, dipalmitoyl-phosphatidylcholine and diasteroylphosphatidylcholine; phosphatidyl-ethanolamines such as dipalmitoylphosphatidylethanolamine, dioleoylphosphatidylethanolamine and N-succinil-dioleoylphosphatidyl-ethanolamine; phosphatidylserine; dipalmitoylphosphatidylserine; phosphatidylglycerols; sphingolipids; glycolipids such as ganglioside GM1; glucolipids; sulphatides; phosphatidic acid and derivatives such as dipalmitoyl phosphatidic acid (DPPA); fatty acids including palmitic, stearic, arachidonic, lauric, myristic, lauroleic, physeteric, myristoleic, palmitoleic, petroselinic, oleic, isolauric, isomyristic and isostearic fatty acids; cholesterol and derivatives such as cholesterol hemisuccinate or sulphate and cholesteryl-(4-trimethylammonio)-butanoate; polyoxyethylene fatty acids esters, alcohols or alcohol ethers; polyoxyethylated sorbitan fatty acid esters, glycerol polyethylene glycol oxy-stearate; glycerol polyethylene glycol ricinoleate; ethoxylated soybean sterols; ethoxylated castor oil; polyoxyethylene polyoxypropylene fatty acid polymers; polyoxyethylene fatty acid stearates; 1,2-dioleoyl-sn-glycerol; 1,2-dipalmitoyl-sn-3-succinylglycerol; 1,3-dipalmitoyl-2-succinylglycerol; 1-hexadecyl-2-palmitoyl-glycerophosphoethanolamine; N-succinyl-dioctadecylamine; palmitoylhomocysteine; lauryltrimethylammonium bromide; cetyltrimethyl-ammonium bromide; myristyltrimethylammonium bromide; alkyldimethylbenzylammonium chloride wherein alkyl is a $C_{12}$, $C_{14}$ or $C_{16}$ alkyl; benzyldimethyldodecylammonium bromide; benzyldimethyldode cyl ammonium chloride; benzyldimethylhexadecylammonium bromide; benzyldimethylhexadecylammonium chloride; benzyldimethyltetradecyl ammonium bromide; benzyldimethyltetradecyl ammonium chloride; cetyldimethylethylammonium chloride; cetylpyridinium bromide; cetylpyridinium chloride; N-[1,2,3-dioleoyloxy)-propyl]-N,N,N-trimethylammonium chloride (DOTMA); 1,2-dioleoyloxy-3-(trimethylammonium)propane (DOTAP); and 1,2-dioleoyl-c-(4'-trimethylammonium)-butanoyl-sn-glycerol (DOTB).

With the term "liposomes", as used herein, we refer to a generally spherical cluster or aggregate of amphipatic compounds, including lipid/phospholipid compounds, typically in the form of one or more concentric layers, for example bilayers. They may also be referred to herein as lipid vesicles.

With the term "vesicle", as used herein, we refer to a spherical entity which is characterized by the presence of an internal void. Preferred vesicles are formulated from lipids, including the various lipids described herein and, in any given vesicle, the lipids may be in the form of monolayer or bilayer.

The lipid vesicles described herein include such entities commonly referred to as liposomes, micelles, bubbles, microbubbles, microspheres and the like. The internal void of the vesicles may be filled with a gas or a gaseous precursor.

The term "bubbles", as used herein, refers to a vesicle which is generally characterized by the presence of one or more membranes or walls surrounding an internal void that is filled with a gas or a gas precursor.

The terms "microspheres" and "microballoon", as used herein, preferably refer to spheres having a diameter of less than, or equal to, 10 microns.

These microballoons have an envelope including a biodegradable physiologically compatible polymer or a biodegradable solid lipid. The polymers useful for the preparation of the microballoons of the present invention can be selected from the biodegradable physiologically compatible polymers such as any of those described in: EP 458745, U.S. Pat. No. 5,711,933, U.S. Pat. No. 5,840,275, EP 554213, U.S. Pat. No. 5,413,774 and U.S. Pat. No. 5,578,292, the entire content of which is incorporated herein by reference.

In particular, the polymer can be selected from biodegradable physiologically compatible polymers, such as polysaccharides of low water solubility, polylactides and polyglycolides and their copolymers, copolymers of lactides and lactones such as ε-caprolactone, γ-valerolactone and polypeptides. Other suitable polymers include poly(ortho) esters (see, for a reference, U.S. Pat. No. 4,093,709, U.S. Pat. No. 4,131,648, U.S. Pat. No. 4,138,344 and U.S. Pat. No. 4,180,646); polylactic and polyglycolic acid and their copolymers, for instance DEXON [see J. Heller, Biomaterials 1 (1980), 51], poly(DL-lactide-co-ε-caprolactone), poly(DL-lactide-co-γ-valerolactone), poly(DL-lactide-co-γ-butyrolactone); polyalkyl-cyanoacrylates; polyamides, polyhydroxybutyrate; polydioxanone; poly-β-aminoketones [see Polymer 23, pp 1693-1697, (1982)]; polyphosphazenes [see Science, 193, (4259), 1214-19, (1976)] and polyanhydrides.

The microballoons of the present invention can also be prepared according to the methods disclosed in WO 96/15815, incorporated herein by reference, where the microballoons are made from a biodegradable membrane comprising biodegradable lipids, preferably selected from mono-di-, tri-glycerides, fatty acids, sterols, waxes and mixtures thereof. Preferred lipids are di- or tri-glycerides, e.g. di- or tri-myristin, -palmityn or -stearin, in particular tripalmitin or tristearin.

The microballoons may employ any of the gases disclosed herein or known to the skilled artisan for ultrasound techniques.

Any biocompatible gas may be used in the vesicular contrast agents of the invention. The term "gas", as used herein, includes any substance (comprehensive of mixtures thereof) substantially in gaseous form at the normal human body temperature.

The said gas may thus include, for example, air, nitrogen, oxygen, $CO_2$, argon, xenon, krypton, fluorinated gases (including, for example, perfluorocarbons, $SF_6$ or $SeF_6$) and low molecular weight hydrocarbons (for instance those containing from 1 to 7 carbon atoms including alkanes such as methane, ethane, propane, butane or pentane; cycloalkanes such as cyclopropane, cyclobutane or cyclopentane; alkenes or alkynes such as ethylene, propene, propadiene, butene, acetylene, propyne, and/or mixtures thereof). Fluorinated gases are however preferred.

Fluorinated gases include materials which contain at least one fluorine atom. Examples include, but are not limited to, compounds such as $SF_6$, freons (organic compounds containing one or more carbon atoms and fluorine such as $CF_4$, $C_2F_6$, $C_3F_8$, $C_4F_8$, $C_4F_{10}$, $CBrF_3$, $CCl_2F_2$, $C_2ClF_5$ and $CBrClF_2$) and perfluorocarbons. The term "perfluorocarbon" refers to compounds containing only carbon and fluorine atoms and include saturated, unsaturated and cyclic perfluorocarbons.

The saturated perfluorocarbons, which are preferred, have the formula $C_nF_{n+2}$, where n is from 1 to 12, preferably from 2 to 10, more preferably from 3 to 8 and even more preferably from 3 to 6. Suitable perfluorocarbons thus include, but are not limited to, $CF_4$, $C_2F_6$, $C_3F_8$, $C_4F_8$, $C_4F_{10}$, $C_5F_{12}$, $C_6F_{12}$, $C_7F_{14}$, $C_8F_{18}$ and $C_9F_{20}$. More preferably, the gas or gas mixture comprises $SF_6$ or a perfluorocarbon selected from the group consisting of: $C_3F_8$, $C_4F_8$, $C_4F_{10}$, $C_5F_{12}$, $C_6F_{12}$, $C_7F_{14}$, $C_8F_{18}$, with $C_4F_{10}$ being particularly preferred.

In certain circumstances it may be desirable to include a precursor to a gaseous substance, that is a material capable of being converted to a gas in vivo, often referred to as a "gas precursor". Preferably, the gas precursor and the gas it produces are physiologically acceptable. The gas precursor may be pH-activated, photo-activated, temperature-activated, and the like. For example, certain perfluorocarbons may be used as temperature-activated gas precursors. These perfluorocarbons, for instance perfluoropentane, have a liquid/gas phase transition temperature above room temperature (or the temperature at which the agents are produced and/or stored) but below body temperature; thus, they undergo a phase shift and are converted to a gas within the human body.

As above reported, also in the case of ultrasound contrast agents of the invention and of lipidic or phospholipidic precursor thereof, conjugation labelling may occur through properly reactive functional groups, either directly between the moieties involved or by means of a suitable linker.

Further Macromolecular Aggregates for Diagnostic Imaging

Having described the compounds of the invention as also comprising the residues of the metalloproteases inhibitors of formula (I) properly labelled with a variety of lipidic or phospholipidic components that enable, by working according to conventional methods, the preparation of liposomes for ultrasound imaging purposes, an additional embodiment of the invention is also represented by the above liposomes, micellar systems, vesicles, microspheres or microballoons, entrapping other imaging moieties among those previously disclosed.

We thus refer, according to an additional embodiment of the invention, to a macromolecular system for use in MRI imaging techniques comprising the above liposomes, micellar systems, vesicles, microspheres or microballoons, being prepared according to conventional methods by starting from the compounds comprising the residue of a metalloproteases inhibitor of formula (I) properly labelled with a lipidic or phospholipidic component as set forth above, and wherein within the cavity of the said liposomes, micellar systems, vesicles, microspheres or microballoons, there are incorporated suitably chelated MRI paramagnetic metal ions.

As far as the liposomes (or vesicles, micellar systems, microspheres, microballoons and the like), the chelating ligands and the paramagnetic metal ions are concerned, see the above reported details.

Preferably, an additional object of the invention is thus represented by the liposomes obtained from the metalloproteases inhibitor of formula (I) labelled with lipidic or phospholipidic components, and wherein the inner cavity of the said liposomes comprises the aforementioned chelate complexes of $Gd^{3+}$ ions.

Furthermore, and according to a still additional embodiment of the invention, there are novel diagnostic imaging agents which are highly selective towards given metalloproteases and that comprise suitable liposomes formed from the metalloproteases inhibitors of formula (I) labelled with lipidic or phospholipidic components, and wherein the inner cavity of the said liposomes comprises chelated ligands of lanthanide ions for MRI purposes.

The said liposomial imaging agents are characterized by an enhanced sensitivity over traditional MRI contrast agents as they may take advantage of the difference in NMR (Nuclear Magnetic Resonance) signal intensity of water protons in the presence and in the absence of the contrast agent, when a radiofrequency is applied, the said radiofrequency corresponding to the resonance frequence of water protons exchangeable by the system, that is inside and outside the liposomial vesicle.

Such a known technology of contrast amplification is better known as Chemical Exchange Saturation Transfer (CEST) and the materials suitable for the said technology are better known as LIPOCEST, hence of chelated complexes of lanthanide ions entrapped within liposomial vesicles that, according to the present invention, are labelled with a plurality of metalloproteases inhibitors of formula (I).

With the term LIPOCEST, as used herein, we thus intend a liposome that acts as a CEST agent (LIPOCEST agent) for use in CEST imaging protocols.

With CEST imaging, more in particular, we relate to the generation of contrast in MRI imaging techniques through the irradiation of mobile protons, in a CEST contrast agent containing at least one mobile proton in exchange with water or in a suitable CEST imaging system. In the present invention, the CEST imaging system is represented by a liposomal system. In this case, the chemical shift of the intraliposomal water protons which must be irradiated to observe saturation transfer has been suitably "shifted" as a result of their interaction with a paramagnetic chelate containing a lanthanide metal ion.

The paramagnetic complex can be encapsulated in the aqueous cavity of the liposome (if hydrophilic), and/or incorporated in the lipidic bilayer of the membrane (if amphiphilic).

The chemical shift difference between the resonances of intraliposomal and bulk water protons ($\Delta^{LIPO}$) is dependent on the formulation and preparation of the liposomes as well as on the physico-chemical properties of the paramagnetic complex. In particular, the chemical shift of the water proton is affected by: i) the concentration of the hydrophilic paramagnetic complex in the aqueous cavity (if encapsulated) and/or the concentration of the paramagnetic complex incorporated in the membrane and facing the aqueous inner cavity of the liposome, and ii) the liposome shape.

For a general reference to CEST techniques and LIPOCEST(s) see, as an example, Angew. Chem. Int. Ed. 2007, 46, 966-968; and Chem. Commun., 2008, 600-602.

Having defined the liposomal molecular aggregates of the invention as comprising a plurality of metalloproteases inhibitors of formula (I) suitably appended on the outer surface of the liposomes themselves, the said liposomes being intended for ultrasound imaging techniques, or MRI or MRI-CEST imaging techniques, additional imaging agents are herewith provided taking advantage of the well known interactions occurring between biotin or biotinylated molecules or moieties with avidin or streptavidin systems.

Therefore, those skilled in the art may well understand that the above macromolecular aggregates of the invention may be equally obtained by connecting a macromolecular liposomal system (including vesicles, microspheres, microballons, micelles and the like) and bearing a plurality of avidin or streptavidin moieties on its outer surface with a plurality of biotinylated targeted derivatives of the metalloproteases inhibitors of formula (I).

Hence, according to a further object of the invention, there are provided compounds comprising the residue of a metalloproteases inhibitor of formula (I) suitably labelled with one or more biotin or biotinylated residues.

For a general reference to the above multifunctionalized system see, as an example, Sipkins, D. A. et al., 1998, at. Med. 4:623-626 and references cited therein.

From all of the above, it should be clear to the skilled person that the above list of possible imaging or radiotherapeutic agents of the invention, together with precursors thereof, are not to be intended as limiting examples.

Included within the scope of the invention, in fact, are also all of the derivatives providing useful probes for imaging techniques, the said probes comprising one or more of the residues of the metalloproteases inhibitors of formula (I) suitably conjugated, either as such or through suitable linkers, with a variety of particles or entities known to generate detectable substances, for instance including: a) colloidal metal nano-particles, either coated with an organic outer layer or uncoated, e.g. gold nanoparticles or supermagnetic iron-oxide nanoparticles; b) Solid Lipid Nanoparticles (SLN) comprising complexes of paramagnetic metal ions or radionuclides; c) high density lipoprotein-like nanoparticles uploaded with amphiphilic metal ion complexes of paramagnetic atoms or radionuclides (see, for a reference, J. C. Frias et al., J. Am. Chem. Soc., 2004, 126, 16316); d) liposomes coated with micelles uploading complexes of paramagnetic metal ions or radionuclides (see, for a reference, WO 2005/117832); e) quantum dots with a lipidic coating uploaded with metal ion complexes exposed at the outer surface, the said metal ions being paramagnetic or radionuclide ions (see, for a reference, W. J. M. Mulder et al. Nano Lett., 2006, 6, 1-6).

According to a preferred embodiment of the invention, however, herewith provided are imaging or radiotherapeutic agents comprising the residue of one or more metalloproteases inhibitors of formula (I), the same or different from each other, properly labelled with one or more optically active imaging moieties or with one or more complexes of paramagnetic metal ions for MRI imaging or of radionuclides for radioimaging or radiotherapy.

Even more preferably, within this class, are imaging agents comprising the residue of a metalloproteases inhibitor of formula (I) properly labelled with an optically active imaging moiety or with a paramagnetic metal ion complex for MRI imaging.

Still more preferably, the optically active imaging moiety is a fluorescent molecule selected from fluorescin, 5-carboxyfluorescein, indocyanine green, Cy5, Cy5.5 and derivatives thereof including, for instance, Cy5.5 mono NH ester or Cy5.5 bis NHS ester; and the paramagnetic metal ion complex for MRI imaging is selected from gadolinium ($Gd^{3+}$) complexes DOTA, AAZTA, EDTA, TETA, DTPA, and derivatives thereof including, for instance, DTPA-Glu and DTPA-Lys.

Linkers

As formerly reported, the imaging moiety or moieties according to the present invention and, by extension, any of the moieties including radiotherapeutics or even precursors thereof such as lipidic, phospholipidic or polymeric components, as well as biotin or biotinylated residues, are all attached to the metalloproteases inhibitors of formula (I) either directly or through any suitable linker, otherwise referred to as spacer.

If present, besides acting as a linking group, the linker may also provide for a proper distance between these moieties.

In this respect, an optimal distance between these units may represent an important factor so as to get and maintain the targeting capability of the compounds of the invention towards metalloproteases. In fact, any improper or anyway sub-optimal derivatization of the sulphonamido-based targeting moiety may result in a significant loss of the affinity of the diagnostic probe for the targeted objective.

In addition, the above linker(s) may significantly contribute to improve the hydrophilicity of the diagnostic imaging agent, thus providing the desired pharmacokinetic or pharmacodynamic profile of the obtained labelled derivative.

According to the present invention, the linker is a linear or branched, at least divalent, linking moiety.

With the terms "divalent linking moiety" or "divalent linking chain" or even "divalent linker", as used herein interchangeably, we intend a chain including two functional groups allowing for their conjugation with a suitable functional group of the metalloproteases inhibitor of formula (I), at one side, and with a suitable functional group of the imaging moiety, at the other side.

Unless otherwise indicated, whit the term "functional group", as used herein, we refer to specific groups of atoms, within molecules or moieties, that are responsible for the characteristic chemical reaction of those molecules or moieties.

In the context of the present invention, examples of functional groups allowing for the above conjugation may comprise primary and secondary amino groups (—$NH_2$, >NH), hydroxy groups (—OH), carboxy groups (—$CO_2H$), sulphonamido groups (—$SO_2NH_2$ or —$SO_2NH$—), hydroxamic groups (—CONHOH), phosphonic groups [—PO(OH)2], thiol groups (—SH), and the like.

Particularly preferred, among them, are amino and carboxy groups so as to give rise to carboxamido linkages.

In addition to the above, these same linkers may optionally comprise additional functional groups not taking part to the conjugation with the rest of the molecule, that may be present either as such or as optionally protected groups.

According to an additional embodiment of the invention, the linker may be also represented by a linear or branched polyfunctional linking moiety.

Unless otherwise provided, with "polyfunctional linking moiety" or even "polyfunctional linker", as used herein interchangeably, we intend a linear or branched chain including at least 3 functional groups among those above reported, the said groups being responsible for the conjugation of labelling with any one of the metalloproteases inhibitors of formula (I) and the imaging moieties.

Suitable examples of the said polyfunctional chains may thus include, for instance:

(a) N-branched lysine systems [see, for a reference, Veprek, P et al., J. Pept. Sci. 5, 5 (1999); 5, 203 (1999)];

(b) polycarboxylic compounds and suitable derivatives thereof in which the carboxylic group(s) are in a suitably activated or protected form;

(c) polyaminated compounds and suitable derivatives thereof in which the amino group(s) are in a suitably activated or protected form;

(d) amino acids and poly-amino acids such as polyornithine, polyarginine, polyglutamic acid, polyaspartic acid, and the like.

Whether divalent or polyvalent, the linker may include, without limitations: substituted or unsubstituted, either saturated or unsaturated, straight or branched alkylene chains; amino acids and peptides from straight, branched or cyclic amino acids; derivatized or underivatized polyethylene glycol, polyoxyethylene or polyvinylpyridine chains; substituted or unsubstituted polyamide chains; derivatized or underivatized polyamine, polyester, polyethylenimine, polyacrylate, poly(vinylalcohol), polyglycerol, or oligosaccharide (e.g., dextran) chains; glycosylated amino acid residues, alternating block copolymers; malonic, succinic, glutaric, adipic and pimelic acids; caproic acid; simple diamines and dialcohols; any of the other linkers disclosed herein as well as any other simple polymeric linker known in the art, for instance as described in WO 98/18497 and WO 98/18496.

Preferably, the said linking moiety comprises a straight or branched $C_1$-$C_{20}$ alkylene chain, optionally substituted and/or interrupted by one or more groups selected from arylene or heteroarylene rings, cycloaliphatic or heterocyclic rings, —O—, —CO—, —CONH—, —NHCO—, —NH—, >NCO—, —OCN< or —N<.

Furthermore, the linkers of the invention may be defined as:

homobifunctional (for instance: —HN-chain-NH— or —CO-chain-CO—), or heterobifunctional (for instance: —HN-chain-CO— or —CO-chain-HN—)

whether bearing, at their sites of conjugation, the same or different reactive functional groups, respectively.

Suitable examples of linkers are those reported below, which formulae are comprehensive of the reactive functional groups allowing for the conjugation reaction:

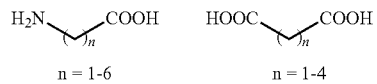

n = 1-6     n = 1-4

-continued

HOOC~(~O~)ₙCOOH    H₂N~(~)ₙNH₂
n = 1-3              n = 2-6

H₂N~(~O~)ₙNH₂
n = 1-5

*Tetrahedron Lett.* 1998, 39, 6277;
*Makromol. Chem.* 1979, 180, 2539.

H₂N~O~O~O~NH₂

H₂N~O~O~NH₂

H₂N~(~O~)ₙCOOH
n = 1-4

*J. Org. Chem.* 2001, 66, 4799;
*Org. Prep. Proced. Int.* 2002, 34, 326

H₂N~(~O~)ₙCOOH
n = 1-6

*Bioconjugate Chem.* 1999, 10, 1021.

H₂N–C₆H₄–COOH

H₂N–CH₂–C₆H₄–COOH

H₂N–CH₂–C₆H₄–CH₂COOH

HOOC–C₆H₄–COOH

HOOC–C₆H₃(COOH)–COOH

HOOC—(CH₂)₃—NHCO–C₆H₄–CONH—(CH₂)₃—COOH

H₂N–C₆H₁₀–COOH

H₂N–CH₂–C₆H₁₀–COOH

H₂N–(CH₂)₂–O–C₆H₄–COOH

H₂N–CH₂–C₆H₄–O–CH₂COOH piperidine-4-carboxylic acid

-continued maleimido-CH₂CH₂-NH₂

*Bioconjugate Chem.* 1990, 1, 431 maleimido-CH₂CH₂-O-CH₂CH₂-NH₂

*Bioconjugate Chem.* 1990, 1, 431 maleimido-(CH₂)ₙ-COOH
n = 0-3 maleimido-CH₂CH₂-O-CH₂CH₂-O-CH₂COOH

*Bioconjugate Chem.* 1996, 7, 180

HS~(~)ₙCOOH
n = 0-1

HS~O~O~COOH

*Bioconjugate Chem.* 1996, 7, 180

HS~O~O~NH₂

*Tetrahedron* 1997, 53, 10939

HS~NH₂

HOOC—CH₂—CH(NH₂)COOH

HOOC—(CH₂)₂—CH(NH₂)COOH

HOOC—(CH₂)₃—CH(NH₂)COOH

H₂N—CH₂—CH(NH₂)COOH

H₂N—(CH₂)₂—CH(NH₂)COOH

H₂N—(CH₂)₃—CH(NH₂)COOH

H₂N—(CH₂)₄—CH(NH₂)COOH

HOOC—(CH₂)₂—CON[(CH₂)₂NH₂]₂

WO 04/065407

HOOC—CH₂—N[(CH₂)₃NH₂]₂    C(CH₂—COOH)₄

C(CH₂—NH₂)₄

H₂N—(CH₂)₂—O–C₆H₃(O—(CH₂)₂—NH₂)–COOH

-continued

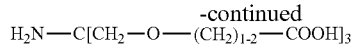

*Synth. Commun.* 2001, 31, 1307;
*Org. Prep. Proced. Int.* 1996, 28, 49;
*J. Am. Chem. Soc.* 2002, 124

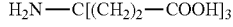

*Synth. Commun.* 2001, 31, 1307;
*Org. Prep. Proced. Int.* 1996, 28, 49;
*J. Am. Chem. Soc.* 2002, 124

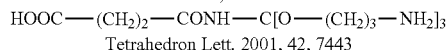

Tetrahedron Lett. 2001, 42, 7443

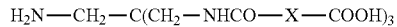

X = —CH$_2$—CH$_2$—, —CH$_2$—O—CH$_2$—,
—(CH$_2$—O—CH$_2$)$_3$—

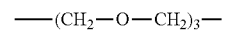

U.S. Pat. No. 5,514,810

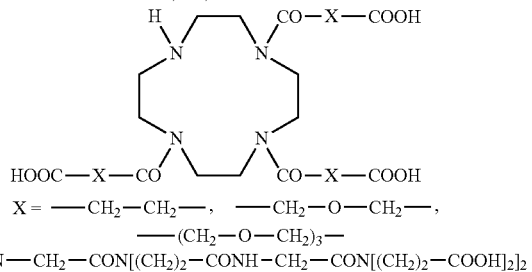

X = —CH$_2$—CH$_2$—, —CH$_2$—O—CH$_2$—,
—(CH$_2$—O—CH$_2$)$_3$—

H$_2$N—CH$_2$—CON[(CH$_2$)$_2$—CONH—CH$_2$—CON[(CH$_2$)$_2$—COOH]$_2$]$_2$

Tetrahedron Lett. 2005, 46, 1463

EP 1259532          EP 1259532

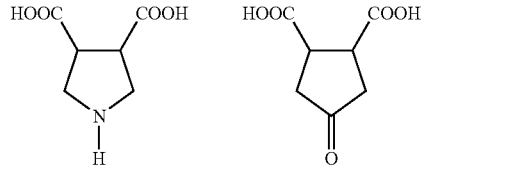

EP 1259532          EP 1259532

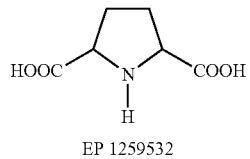

NH$_2$
EP 1259532

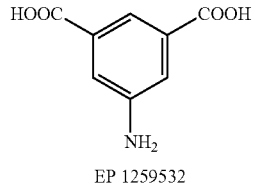

EP 1259532

HOOC—CH$_2$—CH(CH$_2$—NH$_2$)$_2$
EP 1259532

Most of the linkers are known and commercially available whilst other may be prepared according to well known methods, for instance as per the accompanying bibliographic references.

From all of the above, it should be clear to the skilled person that the above linkers, for instance those related to lysine, 2,3-ornithine or even to 2,3-diaminopropionic acid and derivatives thereof, may be serially employed to elongate and/or suitably increase the multiplicity of the moieties thus attached.

Additionally, the linker may be also represented by or anyway comprise a streptavidin or an avidin/biotin system.

Points of Attachment

Whether or not in the presence of a linker moiety, preferred points of attachment within the metalloproteases inhibitors of formula (I) are those represented by groups:

R, when R is a group of formula (II) being suitably substituted by reactive functional groups allowing for the conjugation with the rest of the molecule (e.g. carboxy or amino);

$R_1$, for instance when $R_1$ itself is hydrogen or when it represents a group —Ra or —ORa as formerly reported, the said group being substituted by the aforementioned reactive functional groups (e.g. carboxy, amino or even heterocyclic rings like piperazino);

any of $R_2$ and $R_3$, for instance when representing a carboxy group; and

G, for instance when representing the group —(CH$_2$)$_m$—N(R$_4$)(R$_5$) with any of $R_4$ and/or $R_5$ being a hydrogen atom or a heterocyclic group bearing the aforementioned reactive functional groups.

From all of the above, and according to a preferred embodiment of the invention, the residues of the metalloproteases inhibitors of formula (I) are selected from the group consisting of:

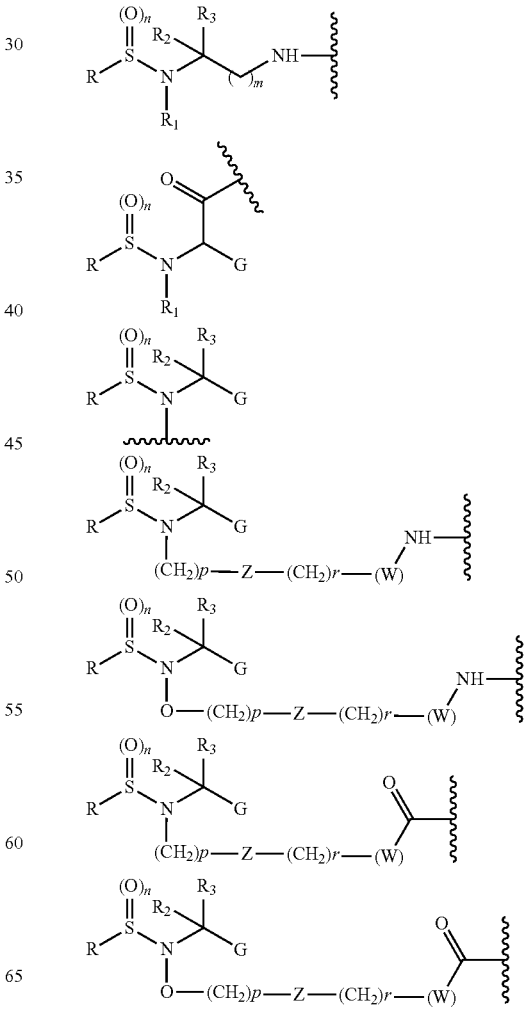

-continued

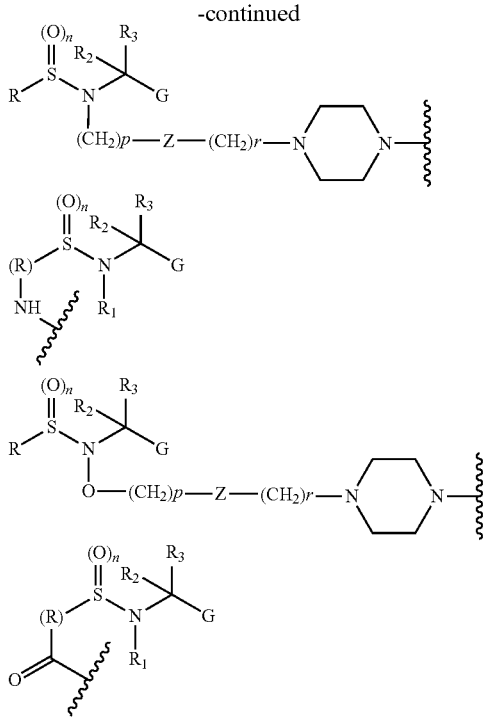

wherein R, n, R$_1$, R$_2$, R$_3$, m, G, p, Z, r and W are as above reported, and the line ∼∼∼ represents the point of attachment with the rest of the molecule.

As formerly reported, the agents or compounds of the invention can also be present in the form of pharmaceutically acceptable salts.

The term "pharmaceutically acceptable salt", as used herein, refers to derivatives of the compounds of the invention wherein the parent compound is suitably modified by converting any of the free acidic or basic groups, if present, into the corresponding addition salts with any base or acid conventionally intended as being pharmaceutically acceptable.

Apart from being non-toxic, the corresponding salts of the compounds of the invention are also characterized by a high stability, including a physiological stability upon usage and administration.

Suitable examples of the said salts may thus include mineral or organic acid addition salts of basic residues such as amino groups, as well as mineral or organic basic addition salts of acidic residues such as carboxylic, phosphonic or sulphuric groups.

Preferred cations of inorganic bases which can be suitably used to prepare salts within the invention comprise ions of alkali or alkaline-earth metals such as potassium, sodium, calcium or magnesium. Preferred cations of organic bases comprise, inter alia, those of primary, secondary and tertiary amines such as ethanolamine, diethanolamine, morpholine, glucamine, N-methylglucamine, N,N-dimethylglucamine.

Preferred anions of inorganic acids which can be suitably used to salify the compounds of the invention comprise the ions of halo acids such as chlorides, bromides, iodides or other suitable ions such as sulfates.

Preferred anions of organic acids comprise those routinely used in pharmaceutical techniques for the salification of basic substances such as, for instance, acetate, trifluoroacetate, succinate, citrate, fumarate, maleate or oxalate.

Preferred amino acids that can be suitably used to salify the compounds of the invention may also comprise, for instance, taurine, glycine, lysine, arginine, ornithine, aspartic and glutamic acid.

Specific examples of the compounds of the invention, together with the process for their preparation, are reported in the following experimental section.

The process for the preparation of the compounds of the invention may be carried out according to conventional methods well known to those skilled in synthetic organic chemistry techniques.

Preferably, the said preparation process comprises at first preparing the metalloproteases inhibitor of formula (I) and, then, subsequently subjecting it to a conjugation reaction with the selected labelling moiety.

The said process thus comprises:

a) reacting a compound of formula (IV) with a compound of formula (V)

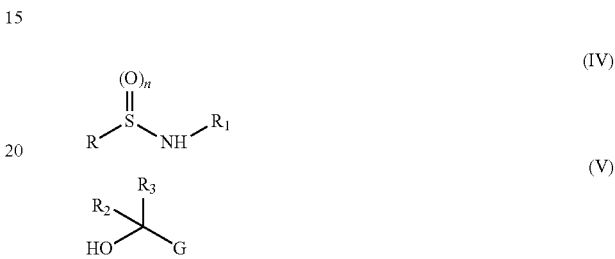

wherein R, R$_1$, R$_2$, R$_3$, G and n have the above reported meanings so as to obtain a compound of formula (I); and, optionally b) converting the compound of formula (I) being obtained in step (a) into another compound of formula (I) and/or into a pharmaceutically acceptable salt thereof;

c) conjugating a compound of formula (I) thus obtained in any of the steps (a) or (b) with the selected labelling moiety, either directly or through a suitable linker.

The above process is particularly advantageous as it is susceptible of being properly modulated, through any proper variant, so as to obtain any of the desired compounds of the invention.

In step (a) of the process, the reaction between the compounds of formula (IV) and (V) is carried out according to conventional methods for the preparation of sulphonamido or sulphinamido groups with n as 2 or 1, respectively.

Typically, the reaction is carried out under the known Mitsunobu condensation operative conditions, in the presence of suitable solvents including, among others, tetrahydrofuran, dichloromethane, acetonitrile, N-methylpyrrolidone, benzene, toluene, m-xylene, and mixtures thereof.

In this respect, the above reaction may take place in the presence of a suitable condensing agent, either as such or suitably supported onto polymeric resins and including, for instance, diethyl azodicarboxylate (DEAD), diisopropylazodicarboxylate (DIAD), 1,1'-azodicarbonyldipiperidine (ADDP), N,N,N',N'-tetramethylazodicarboxamide (TMAD), triphenylphosphine (PPh$_3$), tributylphosphine (PBu$_3$), and the like.

From all of the above, it should be clear to the skilled person that, in step (a) of the process, any of the R, R$_1$, R$_2$, R$_3$ and G groups, hereinafter shortly referred to as "R" groups, may be present as such or, alternatively, may be present in any properly protected form.

More in particular, functional groups being present in any of the compounds of formula (IV) or (V) and which could give rise to unwanted side reactions and by-products, need to be properly protected before the condensation reaction takes place. Likewise, subsequent deprotection of those same protected groups may follow upon completion of the said reactions.

In the present invention, unless otherwise indicated, the term "protecting group", designates a protective group adapted to preserving the function of the group to which it is bound. Specifically, protective groups are used to preserve amino, hydroxyl or carboxyl functions. Appropriate protective groups may thus include, for example, benzyl, benzyloxycarbonyl, alkyl or benzyl esters, or other substituents commonly used for the protection of such functions, which are all well known to those skilled in the art [see, for a general reference, T. W. Green; Protective Groups in Organic Synthesis (Wiley, N.Y. 1981)].

Likewise, selective protection and deprotection of any of the said groups, for instance including carboxyl, hydroxyl and amino groups, may all be accomplished according to very well known methods commonly employed in organic synthetic chemistry.

In addition to the above, as per step (b) of the process, any of the "R" groups within the compounds of formula (I) that could be easily identified as a derivatized group, for instance any ester or amide, may be prepared from the functional groups from which it derives, by working according to conventional methods.

As a non limiting example, for instance in the case of the preparation of a compound of formula (I) wherein $R_2$ is a group —COORb, Rb is an alkyl group and $R_3$ is H, that same compound could be prepared according to the present process: (i) by starting from a compound of formula (V) wherein $R_2$ and $R_3$ are as above defined, as per step (a); or, alternatively, (ii) by starting from a corresponding compound of formula (I) wherein $R_2$ is —COOH, and by properly converting the carboxyl group into the desired —COORb group, as per step (b) of the process.

The above reaction conditions are well known in the art for the preparation of carboxylic esters.

Analogous considerations may apply, for instance, in the preparation of carboxamides by properly reacting the corresponding carboxyl derivative with any suitable amine, and by working according to well known operative conditions.

Likewise, for instance in the preparation of a compound of formula (I) wherein $R_2$ is the hydroxamic group —CONHOH, the process may be carried out by first reacting a compound of formula (I) wherein $R_2$ is carboxyl, being obtained in step (a), in the presence of suitable reactants like, for instance, O-(tert-butyldimethylsilyl)hydroxylamine, O-(tetrahydro-2H-pyran-2-yl)hydroxylamine, O-tritylhydroxylamine or O-benzylhydroxylamine, as the case may be.

Subsequent deprotection of the obtained intermediate derivative, for instance under acidic hydrolysis in the presence of trifluoroacetic acid or with trimethylsilyltriflate or by catalytic hydrogenation in the case of O-benzylhydroxylamine, may lead to the desired compound with $R_2$ as —CONHOH.

Several additional examples are known in the art as allowing to convert a given group within a compound of formula (I) into another group. They may comprise, for instance: the conversion of an amino (—NH$_2$) or carboxamido (—CONH$_2$) group into the corresponding N-substituted derivative; the conversion of a carboxyl group into the corresponding benzyl ester derivative, by reaction with benzylbromide in the presence of cesium carbonate, as per well known operative conditions; the conversion of a carboxyl group (—COOH) into the corresponding (—CONHSO$_3$H) group, by its first conversion into (—CONH$_2$) followed by reaction with chlorosulfonic acid in the presence of 2-picoline; the conversion of a carboxyl group (—COOH) into the corresponding [—CH$_2$PO(OH)$_2$] group, by its first reduction to hydroxymethyl (—CH$_2$OH), subsequent conversion into (—CH$_2$Cl) by means of thionyl chloride, followed by reaction with triethylphosphite to give the corresponding [—CH$_2$P(OH)$_2$] group finally hydrolyzed to [—CH$_2$PO(OH)$_2$].

All of the above reactions and operative conditions thereof are well known in the art and allow to obtain a variety of compounds of formula (I).

Clearly, also per step (b) of the process, any functional group within the compounds of formula (I) being obtained in step (a) and that could lead to undesired by-products, need to be properly protected before the reaction takes place, and then deprotected, according to known methods.

For a reference to the specific operative conditions being employed in the preparation of the compounds of formula (I) see, as an example, the following Scheme 1 that provides synthetic pathways for the preparation of representative compounds of the invention. Specific details, however, can be found in the experimental section.

Within the Scheme 1 below, it is reported the preparation of some representative compounds of formula (I) wherein n and m are both 2; R, $R_1$ and $R_4$ have the meanings therein reported, one of $R_2$ or $R_3$ is H and the remaining one of $R_2$ or $R_3$ is a carboxyl or hydroxamic group (—COOH or —CONHOH) and $R_5$ is H.

Scheme 1

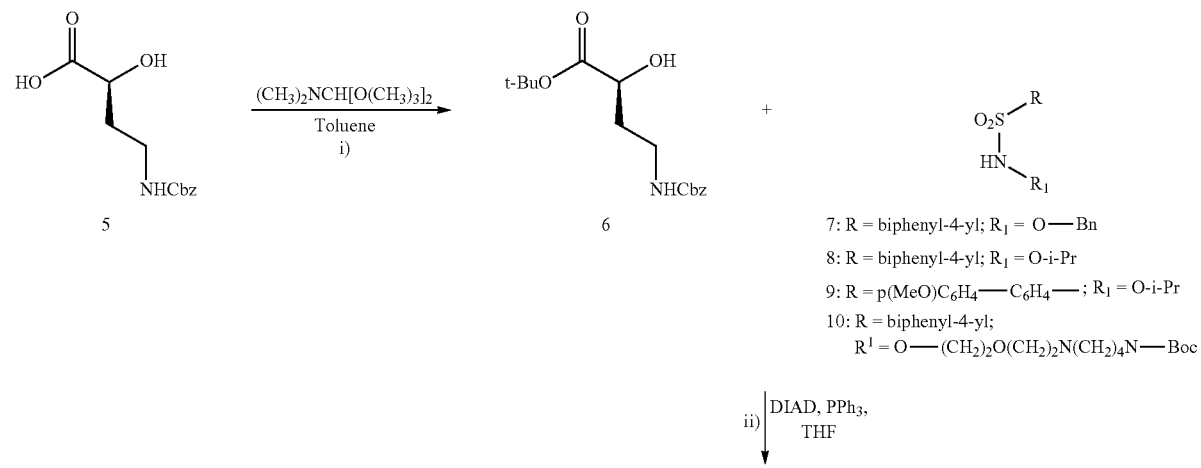

-continued

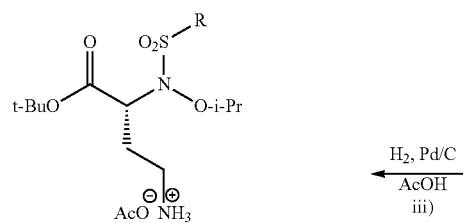

15: R = biphenyl-4-yl
16: R = p(MeO)C₆H₄—C₆H₅—

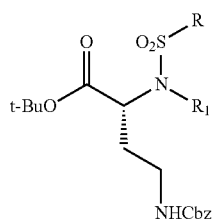

11: R = biphenyl-4-yl; R₁ = O—Bn
12: R = biphenyl-4-yl; R₁ = O-i-Pr
13: R = p(MeO)C₆H₄—C₆H₄—;
   R₁ = O-i-Pr
14: R = biphenyl-4-yl;
   R₁ = O—(CH₂)₂O(CH₂)₂N(CH₂)₄N—Boc H₂, Pd/C / AcOH  iii) ←

R₄Cl, i-Pr₂NEt, DMF  iv) ↓ iii′) TFA, CH₂Cl₂ ↓

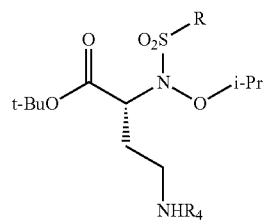

17: R = biphenyl-4-yl; R₄ = Benzoyl
18: R = biphenyl-4-yl; R₄ = Methanesulfonyl
19: R = biphenyl-4-yl; R₄ = Acetyl
20: R = biphenyl-4-yl; R₄ = Phenacetyl
21: R = p(MeO)C₆H₄—C₆H₄—; R₄ = Acetyl
22: R = p(MeO)C₆H₄—C₆H₄—; R₄ = Phenacetyl

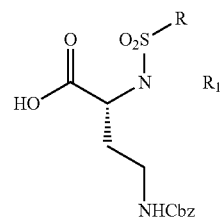

35: R = biphenyl-4-yl; R₁ = O—Bn
36: R = biphenyl-4-yl;
   R₁ = O—(CH₂)₂O(CH₂)₂N(CH₂)₄N—Boc TFA, CH₂Cl₂  v) ↓ iv′) TBDMSiONH₂, EDCI, CH₂Cl₂ ↓

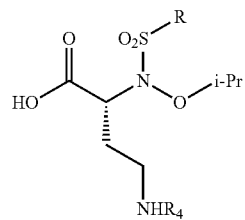

23: R = biphenyl-4-yl; R₄ = Benzoyl
24: R = biphenyl-4-yl; R₄ = Methanesulfonyl
25: R = biphenyl-4-yl; R₄ = Acetyl
26: R = biphenyl-4-yl; R₄ = Phenacetyl
27: R = p(MeO)C₆H₄—C₆H₄—; R₄ = Acetyl
28: R = p(MeO)C₆H₄—C₆H₄—; R₄ = Phenacetyl

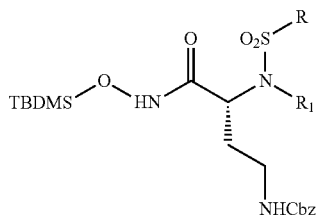

37: R = biphenyl-4-yl; R₁ = O—Bn
38: R = biphenyl-4-yl;
   R₁ = O—(CH₂)₂O(CH₂)₂N(CH₂)₄N—Boc TBDMSiONH₂, EDCI, CH₂Cl₂  vi) ↓ v′) TFA, CH₂Cl₂ ↓

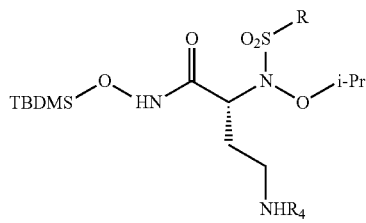 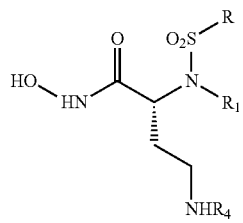

29: R = biphenyl-4-yl; R₄ = Benzoyl
30: R = biphenyl-4-yl; R₄ = Methanesulfonyl
31: R = biphenyl-4-yl; R₄ = Acetyl
32: R = biphenyl-4-yl; R₄ = Phenacetyl
33: R = p(MeO)C$_6$H$_4$—C$_6$H$_4$—; R₄ = Acetyl
34: R = p(MeO)C$_6$H$_4$—C$_6$H$_4$—; R₄ = Phenacetyl Essentially, the above preparation process comprises the steps of:
i) protecting the carboxyl group of compound (5) with any suitable protecting group, for instance with N,N-dimethylformamide di-tert-butyl acetal in toluene (see, as a general reference, Rossello et al. *Bioorg. Med. Chem. Lett*, 2005, 15, 1321), thus providing the compound of formula (6);
ii) reacting any one of the compounds (7-10) with the compound of formula (6) by working according to well known Mitsunobu operative conditions, for instance in the presence of diisopropylazodicarboxylate (DIAD) and triphenylphosphine (PPh₃) as condensing agents, in a suitable solvent like tetrahydrofuran, thus obtaining the corresponding compounds of formula (11-14); and processing them as per the alternative pathways below:
iii) deprotecting the amino group of the compounds (12-13) according to conventional methods including, for instance, catalytic hydrogenation with palladium or platinum catalysts in acetic acid, so as to obtain the compounds (15-16);
iv) properly functionalizing the amino group of compounds (15-16) so as to get any desired —NHR₄ group, as per compounds (17-22), for instance through reaction with any suitable acylating agent;
v) deprotecting the carboxylic function so as to get the corresponding compounds (23-28) under suitable hydrolysis conditions, for instance in the presence of trifluoroacetic acid and in a suitable solvent like dichloromethane;
vi) converting that same carboxylic group of compounds (23-28) into a suitable silyl derivative (29-34) according to known methods, for instance by means of O-(tert-butyldimethylsilyl)hydroxylamine in dichloromethane, followed by the addition of 1-[3-(dimethylamino)propyl]-3-ethyl carbodiimide;
vii) and hydrolysing compounds (29-34), for instance with trifluoroacetic acid in dichloromethane, so as to lead to the desired compounds of formula (I);
or, alternatively
iii') deprotecting the carboxylic function of compounds (11 and 14) so as to obtain the compounds (35 and 36), for instance by working as per step (v);
iv') converting the compounds thus obtained to the corresponding silyl derivatives (37-38), for instance by working as per step (vi);
v') and hydrolysing compounds (37-38), for instance by working as per step (vii), thus obtaining the desired compounds of formula (I).

Alternative methods for hydroxamate synthesis, under mild conditions, are reported in scheme 1 BIS, below:

Scheme 1 BIS

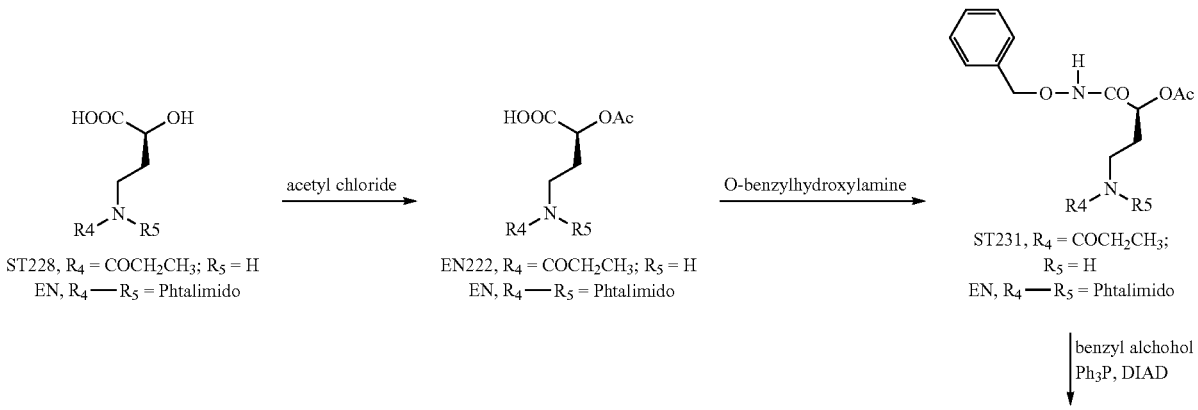

ST228, R₄ = COCH₂CH₃; R₅ = H
EN, R₄—R₅ = Phtalimido

EN222, R₄ = COCH₂CH₃; R₅ = H
EN, R₄—R₅ = Phtalimido

ST231, R₄ = COCH₂CH₃;
R₅ = H
EN, R₄—R₅ = Phtalimido benzyl alchohol
Ph₃P, DIAD

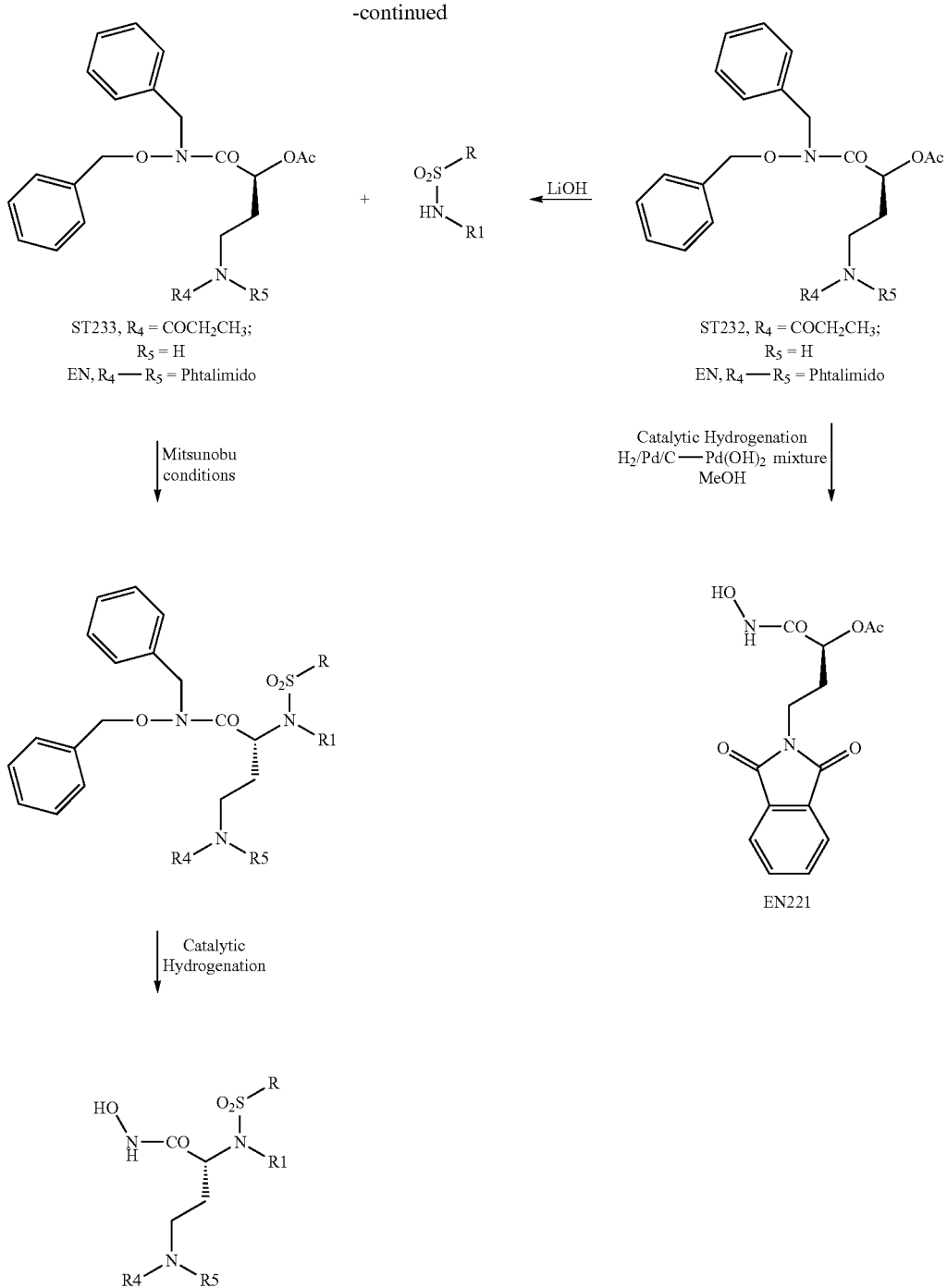

Once obtained, the selected metalloproteases inhibitor of formula (I) is then labelled so as to give rise to the compounds of the invention.

Labelling occurs by properly reacting, according to known methods, a metalloproteases inhibitor of formula (I) bearing, in the aforementioned positions of attachment with the rest of the molecules, suitable reactive functional groups, for instance comprising amino, hydroxy, carboxy, sulphonamido, hydroxamate, phosphonic or thiol groups, with the rest of the molecule.

The above conjugation reaction may be carried out according to a variety of methods known in the art, for instance in the presence of suitably activating coupling agents, so as to give rise to the corresponding conjugated compound of the invention, for instance carboxamides, properly labelled with the desired moiety.

Analogous considerations apply when the metalloproteases inhibitor of formula (I) is first reacted with a suitable linker and, then, the obtained compound is reacted with the selected labelling moiety or, alternatively, the labelling moiety is first conjugated with a linker and the obtained compound is suitably coupled to the metalloproteases inhibitor of formula (I).

Analogous considerations also apply in case of a plurality of metalloproteases inhibitors of formula (I), for instance conjugated with a polyfunctional linker also comprising a reactive functional group allowing for the labelling with an imaging moiety.

In this respect, a first metalloproteases inhibitor will be reacted with a suitable linker and the thus obtained derivative will be then reacted with another metalloproteases inhibitor, the former and the latter being the same or different from each other. Because of the presence of the additional reactive functional group within the linker, the resultant compound may be then reacted with the selected imaging or radiotherapeutic moiety.

Additional variations, for instance in the order of conjugation reactions occurring between the moieties may apply as well.

Clearly, any functional group being present in any of the moieties of the metalloproteases inhibitor, of the labelling moiety or of the optional linker, and not taking part to the above conjugation reactions, may be suitably protected so as to avoid the formation of unwanted side products and finally deprotected, according to known methods.

Finally, optional salification of the compounds of the invention may be carried out by properly converting any of the free acidic groups (e.g. carboxylic, sulforic, phosphonic and the like) or free amino groups into the corresponding pharmaceutically acceptable salts. In this case too, the operative conditions being employed for the optional salification of the compounds of the invention are all within the ordinary knowledge of the skilled person.

From all of the above, it should be clear to the skilled person that the above process, comprehensive of any variant thereof for the preparation of suitable compounds of the invention, may be conveniently modified so as to adapt the reaction conditions to the specific needs, for instance by choosing appropriate condensing agents, solvents and protective groups, as the case may be.

The compounds of formula (IV) and (V), as starting materials of the present process, are known or can be easily prepared according to known methods.

The sulphonamido derivatives of formula (IV), for instance, may be prepared by reacting any suitable amino compound with any suitable sulphonyl chloride derivative, substantially as follows:

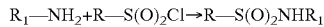

$R_1$—$NH_2$ + R—$S(O)_2Cl$ → R—$S(O)_2NHR_1$

Likewise, if not known per se, both the above amine and the sulphonyl chloride derivative may be easily prepared according to known methods from commercially available compounds.

Analogous consideration may apply to the compounds of formula (V) that, if not commercially available per, se may be conveniently prepared according to conventional methods well known in the art.

Finally, as far as the linker and the labelling moieties are concerned, they are all known or can be prepared according to known methods.

In this respect, when the compounds of the invention comprise labelling moieties for MRI, for radionuclide imaging or even for radiotherapy, thus including suitably chelated complexes of metal ions among those formerly reported, their preparation may first comprise obtaining the metalloproteases inhibitor of formula (I) labelled with the selected chelating unit or units and, then, preparing the desired chelated complex or complexes with the proper metal of choice, according to known methods.

For example, the paramagnetic complexes of the invention and, particularly, the Gd(III) chelates may be prepared by stoichiometric addition of suitable Gd(III) derivatives, particularly Gd(III) salts or oxides. See, for instance, EP 230893 disclosing labelling with paramagnetic metal ions, and WO 98/52618, U.S. Pat. No. 5,879,658, and U.S. Pat. No. 5,849,261 disclosing labelling with radioactive metals.

In forming a complex of radioactive technetium, for instance, a technetium complex, preferably a salt of $^{99m}$Tc pertechnetate, is reacted with the unlabelled compounds of the invention in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of the compound of the invention to be labelled and a sufficient amount of reducing agent to label the reagent with $^{99m}$Tc. Alternatively, the complex may be formed by reacting a compound of the invention, which is conjugated with an appropriate chelating moiety, with a pre-formed labile complex of technetium in the presence of an additional compound known as a transfer ligand. This latter process is known to those skilled in the art as ligand exchange process. The labile complex may be formed using transfer ligands such as, for instance, tartrate, citrate, gluconate or mannitol.

Among the $^{99m}$Tc pertechnetate salts useful with the present invention are included the alkali metal salts such as the sodium salt, or ammonium or lower alkyl ammonium salts. The preparation of the complexes of the invention where the metal is radioactive rhenium may be accomplished by using, as starting materials, rhenium compounds wherein the metal is in the +5 or +7 oxidation state. Examples of compounds in which rhenium is in the Re(VII) state are $NH_4ReO_4$ or $KReO_4$. Re(V) is available, for example, as [$ReOCl_4$](NBu$_4$), [$ReOCl_4$](AsPh$_4$), $ReOCl_3$(PPh$_3$)$_2$ and as $ReO_2$(pyridine)$_4^+$ (Ph is phenyl; Bu is n-butyl). Other rhenium reagents capable of forming a rhenium complex may also be used.

Radioactively-labelled scintigraphic imaging agents provided by the present invention must contain a suitable amount of radioactivity. In forming $^{111}$In or $^{99m}$Tc complexes, it is generally preferred to form radioactive complexes in solutions containing radioactivity at concentrations of from about 0.01 millicurie (mCi) to 100 mCi per mL.

The compounds of the invention find a variety of applications in the diagnostic field and, also, in therapy when the labelling moiety is a radiotherapeutic moiety.

In particular, they may find advantageous application for localizing, measuring and detecting pathological conditions associated with a non-physiological overexpression of metalloproteases, as well as for evaluating and monitoring therapeutic effect of drugs being administered to treat the above pathological conditions.

The compounds of the invention have a wide range of applications as they can be used for intravasal, (for instance intravenous, intraarterial, intracoronaric, intraventricular administration and the like), intrathecal, intraperitoneal, intralymphatic and intracavital administrations. Furthermore, they are suitable for the oral or parenteral administration and, therefore, specifically for the imaging of the gastrointestinal tract.

In a preferred embodiment thereof, there are provided pharmaceutical compositions containing, as active ingredient, at least one compound of the invention, including pharmaceutically acceptable salts thereof, in combination with one or more pharmaceutically acceptable carriers or excipients.

Compositions for the desired route of administration can be prepared by any of the methods well known in the art. Details concerning dosages, dosage forms, modes of administration, compositions and the like are further discussed in a standard pharmaceutical text, such as Remington's Pharmaceutical Sciences, 18th ed., Alfonso R. Gennaro, ed. (Mack Publishing Co., Easton, Pa. 1990), which is hereby incorporated by reference.

For instance, for parenteral administration they can be preferably formulated as sterile aqueous solutions or suspensions, whose pH can range from 6.0 to 8.5.

These aqueous solutions or suspensions can be administered in concentrations ranging between 0.002 and 1.0 M. These formulations can be lyophilized and supplied as they are, to be reconstituted before use.

For the gastrointestinal use or for injection in the body cavities, these agents can be formulated as a solution or suspension optionally containing suitable excipients in order, for example, to control viscosity.

For the oral administration they can be formulated according to preparation methods routinely used in the pharmaceutical technique or as coated formulations to gain additional protection against the stomach acidic pH thus preventing, in case of chelated metal ions, their release which may take place particularly at the typical pH values of gastric fluids.

Other excipients, for example including sweeteners and/or flavouring agents, can also be added, according to known techniques of pharmaceutical formulations.

The solutions or suspensions of the compounds of this invention can also be formulated as aerosol to be used in aerosol-bronchography and instillation.

For example, they can be also encapsulated into liposomes or even constitute the liposomes themselves, as set forth above, and thus can be used as uni- or multi-lamellar vesicles.

Preferably, a suitable pharmaceutical composition according to the invention is formulated in accordance with routine procedures as a pharmaceutical composition adapted for intravenous administration to human being.

For example, the contrast agents of the invention, for use in optical imaging or MRI techniques, are administered to the patient in the form of an injectable composition. The method of administering the said contrast agent is preferably parenthenally, meaning intravenously, intraarterially, intrathecally, interstitially, or intracavitarilly. For instance, for MRI, it is contemplated that the subject will receive a dosage of contrast agent sufficient to enhance the MR signal at the target (e.g., a site wherein overexpression of metalloproteases may occur) at least 10%. After injection of the targeted MRI contrast agent of the invention, the patient is scanned in the MRI machine to determine the location of any site containing the target. In therapeutic settings, upon target localization, a cytotoxic or therapeutic agent can be immediately administered, if necessary, and the patient can be subsequently scanned to visualize the therapeutic effect.

Substantially analogous considerations apply when administering optical imaging contrast agents of the invention to detect tissues and body areas overexpressing metalloproteases, thus indicating possible pathological conditions or inflammatory states, for instance associated to connective tissue disorders.

Optical imaging and MRI contrast agents according to the present invention may be used in the same manner as conventional optical imaging and MRI contrast reagents.

When the target is, for example, a given site in a tissue, certain MR techniques and pulse sequences may be preferred to enhance the contrast of the site to the background blood and tissues. These techniques include (but are not limited to), for example, black blood angiography sequences that seek to make blood dark, such as fast spin echo sequences [see, e.g., Alexander et al., Magnetic Resonance in Medicine, 40(2): 298-310 (1998)] and flow-spoiled gradient echo sequences [see, e.g., Edelman et al., Radiology, 177(1): 45-50 (1990)]. These methods also include flow independent techniques that enhance the difference in contrast, such as inversion-recovery prepared or saturation-recovery prepared sequences that will increase the contrast between target containing tissues and background tissues.

In case of radiotherapy, proper dose schedules known in the art may be used for the radiotherapeutic compounds of the present invention.

In case of radionuclide imaging, the compounds of the invention may be administered to the patient through injection. A PET camera or a gamma camera calibrated for the gamma ray energy of the nuclide incorporated in the imaging agent is used to image areas of uptake of the agent and quantify the amount of radioactivity present in the site. Imaging of the site in vivo can take place in a matter of a few minutes. However, imaging can take place, if desired, in hours or even longer, after the radiolabelled compound is injected into a patient. In most instances, a sufficient amount of the administered dose will accumulate in the area to be imaged within about 0.1 to 1 hour to permit the taking of scintiphotos.

In order to obtain the desired prophylactic, therapeutic or diagnostic effect, a therapeutically or diagnostically effective dose or amount of the active ingredient is advantageously administered in the form of a unit dose, one or more times daily. The daily dosages are obviously selected by the health professional depending on the biologically active molecule introduced.

The term "effective dose or amount", as used herein, refers to any amount of a diagnostic or a therapeutic molecule of the invention, or pharmaceutical composition thereof, that is sufficient to fulfil its intended diagnostic or therapeutic purpose(s): i.e., for example, to visualize a patient biological element including cells, biological fluids and biological tissues as well as human body organs, regions or tissues affected by metalloproteases overexpression, or its intended therapeutic purpose(s); or to delay or to prevent to onset of a pathological condition associated with metalloproteases overexpression; or to slow down or stop the progression, aggravation, or deterioration of the symptoms.

In a further embodiment, also provided is the use of the compounds of the invention labelled with a diagnostically active imaging moiety for the preparation of a diagnostic formulation for use in the diagnostic imaging, both in vitro and in vivo, of pathological systems, including cells, biological fluids and biological tissues originating from a live mammal patient and, preferably, a human patient, as well as of human body organs, regions or tissues wherein a non-physiological overexpression of metalloproteases occurs as well as for monitoring the progress and results of the therapeutic treatment of the said pathologies.

In yet another aspect, the invention provides a method of in vitro imaging, for instance by contacting a suitable compound of the invention with biological samples and tissues, for example ex vivo samples.

Inhibitory Activity

As reported in the previous paragraphs, the compounds of formula (I) are endowed with inhibitory activity against matrix metalloproteases and are therefore useful, in therapy, in the treatment of pathologies in which the regulation of said enzymes is altered.

The compounds of the invention, properly labelled with imaging moieties, maintain their affinity towards these metalloproteases and, thus, represent a powerful tool to selectively visualize and image body tissues, districts or organs wherein an overexpressions of the said metalloproteases occur.

More in particular, the compounds of the invention were tested to prove their affinity against selected metalloproteases, according to the method described in Example 26.

As reported therein, the inhibitory activity of the compounds of the invention was evaluated on the known fluorogenic substrate (Mca-Lys-Pro-Leu-Gly-Leu-Dpa-Ala-Arg-$NH_2$), shortly referred to as FS-6 (see, as a reference, U. Neumann, *Analytical Biochem.* 2004, 328, 166-173).

The said fluorogenic substrate was developed from the analogous FS-1 (see, as a reference, the aforementioned C G Knight et al., in *Febs Lett.* 1992, 296, 263-266) through the insertion of a lysine residue between Mca and Proline residues.

As the elongation of the peptide chain, in FS-6, was reported as improving the ability of the substrate to be hydrolyzed by MMPs, presumably because of the sterically hindered Mca moiety that might have been responsible for the decreased substrate affinity for some MMPs, present compounds were tested according to this more accurate and highly sensible method, based on FS-6.

Therefore, as per the experimental data thus obtained and comments thereof (see Example 26), the compounds of the invention resulted to be endowed with an affinity against the metalloproteases at least comparable to that exerted by the corresponding compounds of formula (I) from which they derive.

In addition, because of their unexpected profile, the compounds of the invention when properly labelled with radiotherapeutic moieties may also be used, in therapy, in the treatment of those pathologies wherein an overexpression of metalloproteases is observed, including degenerative disorders and tumours and, more in general, pathologies leading to an altered tissutal morphology with uncontrolled cell proliferation.

Therefore, it is an additional embodiment of the invention an agent comprising the residue of one or more metalloproteases inhibitors of formula (I), labelled with one or more imaging agents, and the pharmaceutically acceptable salts thereof, for use as a diagnostic agent.

In a still another embodiment, the invention concerns pharmaceutical compositions comprising, as an active ingredient, a pharmaceutically effective amount of an agent comprising the residue of one or more metalloproteases inhibitors of formula (I), labelled with one or more imaging or radiotherapeutic moieties, and the pharmaceutically acceptable salts thereof, in combination with one or more pharmaceutically acceptable carrier, diluent or excipient.

The compositions of the invention can be well prepared according to conventional methods widely known in the art for the preparation of pharmaceutical forms and may comprise any of the carriers, diluents or excipients known in the art for the intended purpose.

In a yet another aspect, the invention provides a method for the treatment of the above degenerative disorders, which method comprises the administration, to a mammal in need thereof, of a therapeutically effective amount of an agent comprising the residue of one or more metalloproteases inhibitors of formula (I), labelled with one or more radiotherapeutic moieties, and the pharmaceutically acceptable salts thereof.

From all of the above, it can be easily envisaged that the compounds of this invention may have a wide range of applications, both in diagnostics and in therapy, and may be thus properly formulated according to conventional methods for the intended administration route: i.e. topical, oral and enteral administration.

With the aim of better illustrate the present invention, without posing any limitation to it, the following examples are now given. In this respect, further applications including possible variants to the preparative process, that will become evident to the skilled person, are thus to be considered as comprised within the scope of the present invention.

EXPERIMENTAL SECTION

The following examples refer to the preparation of some representative metalloproteases inhibitors of formula (I), inclusive of possible intermediate compounds thereof, and to the preparation of the compounds of the invention wherein the given metalloproteases inhibitors of formula (I) are properly labelled.

The compounds of formula (I) were prepared according to the following Schemes; unless otherwise provided, reference to the compounds numbering as reported in the following schemes will be maintained.

Those presently numbered as compounds (1a-1h) were prepared by the method outlined in Scheme 1.

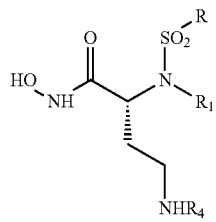

(1a -1h)

| | R | $R_1$ | $R_4$ |
|---|---|---|---|
| 1a | biphenyl-4-yl | benzyloxy | benzyloxycarbonyl |
| 1b | biphenyl-4-yl | isopropoxy | benzoyl |

-continued (1a -1h)

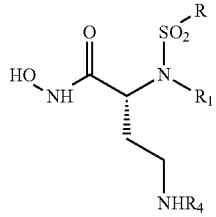

| R | R₁ | R₄ |
|---|---|---|
| 1c biphenyl-4-yl | isopropoxy | methanesulfonyl |
| 1d biphenyl-4-yl | isopropoxy | acetyl |
| 1e biphenyl-4-yl | isopropoxy | phenacetyl |
| 1f p(MeO)C₆H₄—C₆H₄— | isopropoxy | acetyl |
| 1g p(MeO)C₆H₄—C₆H₄— | isopropoxy | phenacetyl |
| 1h biphenyl-4-yl | —O—(CH₂)₂—O—(CH₂)₂—N(piperazine)NH | benzyloxycarbonyl |

Optically active α-hydroxy-tert-butyl ester (6) was synthesized by direct esterification of commercially available α-hydroxy acid (5) with N,N-dimethylformamide di-tert-butyl acetal (see Rossello, A. et al.; *Bioorg. Med. Chem. Lett*, 2005, 15, 1321). A Mitsunobu condensation reaction of sulfonamides (7-10) with α-hydroxy-tert-butyl-ester (6), gave tert-butyl esters (11-14). Acid cleavage of esters (11, 14) yielded carboxylic acids (35, 36) which were converted to their O-silylate (37, 38) upon treatment with O-(tert-butyl-dimethylsilyl)hydroxylamine. Hydrolysis with trifluoroacetic acid of tert-butyl O-silylate (37, 38) provided hydroxamic acids (1a, 1h). Tert-butyl esters (17-22) were obtained by Pd-catalyzed hydrogenation of (12, 13) followed by acylation with commercial acyl chlorides. Acid cleavage of esters (17-22) yielded carboxylates (23-28) which were subsequently converted to their respective tert-butyl O-silylate (29, 34). Hydroxamic acids (1b-1g) were then obtained by treatment of (29, 34) with trifluoroacetic acid.

Additional compounds of formula (I) (2-4) were also prepared according to Scheme 2.

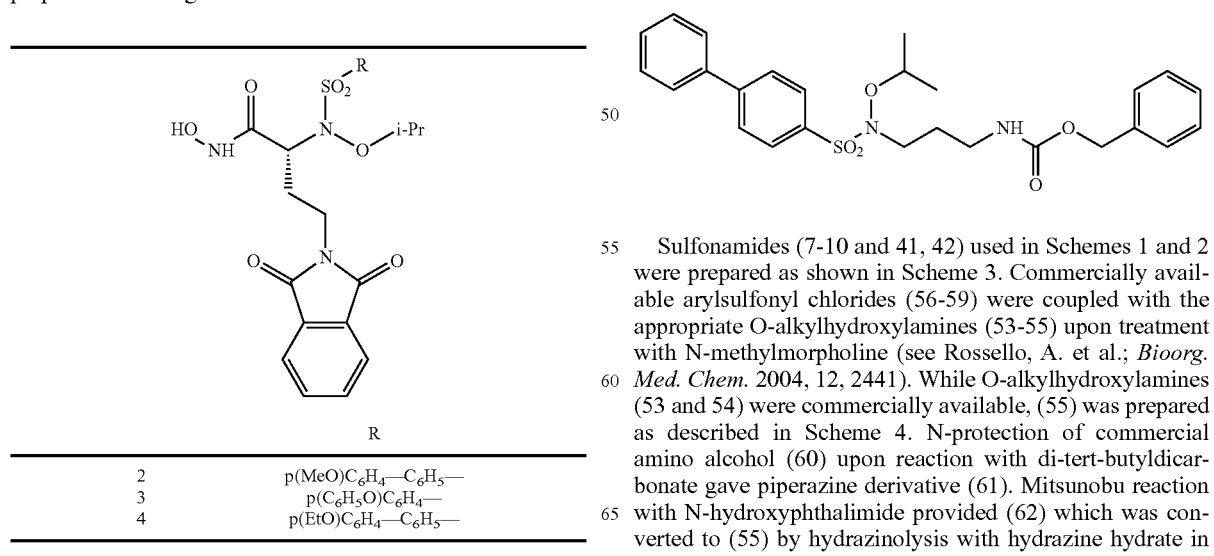

| | R |
|---|---|
| 2 | p(MeO)C₆H₄—C₆H₅— |
| 3 | p(C₆H₅O)C₆H₄— |
| 4 | p(EtO)C₆H₄—C₆H₅— |

(S)-α-Hydroxy-tert-butyl ester (40) was obtained by direct esterification of commercially available α-hydroxy acid (39) using N,N-dimethylformamide di-tert-butyl acetal. A Mitsunobu coupling of sulfonamides (9, 41, and 42) with α-hydroxy-tert-butyl-ester (40), gave tert-butyl esters (43-45). Acid cleavage of (43, 44) yielded carboxylic acids (46, 47) which were converted to their O-silylate (48, 49) upon treatment with O-(tert-butyl-dimethylsilyl)hydroxylamine. Hydrolysis with trifluoroacetic acid of tert-butyl O-silylate (48, 49) provided hydroxamic acids (2 and 3). Suzuki coupling of commercially available 4-ethoxyphenyl boronic acid with ester (45) gave biphenyl ester (50), which was converted to hydroxamic acid (4) using the procedure described above.

An additional compound of formula (I), presently indicated as compound (64), wherein both R₂ and R₃, in formula (I) are H atoms, was prepared as per Scheme 5 below, through Mitsunobu condensation reaction between commercially available alcohol (63) with sulphonamide (8)

(64)

Sulfonamides (7-10 and 41, 42) used in Schemes 1 and 2 were prepared as shown in Scheme 3. Commercially available arylsulfonyl chlorides (56-59) were coupled with the appropriate O-alkylhydroxylamines (53-55) upon treatment with N-methylmorpholine (see Rossello, A. et al.; *Bioorg. Med. Chem.* 2004, 12, 2441). While O-alkylhydroxylamines (53 and 54) were commercially available, (55) was prepared as described in Scheme 4. N-protection of commercial amino alcohol (60) upon reaction with di-tert-butyldicarbonate gave piperazine derivative (61). Mitsunobu reaction with N-hydroxyphthalimide provided (62) which was converted to (55) by hydrazinolysis with hydrazine hydrate in ethanol.

Additional compounds of formula (I) (1i-1k) having the following formulae were also prepared:

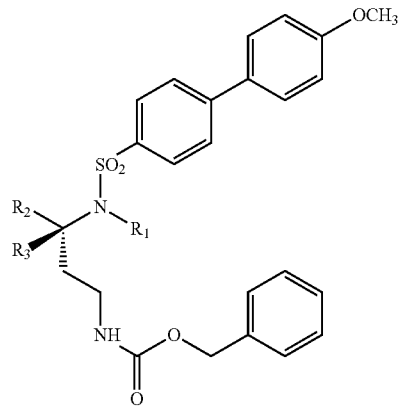

(1i-1k)

One of $R_2$ or $R_3$ is H and the other of $R_2$ or $R_3$ is: $R_1$

| | $R_1$ | |
|---|---|---|
| 1i | —COOH | 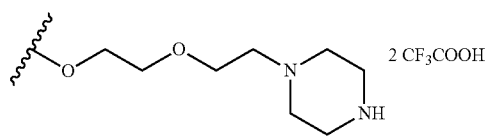 [SMILES: *OCCOCCN1CCNCC1] 2 CF$_3$COOH |
| 1j | —CONHOH | 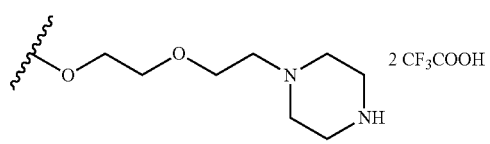 [SMILES: *OCCOCCN1CCNCC1] 2 CF$_3$COOH |
| 1k | —CONHOH | 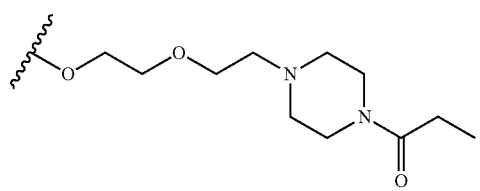 [SMILES: *OCCOCCN1CCN(C(=O)CC)CC1] |

Compounds (1i) and (1j) were prepared as shown in scheme 6 by properly reacting, as formerly reported under Mitsunobu coupling conditions, the sulphonamido derivative (65) with compound (6) of scheme 1. The obtained compound (66) was then deprotected with trifluoroacetic acid so as to obtain compound (1i) as di-trifluoroacetate salt.

This latter carboxylic acid was then converted into the corresponding hydroxamic acid derivative (1j) di-trifluoroacetate, as formerly reported.

Compound (1j) was then acylated at the piperazino N atom with 2,5-dioxopyrrolidine-1-yl propionate, by working according to conventional methods in the presence of triethylamine, so as to obtain the corresponding compound (1k).

The starting material (65) was obtained, by analogy, as reported in schemes 3 and 4 for the preparation of compound (10).

The compounds of the invention labelled with imaging moieties were also prepared as per the following synthetic schemes 7 to 11; unless otherwise provided, compounds numbering in the above schemes and in the experimental section will be maintained, accordingly.

1H-NMR spectra were recorded on a Varian Gemini 200 (200 MHz) using CDCl$_3$ or DMSO-d$_6$, as solvents.

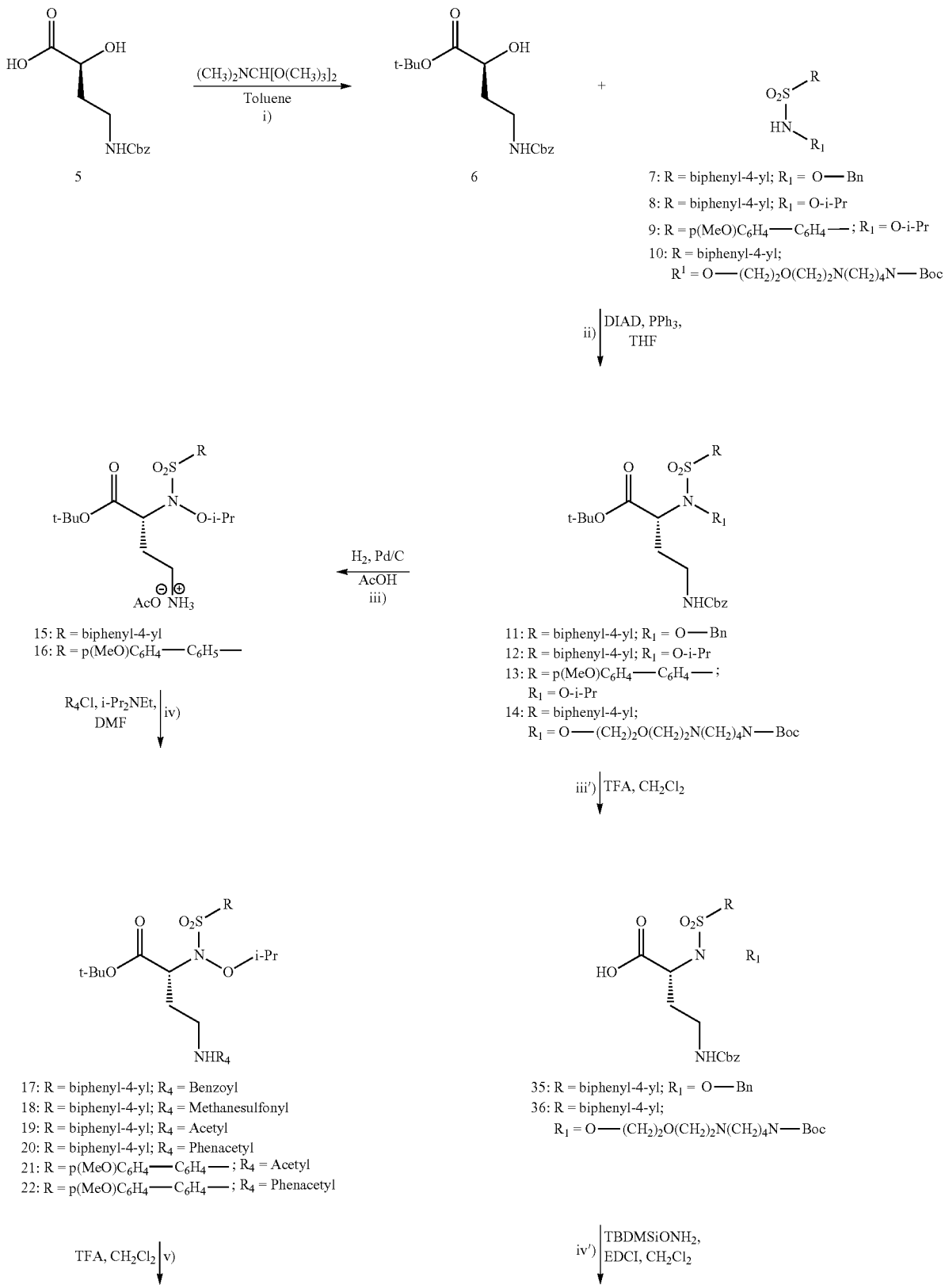

57

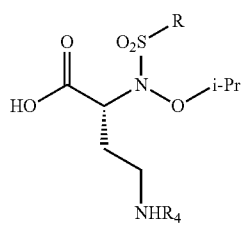

23: R = biphenyl-4-yl; R$_4$ = Benzoyl
24: R = biphenyl-4-yl; R$_4$ = Methanesulfonyl
25: R = biphenyl-4-yl; R$_4$ = Acetyl
26: R = biphenyl-4-yl; R$_4$ = Phenacetyl
27: R = p(MeO)C$_6$H$_4$—C$_6$H$_4$—; R$_4$ = Acetyl
28: R = p(MeO)C$_6$H$_4$—C$_6$H$_4$—; R$_4$ = Phenacetyl TBDMSiONH$_2$, EDCI, CH$_2$Cl$_2$ ↓ vi)

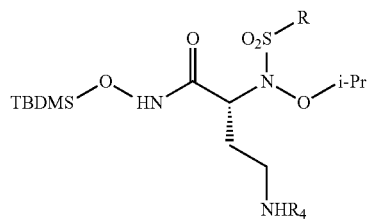

29: R = biphenyl-4-yl; R$_4$ = Benzoyl
30: R = biphenyl-4-yl; R$_4$ = Methanesulfonyl
31: R = biphenyl-4-yl; R$_4$ = Acetyl
32: R = biphenyl-4-yl; R$_4$ = Phenacetyl
33: R = p(MeO)C$_6$H$_4$—C$_6$H$_4$—; R$_4$ = Acetyl
34: R = p(MeO)C$_6$H$_4$—C$_6$H$_4$—; R$_4$ = Phenacetyl

58

-continued

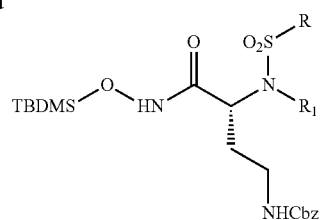

37: R = biphenyl-4-yl; R$_1$ = O—Bn
38: R = biphenyl-4-yl; R$_1$ = O—(CH$_2$)$_2$O(CH$_2$)$_2$N(CH$_2$)$_4$N—Boc v') ↓ TFA, CH$_2$Cl$_2$

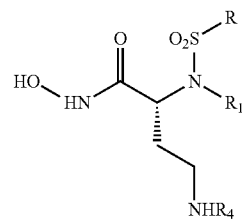

TFA, CH$_2$Cl$_2$ vii) →

(1a-h)

Additional Compounds were Prepared as Per Scheme 1 BIS, Below

Scheme 1 BIS

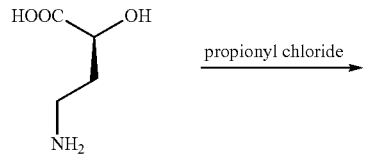

propionyl chloride →

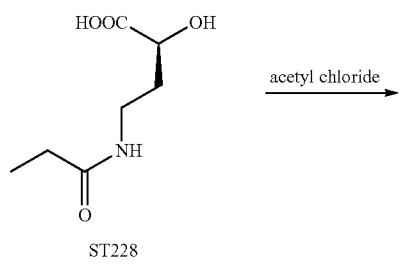

acetyl chloride →

ST228

-continued

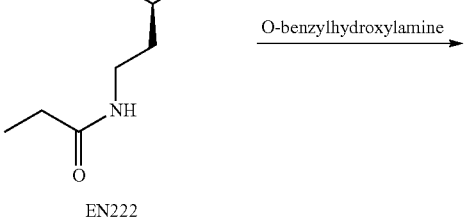

O-benzylhydroxylamine →

EN222

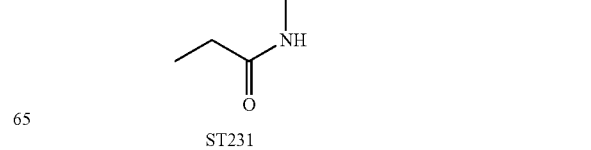

benzyl alcohol Ph$_3$P, DIAD →

ST231

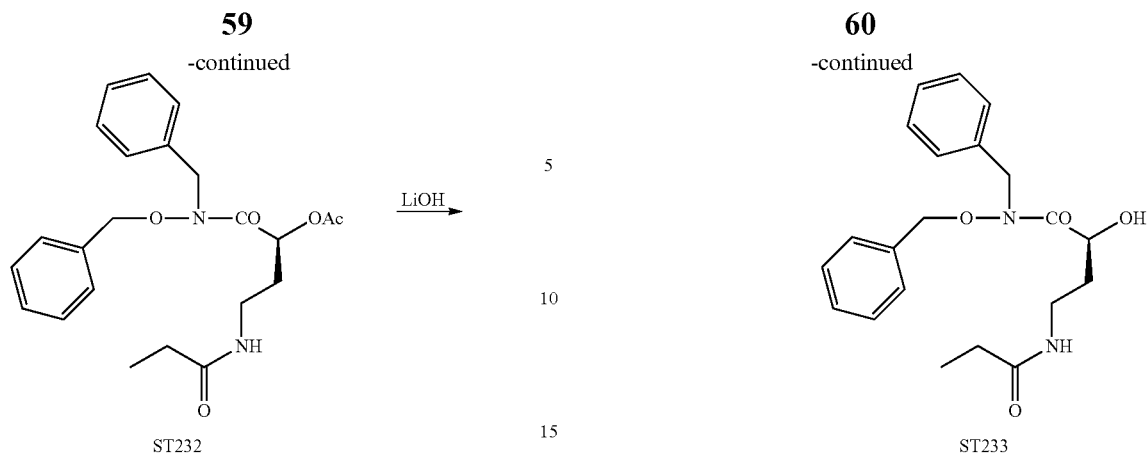
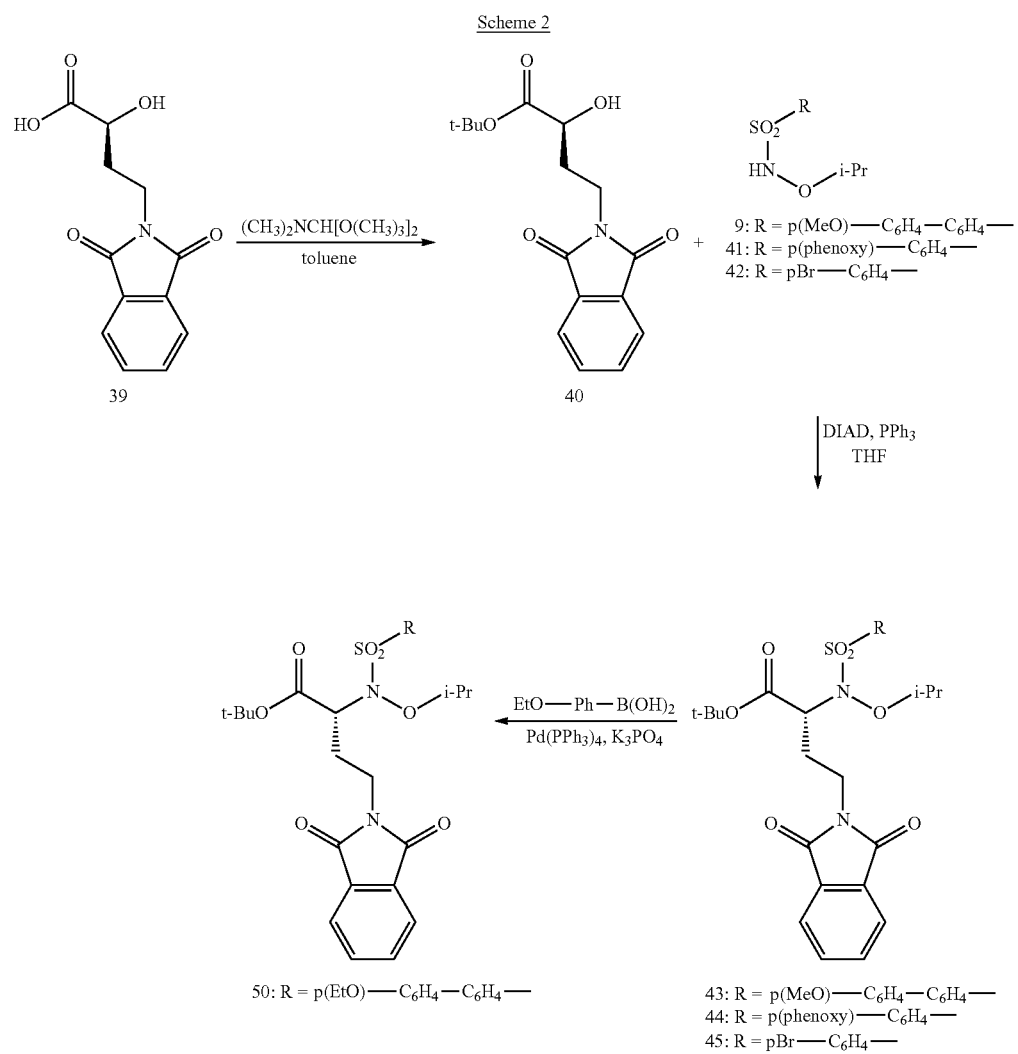
Scheme 2

-continued
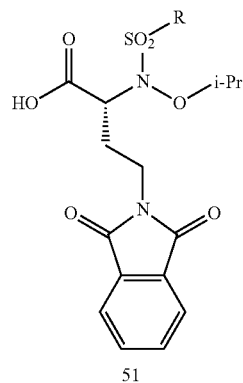
51
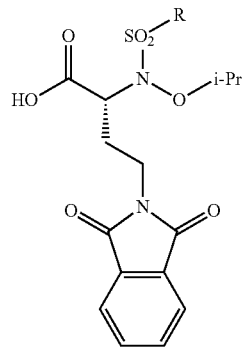
46: R = p(MeO)—C$_6$H$_4$—C$_6$H$_4$—
47: R = p(phenoxy)—C$_6$H$_4$—
TBDMSiONH$_2$ | EDCI, CH$_2$Cl$_2$
TBDMSiONH$_2$ | EDCI, CH$_2$Cl$_2$
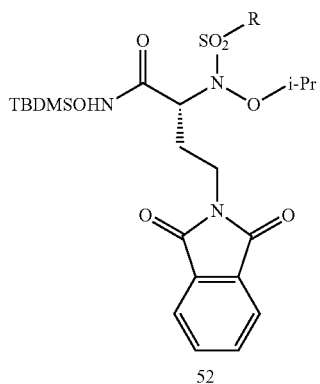
52
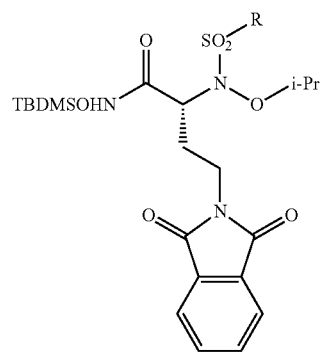
48: R = p(MeO)—C$_6$H$_4$—C$_6$H$_4$—
49: R = p(phenoxy)—C$_6$H$_4$—
TFA, CH$_2$Cl$_2$
TFA, CH$_2$Cl$_2$
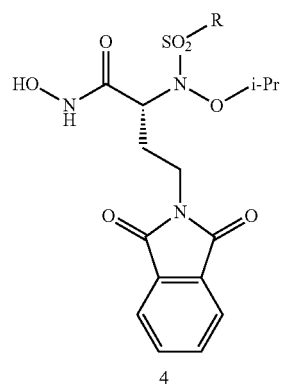
4
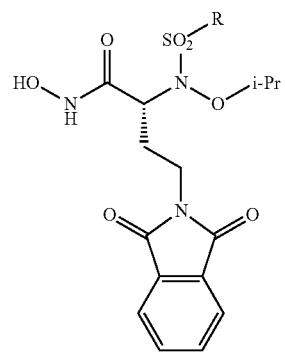
2: R = p(MeO)—C$_6$H$_4$—C$_6$H$_4$—
3: R = p(phenoxy)—C$_6$H$_4$—

Additional Compounds were Prepared as Per Scheme 2 Below

Scheme 2 bis

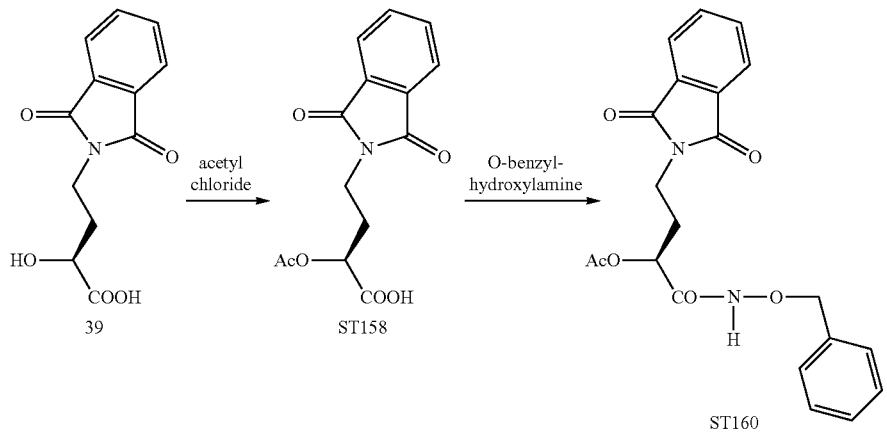

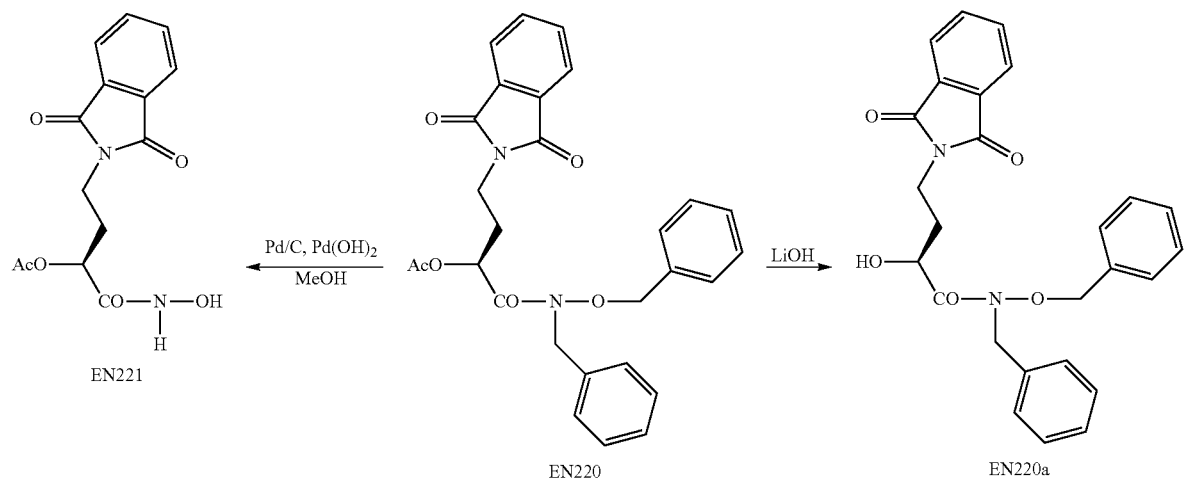

Scheme 3

$R_1$—$NH_2$ +

53: $R_1$ = benzyloxy
54: $R_1$ = isopropoxy
55: $R_1$ = ——O——$(CH_2)_2$——O——$(CH_2)_2$——N[$(CH_2)_4$]N——Boc R——$SO_2Cl$ $\xrightarrow{\text{NMM, THF}}$ 56: R = biphenyl-4-yl
57: R = p(MeO)——$C_6H_4$——$C_6H_4$——
58: R = p(PhO)——$C_6H_4$——
59: R = pBr——$C_6H_4$——

-continued

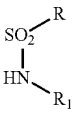

7: R = biphenyl-4-yl; $R_1$ = benzyloxy
8: R = biphenyl-4-yl; $R_1$ = isopropoxy
9: R = p(MeO)——$C_6H_4$——$C_6H_5$——; $R_1$ = isopropoxy
10: R = biphenyl-4-yl;
$R_1$ = ——O——$(CH_2)_2$——O——$(CH_2)_2$——N[$(CH_2)_4$]N——Boc
41: R = p(PhO)——$C_6H_4$——; $R_1$ = isopropoxy
42: R = pBr——$C_6H_4$——; $R_1$ = isopropoxy Scheme 4
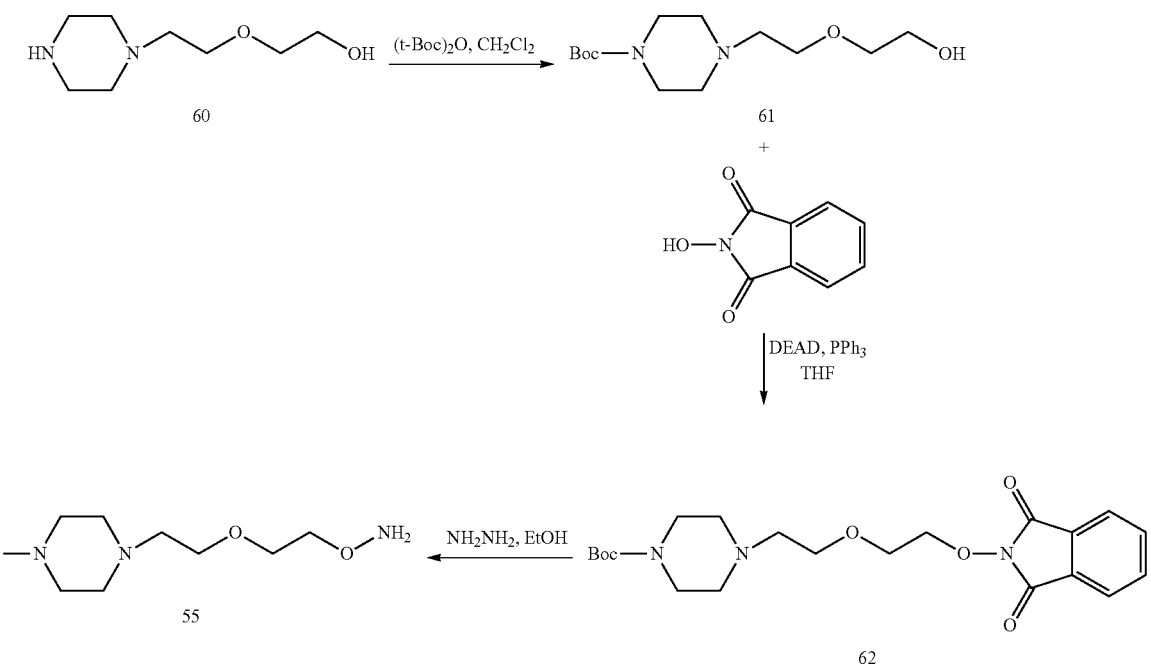
Additional Compounds were Prepared as Per Scheme 4 Bis Below
Scheme 4 BIS
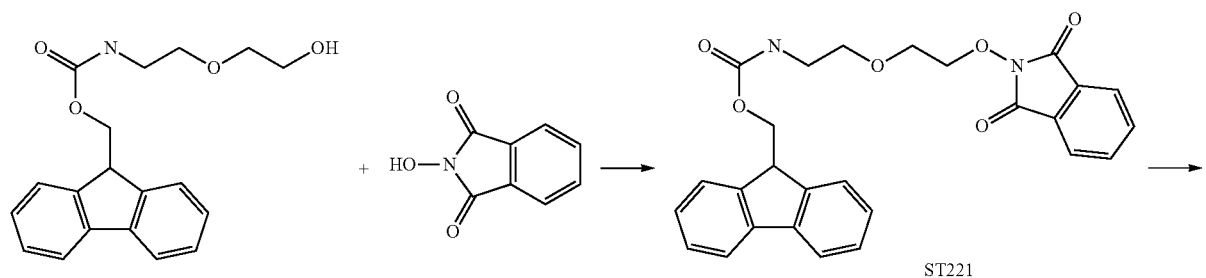
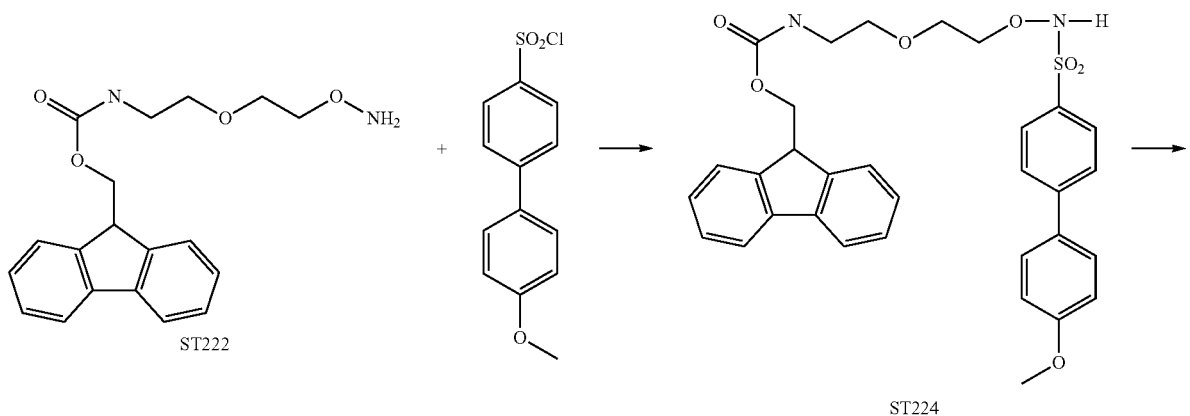

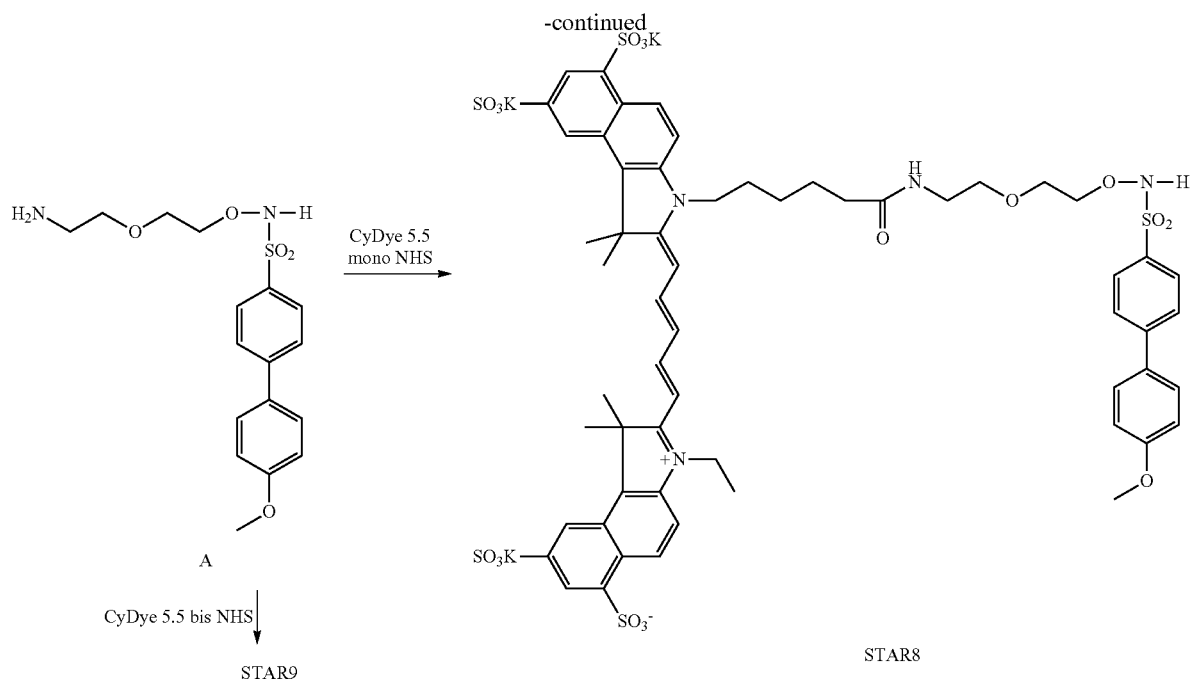
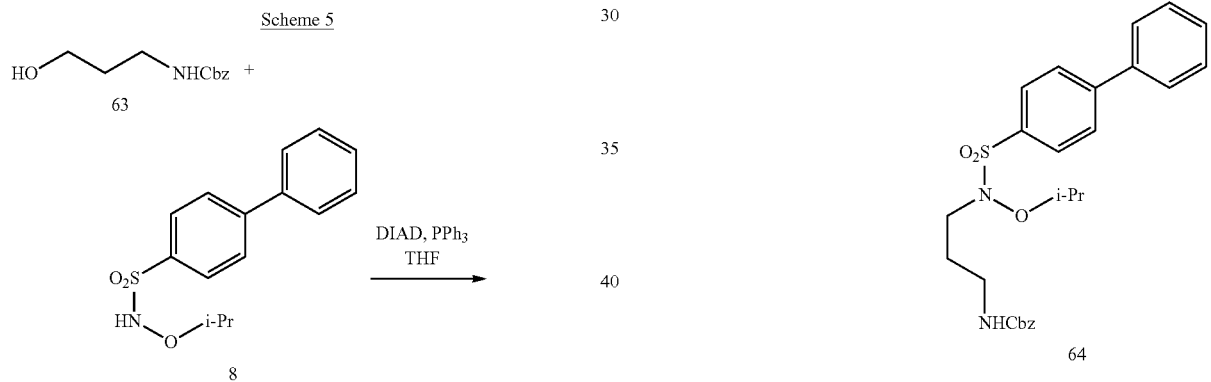
Scheme 6
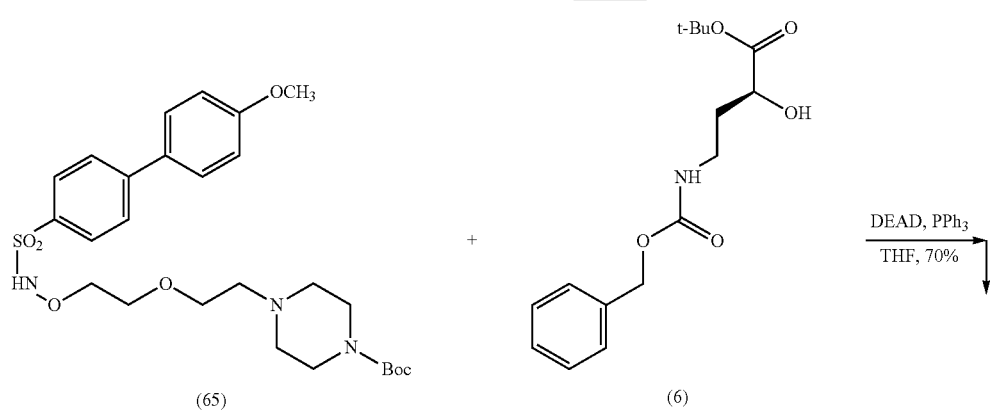

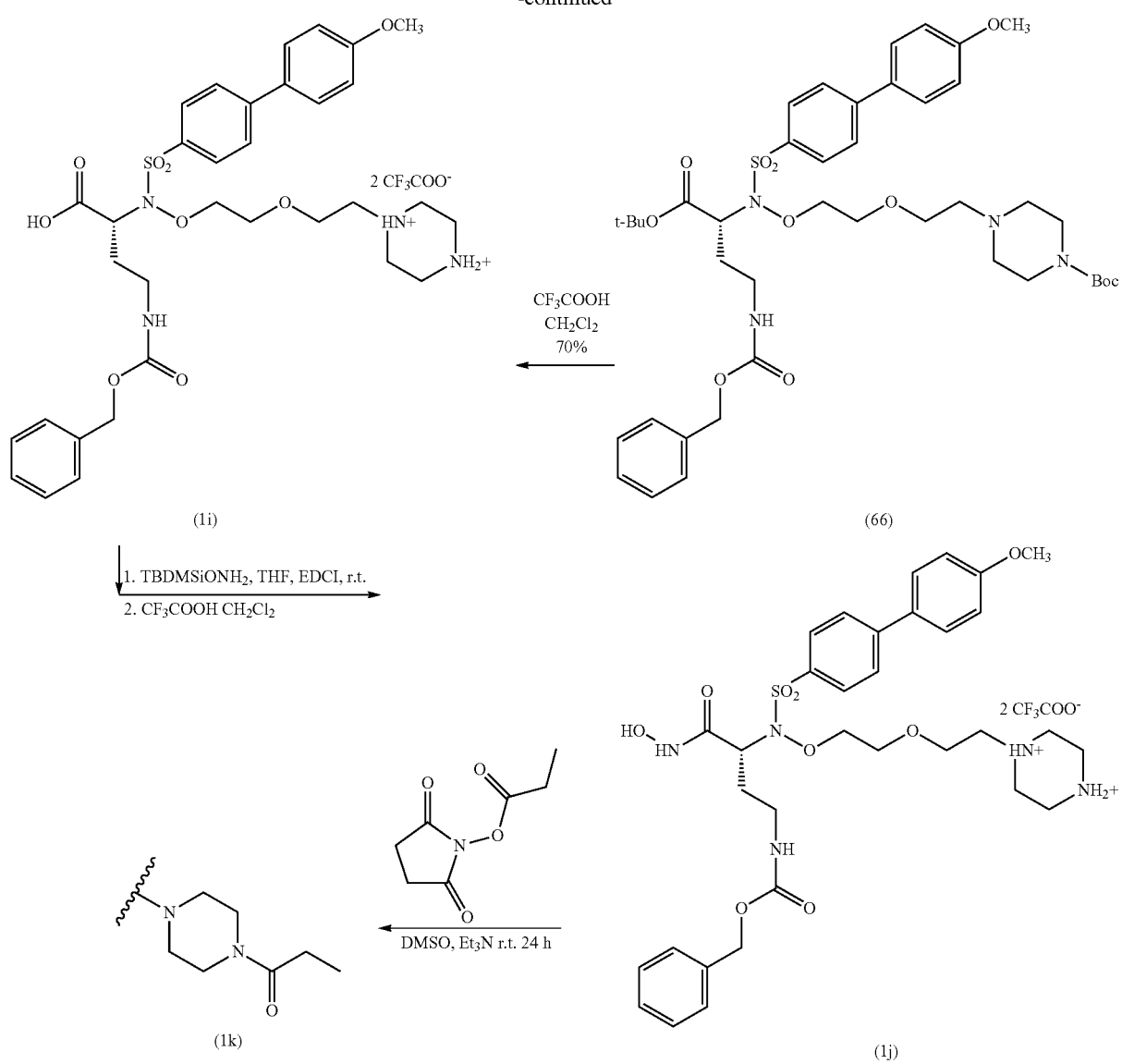
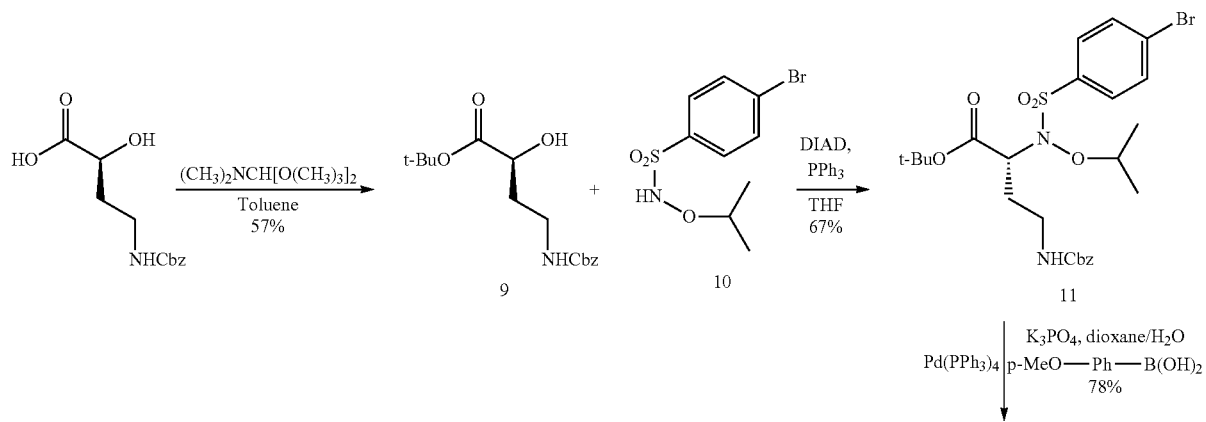
Scheme 7

71
72
-continued
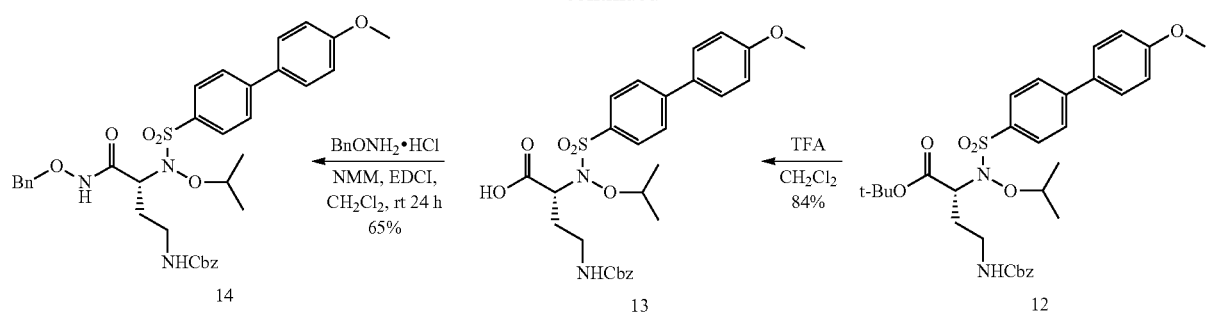
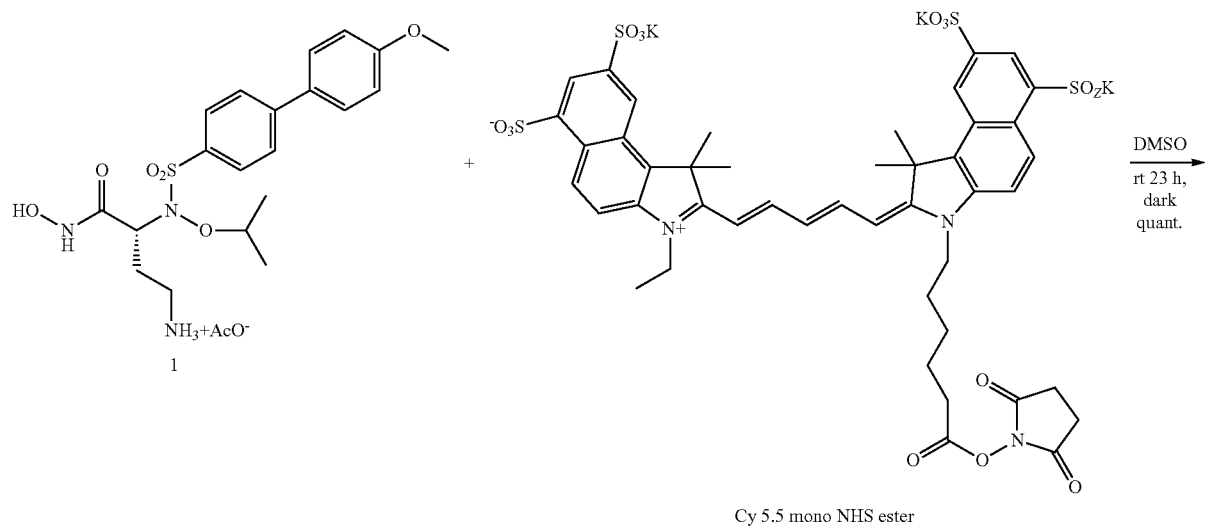
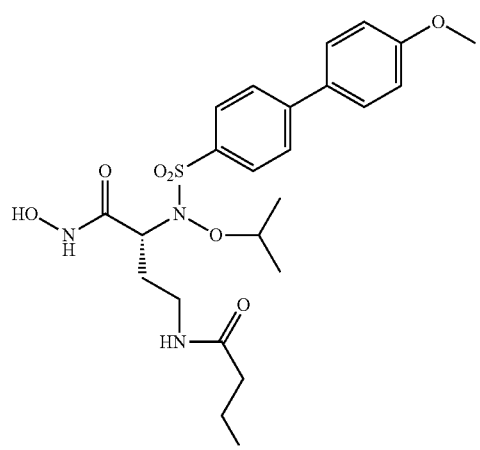

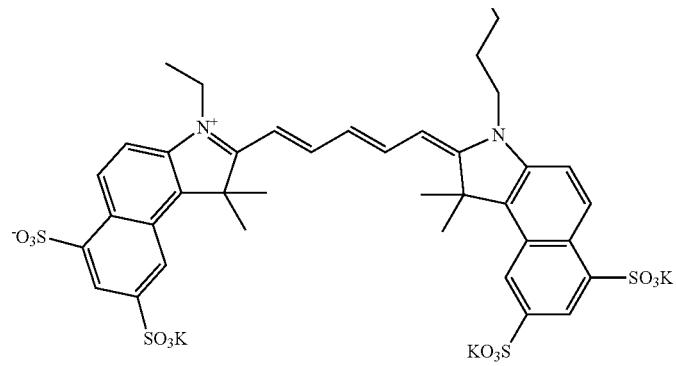
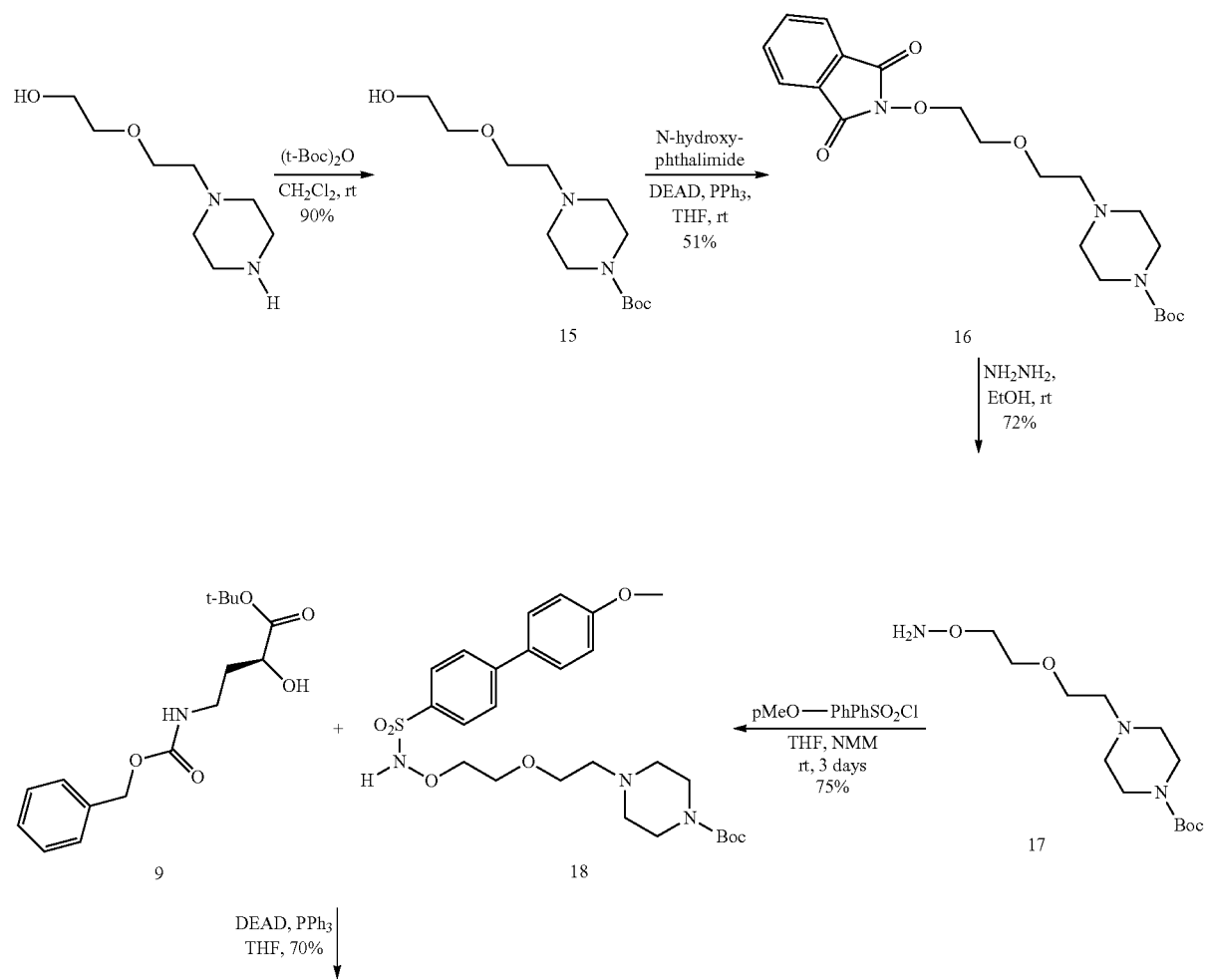
Scheme 8

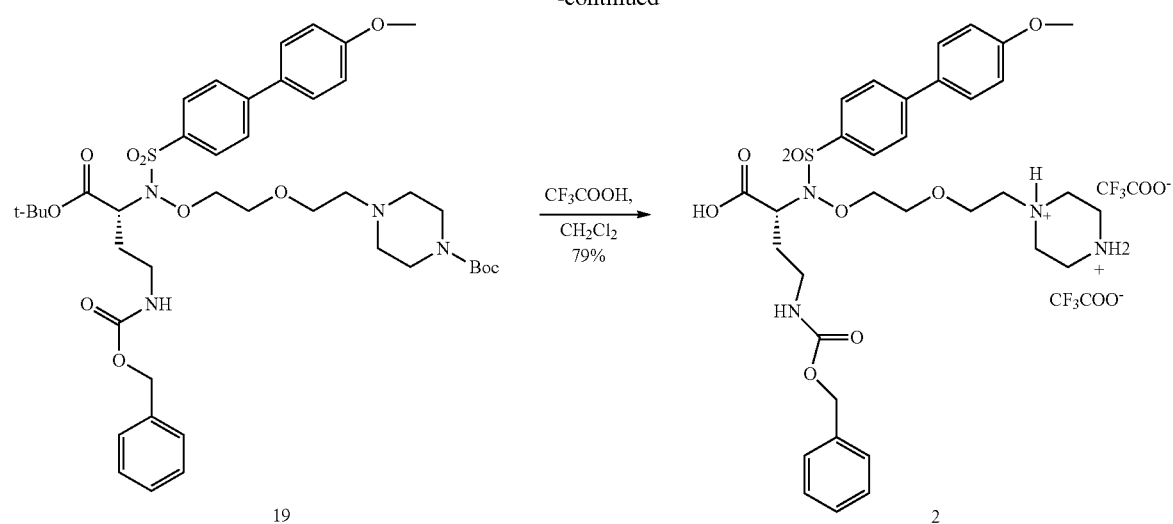
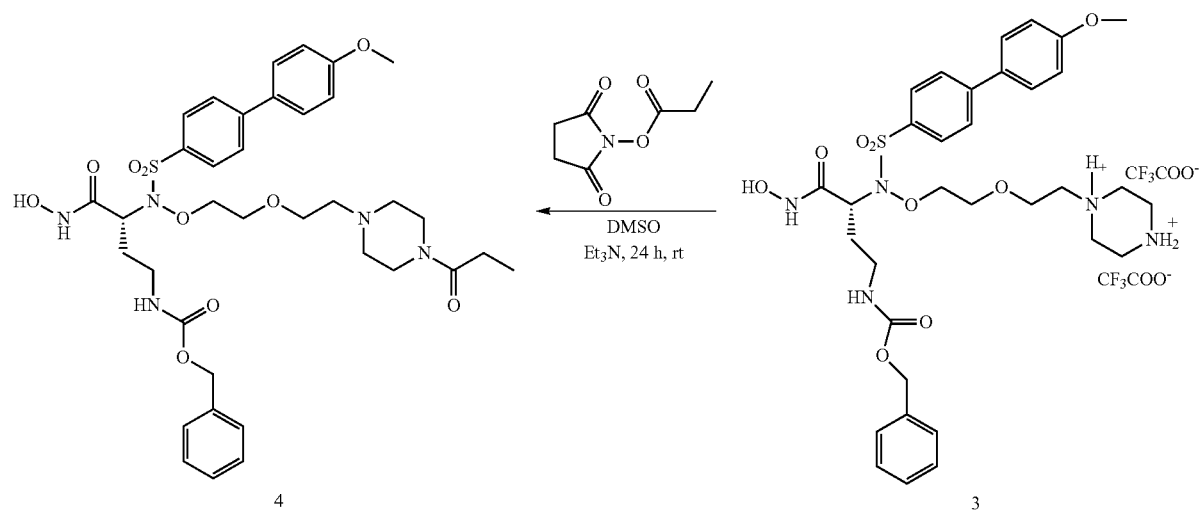

Scheme 9
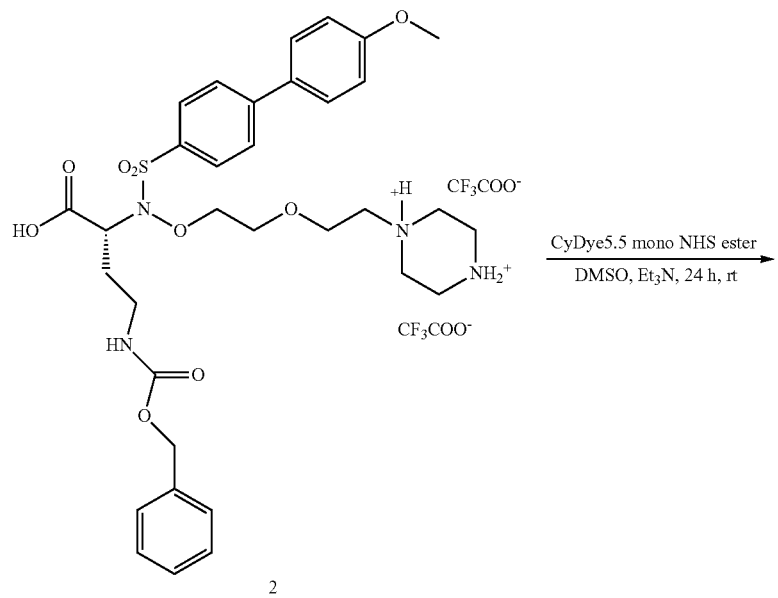
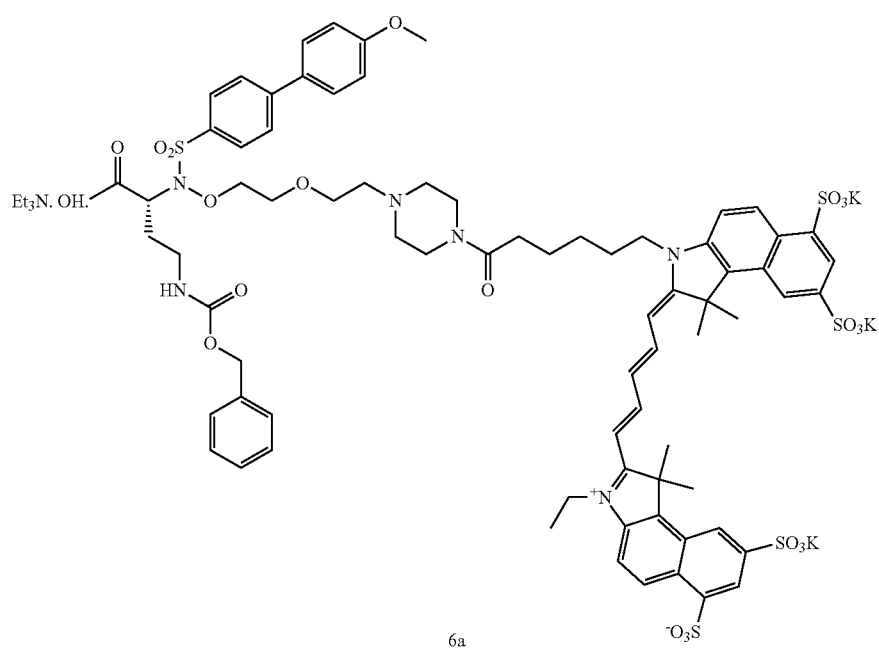

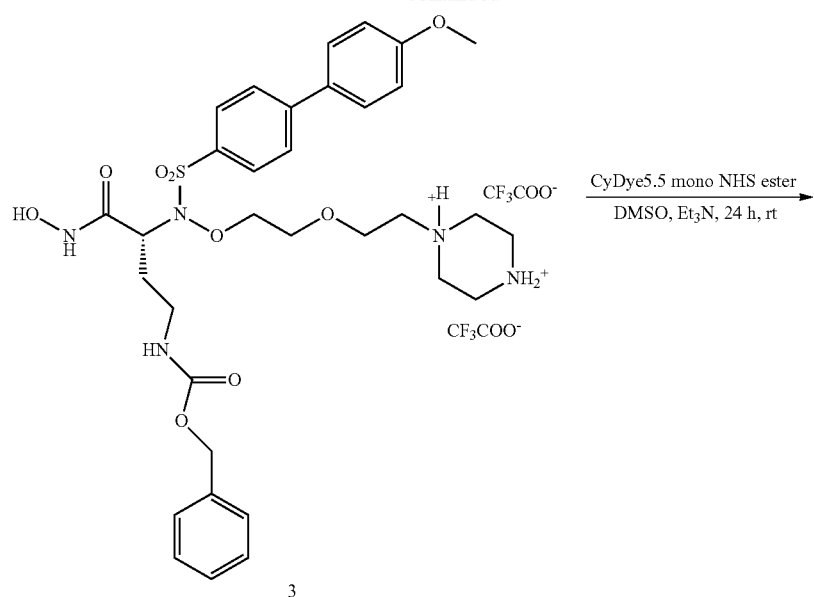
3
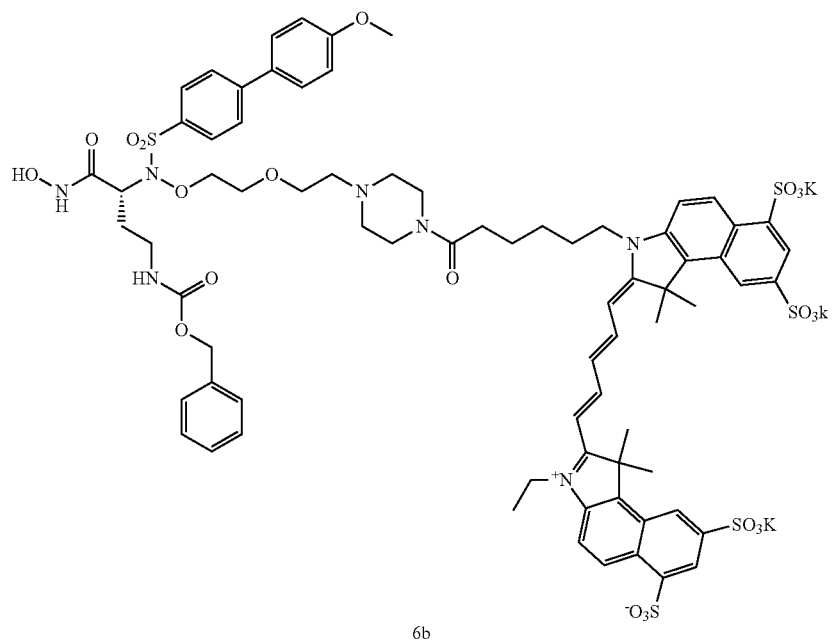
6b

Scheme 10
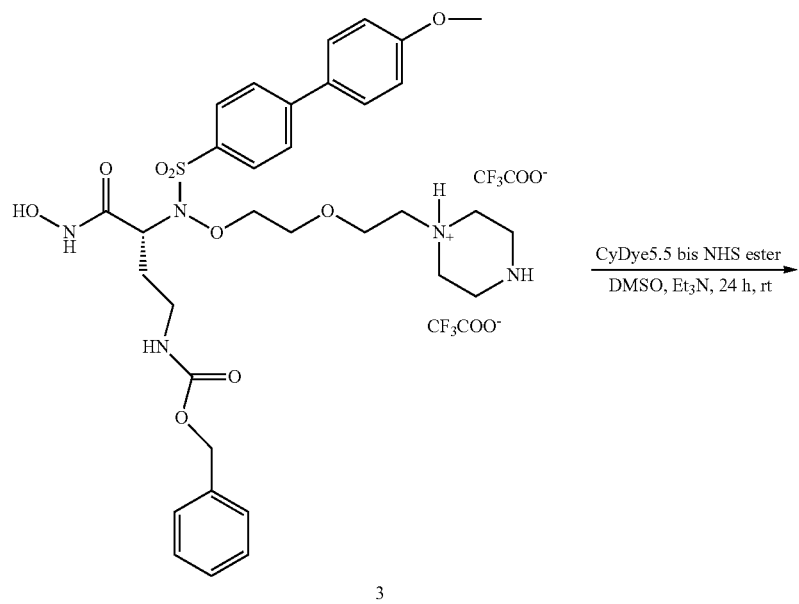
3
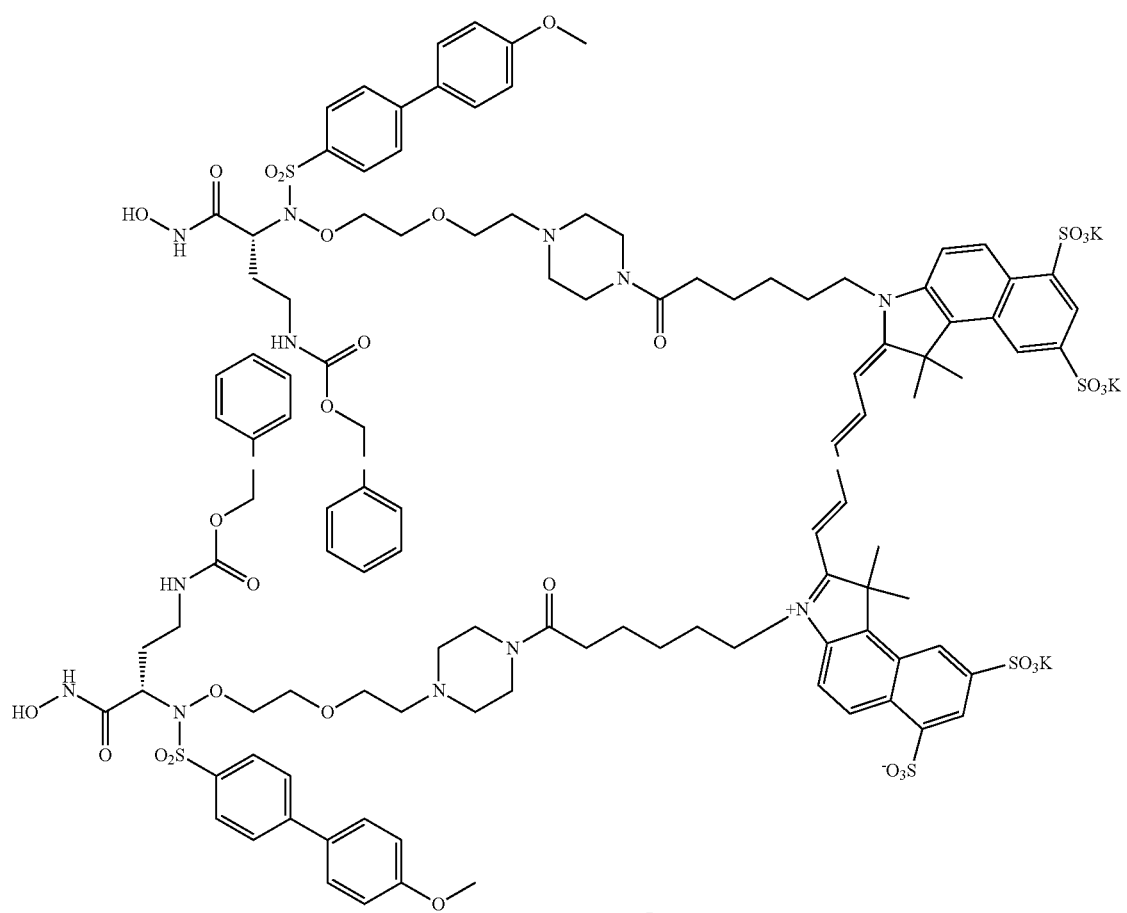
7

Additional Compounds were Prepared as Per Scheme 10 BIS Below
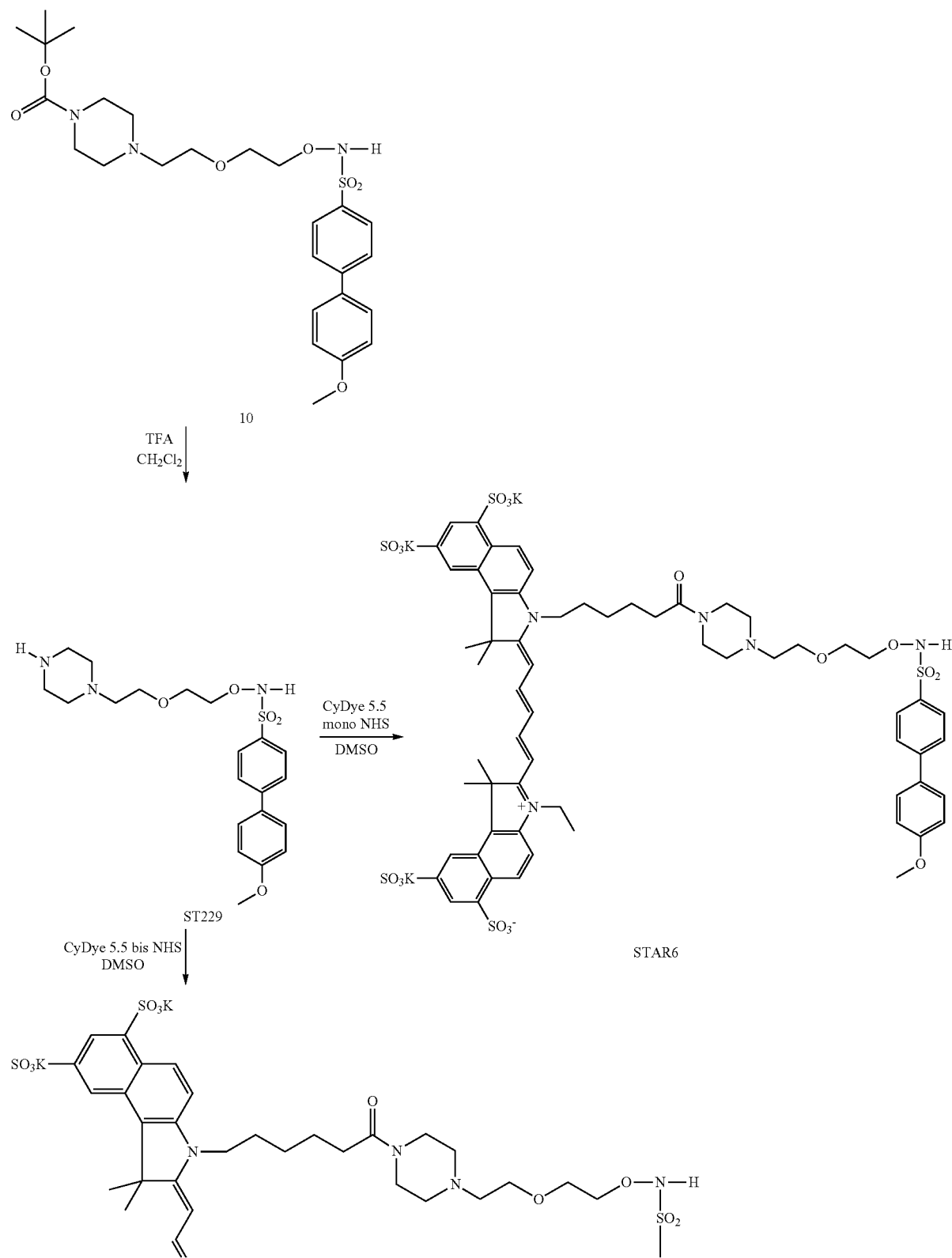

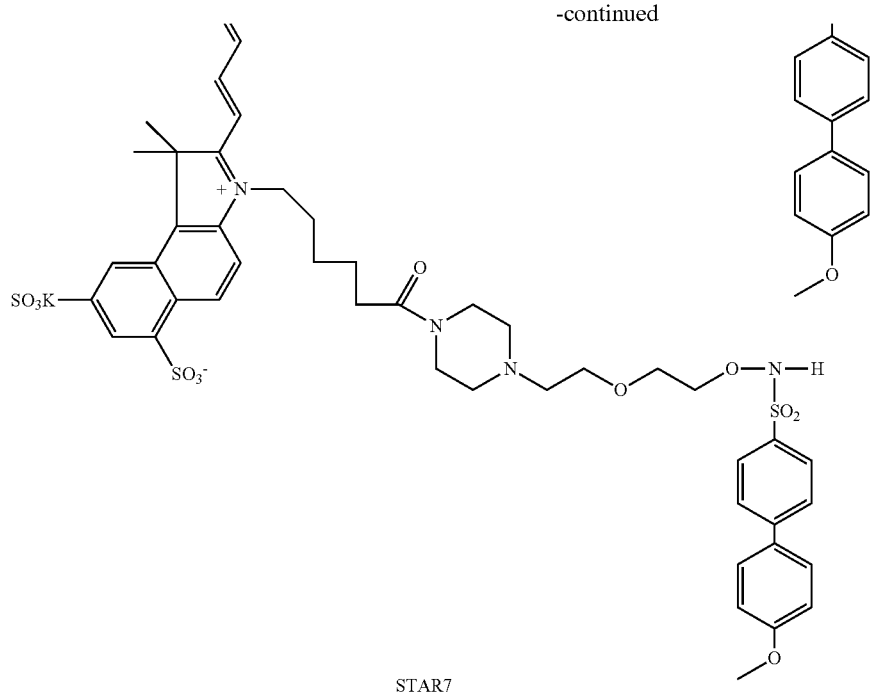
STAR7
Additional compounds were prepared as per Scheme 10 tert below wherein compounds ST223 and ST224 appear as the building blocks for the synthesis of "piperazine free" inhibitor of MMPs and the corresponding CyDye 5.5 mono- and bis-labelled derivatives.
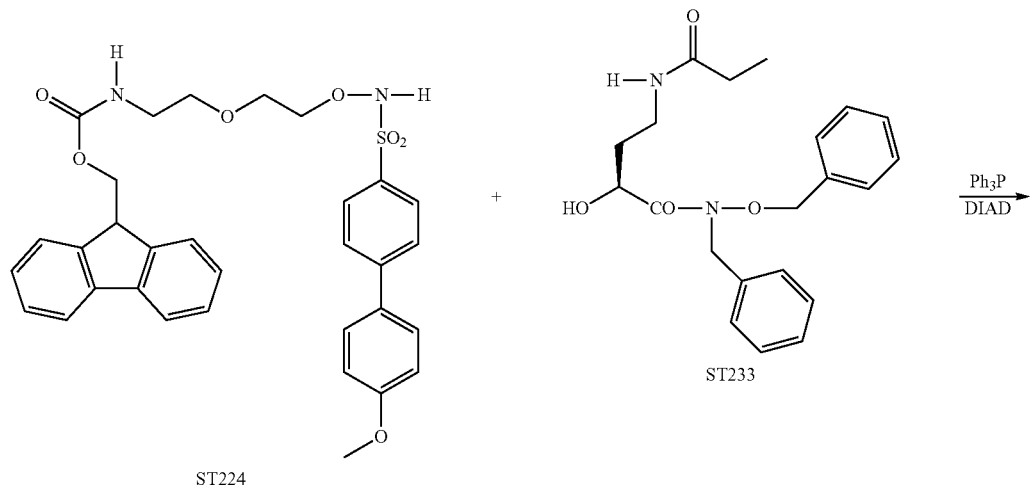

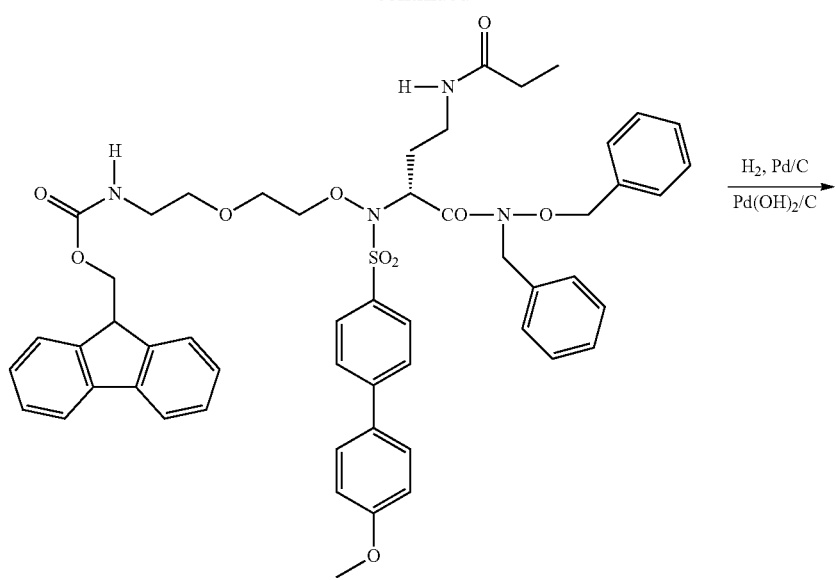
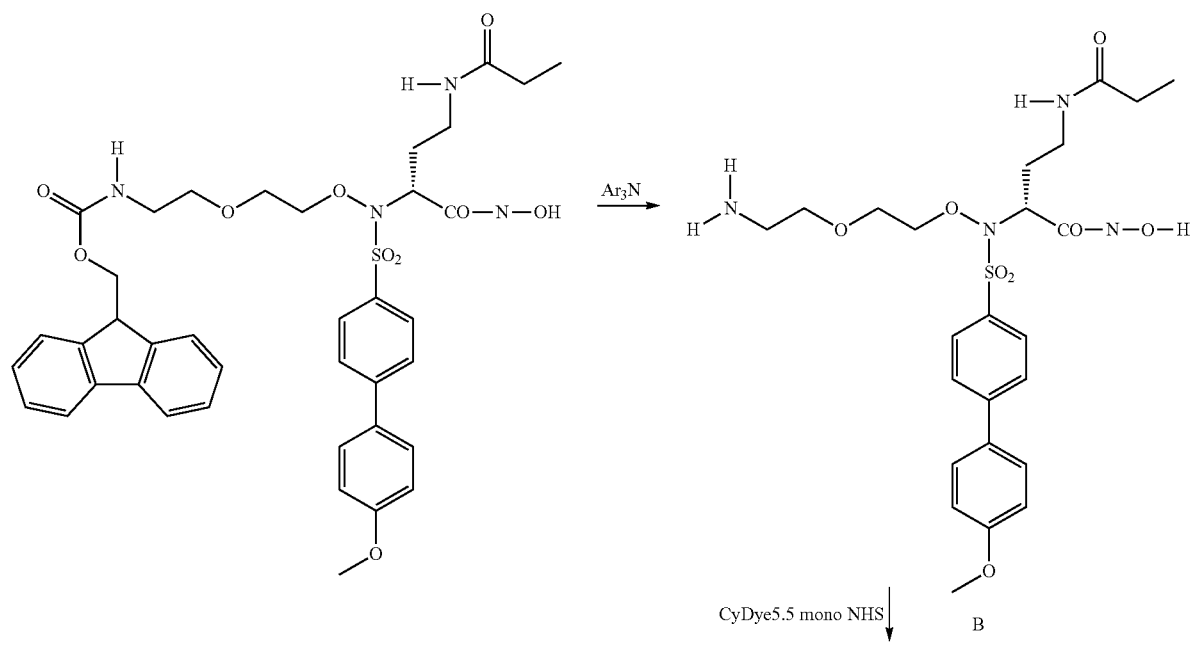

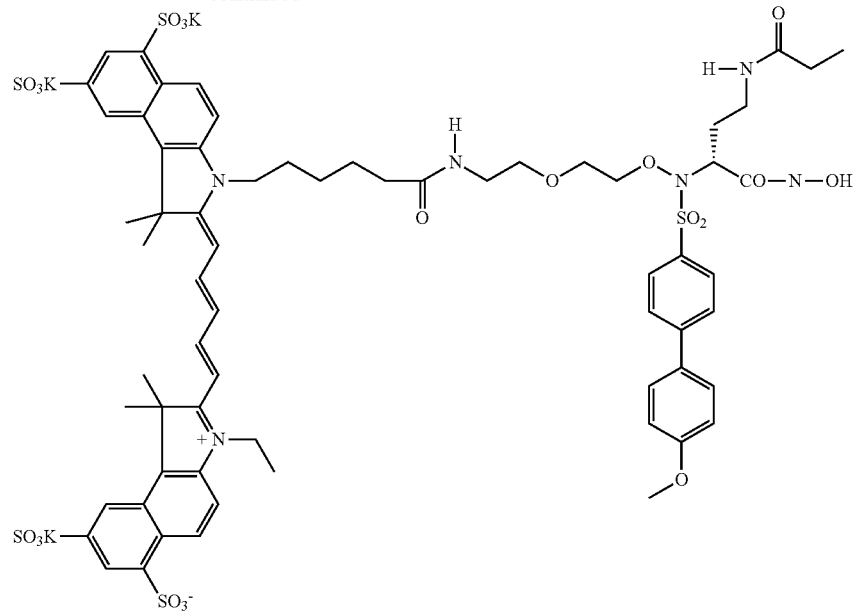
STAR10M
Structure of "Piperazine Free" CyDye5.5 Mono- and Bis-Labelled MMPIs:
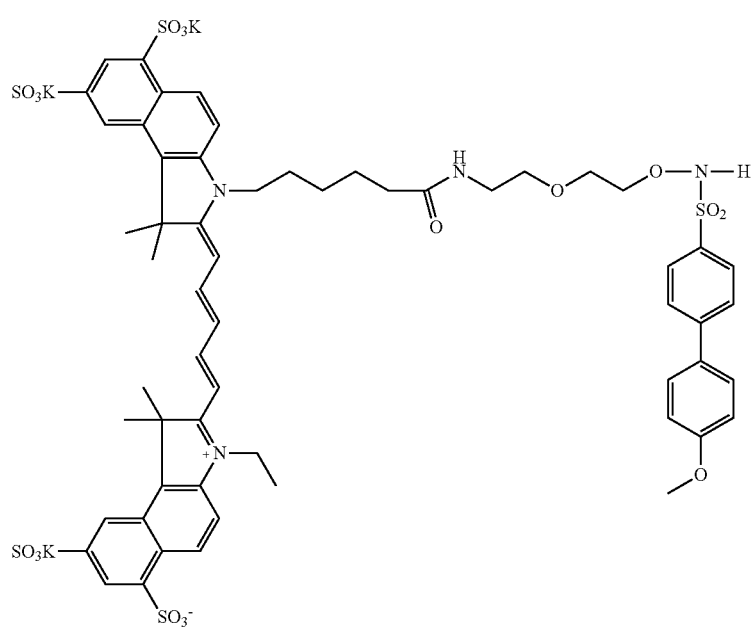
STAR8

STAR9
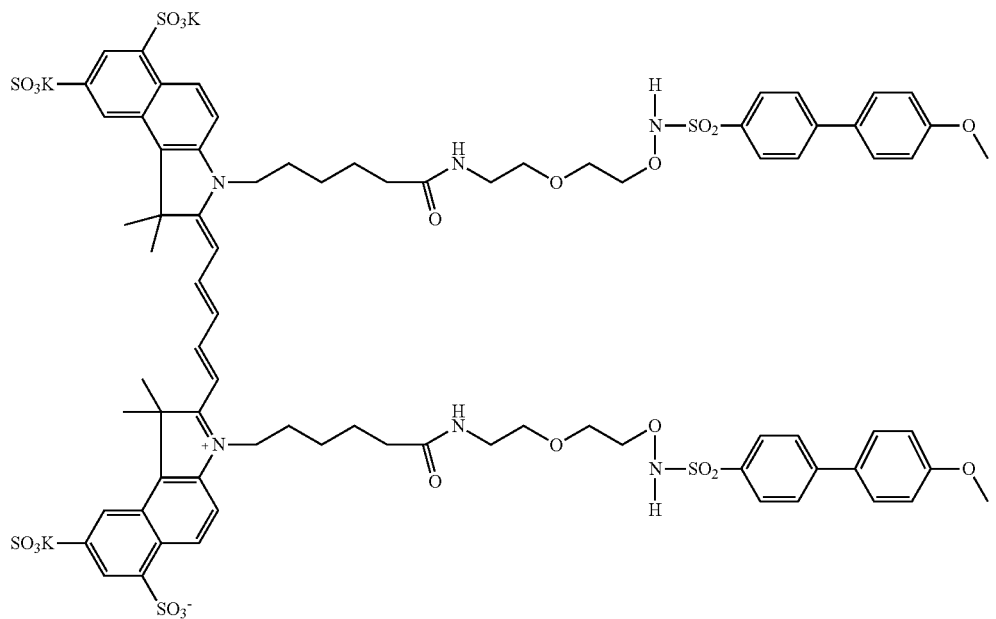
STAR10M
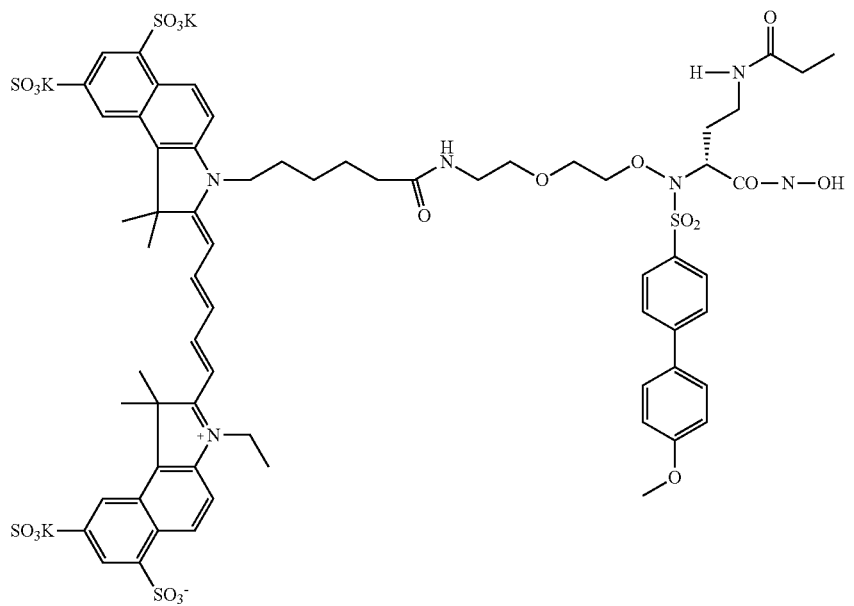

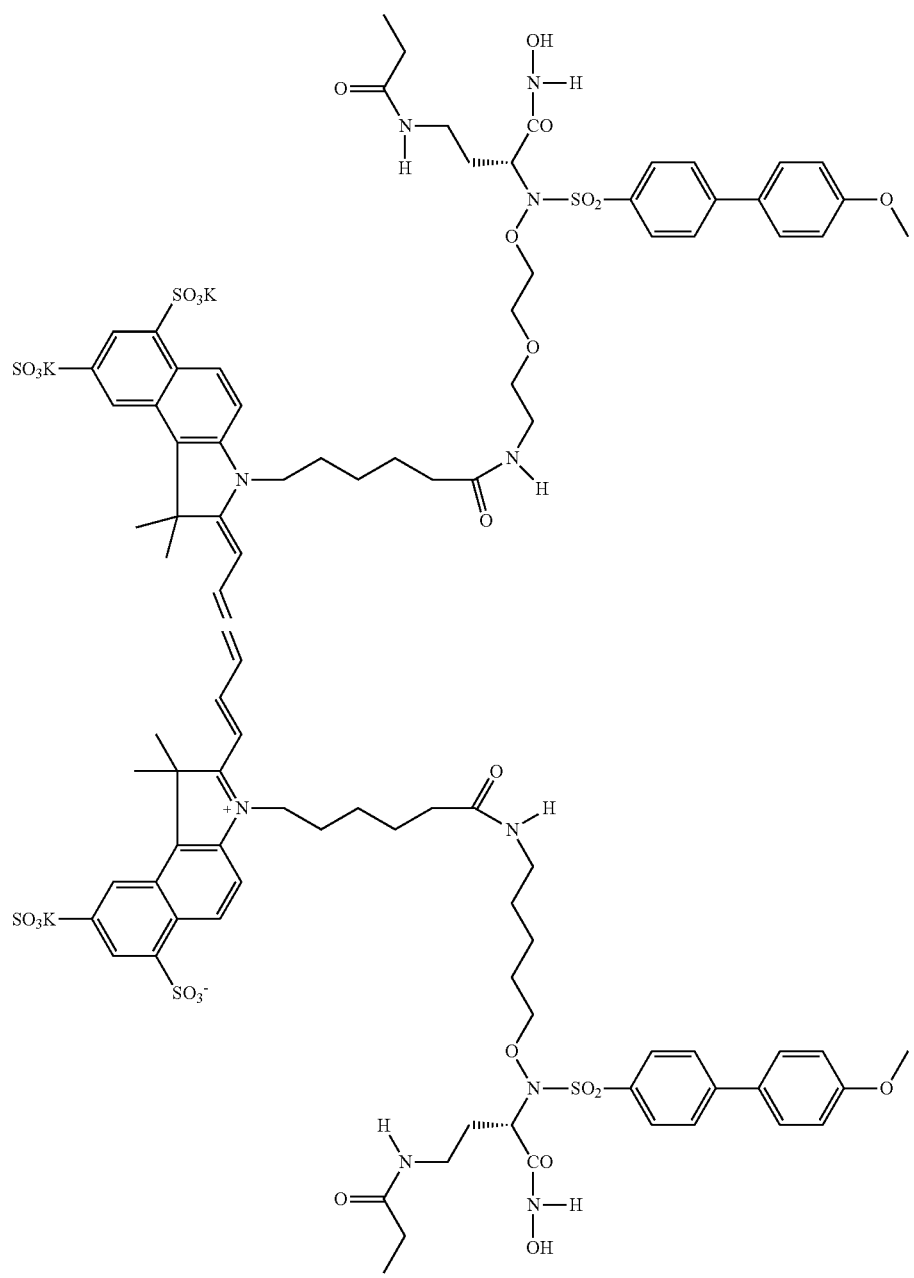
STAR10D

Scheme 11
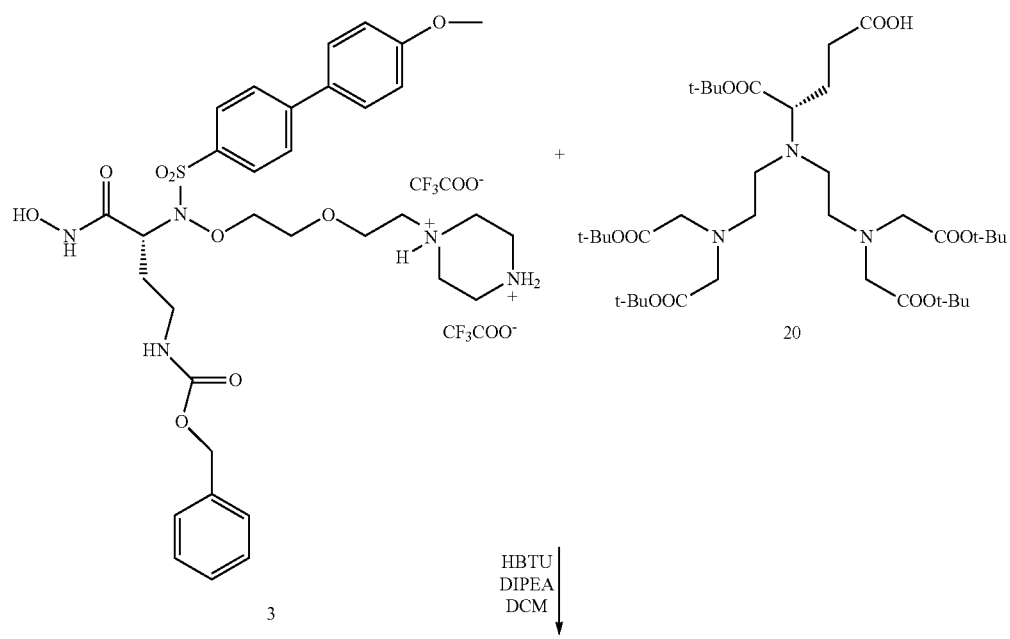
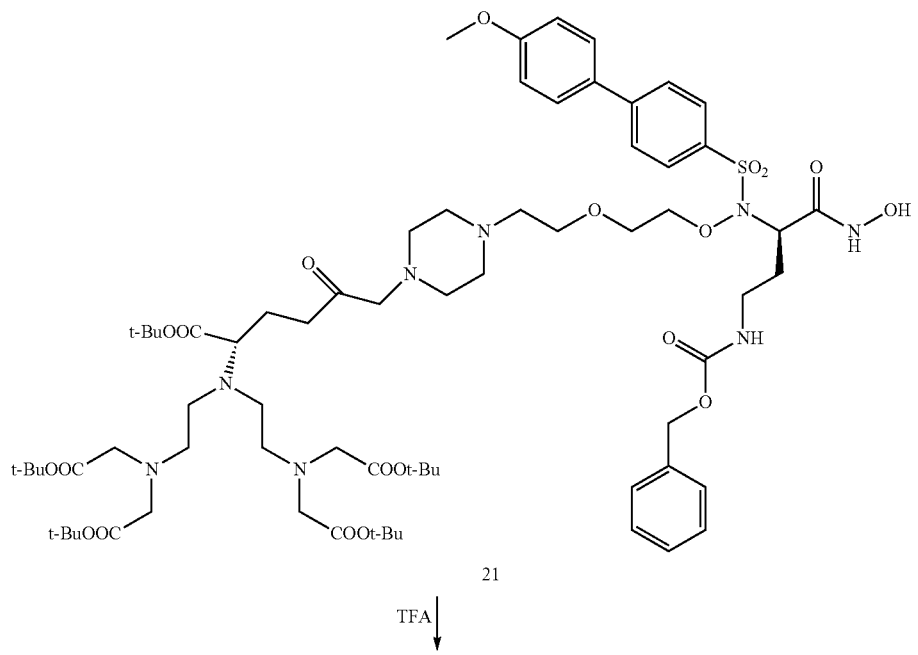

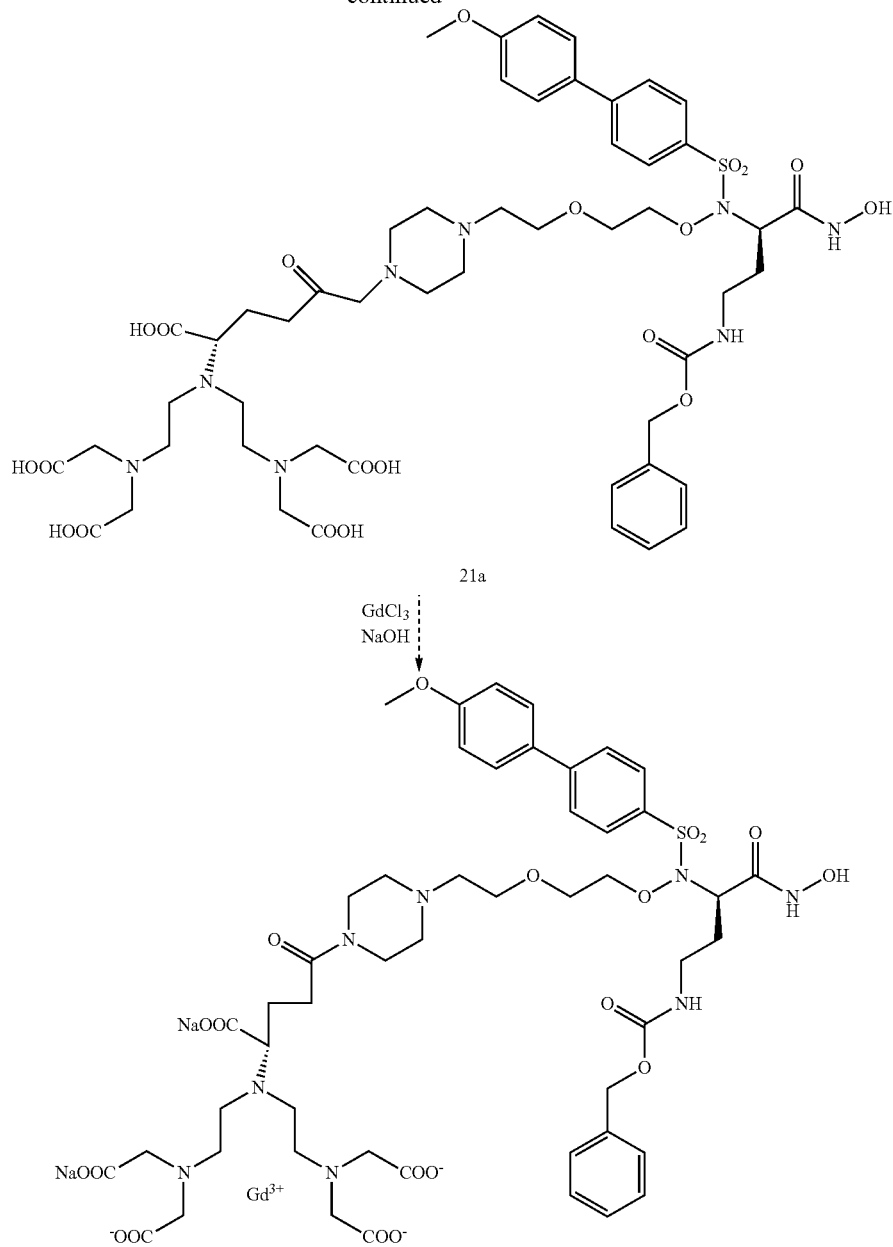

Example 1

Preparation of compound (1a): (R)-benzyl 3-(N-(benzyloxy)biphenyl-4-ylsulfonamido)-4-(hydroxyamino)-4-oxobutylcarbamate

Preparation of Compound (6)

A solution of (S)-(+)-Z-4-amino-2-hydroxybutyric acid (5) (5 g, 19.74 mmol) in toluene (38 mL) containing N,N-dimethylformamide di-tert-butyl acetal (18.92 mL, 78.96 mmol) was heated to 95° C. for 3 h. The solvent was then evaporated and the crude product was purified by flash chromatography on silica gel (n-hexane/EtOAc=7:4) to give (6) (3.4 g, 55.7% yields) as yellow solid.

Mp 42-44° C.; $[\alpha]^{20}_D = -5.9°$ (c=10.1 mg/ml, CHCl$_3$)
$^1$H-NMR (CDCl$_3$) δ: 1.47 (s, 9H); 1.76-1.85 (m, 1H); 1.94-2.09 (m, 1H); 2.74 (br s, 1H); 3.36 (dd, J=6.04 Hz, J=11.99 Hz, 2H); 4.10 (dd, J=4.02 Hz, J=8.05 Hz, 1H); 5.09 (s, 2H); 5.21 (br s, 1H); 7.31-7.37 (m, 5H)
Anal. Calcd. for C$_{16}$H$_{23}$NO$_5$: C, 62.12; H, 7.49; N, 4.53. Found: C, 62.22; H, 7.48; N, 4.53.

Preparation of Compound (7)

A solution of biphenyl-4-sulfonyl chloride (56) (3.17 g, 12.53 mmol) in anhydrous THF (32 mL) was added dropwise to a stirred and cooled (0° C.) solution of O-benzyl-hydroxylamine hydrochloride (53) (2 g, 12.53 mmol) and N-methylmorpholine (2.75 mL, 25.06 mmol) in anhydrous THF (32 mL). After 30 min. under these conditions, the reaction mixture was stirred at rt for 3 days, then was diluted with AcOEt and washed with $H_2O$ giving, after work-up, sulfonamide (7) (3.62 g, 85%) as a white solid.

Mp=130-132° C.;

$^1$H-NMR (CDCl$_3$) δ: 5.01 (s, 2H); 7.01 (s, 1H); 7.35 (m, 5H); 7.44-7.51 (m, 3H); 7.57-7.62 (m, 2H); 7.70-7.75 (m, 2H); 7.97-8.01 (m, 2H).

Preparation of Compound (11)

Diisopropyl azodicarboxylate (DIAD) (1.28 mL, 6.52 mmol) was added dropwise to a solution containing the secondary alcohol (6) (0.8 g, 2.61 mmol), the sulfonamide (7) (1.3 g, 3.91 mmol) and triphenylphosphine (2.05 g, 7.83 mmol) in anhydrous THF (45 mL) under nitrogen atmosphere at 0° C. The resulting solution was stirred for 5 h at rt and evaporated under reduced pressure to afford a crude product, which was purified by flash chromatography on silica gel (n-hexane/EtOAc=3:1) to yield compound (11) (0.95 g, 58% yield) as pure yellow oil.

$^1$H-NMR (CDCl$_3$) δ: 1.25 (s, 9H); 1.90-2.04 (m, 2H); 3.16-3.40 (m, 2H); 4.16 (t, J=7.1 Hz, 1H); 4.93-5.00 (m, 1H); 5.07-5.19 (m, 4H); 7.33-7.37 (m, 10H); 7.41-7.59 (m, 5H); 7.66-7.70 (m, 2H); 7.92-7.97 (m, 2H).

$^{13}$C-NMR (CDCl$_3$) δ: 22.09; 27.87; 37.59; 62.75; 66.76; 80.87; 82.56; 127.43; 127.67; 128.16; 128.56; 128.72; 128.92; 129.14; 129.89; 129.94; 133.89; 134.80; 139.17; 146.84; 156.27.

Preparation of Compound (35)

Trifluoroacetic acid (0.9 mL, 57.00 mmol) was added dropwise to a stirred solution of tert-butyl ester (11) (136 mg, 0.21 mmol) in freshly distilled $CH_2Cl_2$ (1.0 mL), cooled to 0° C. The solution was stirred for 5 h at 0° C. and the solvent was removed in vacuo to give compound (35) (128 mg, 100% yield) as oil.

$^1$H-NMR (CDCl$_3$) δ: 1.60-1.70 (m, 1H); 1.88-2.08 (m, 1H); 3.19 (m, 2H); 4.30 (t, J=6.9 Hz, 1H); 5.02-5.17 (m, 4H); 7.28-7.34 (m, 10H); 7.40-7.51 (m, 3H); 7.55-7.59 (m, 2H); 7.65-7.70 (m, 2H); 7.91-7.95 (m, 2H).

Preparation of Compound (37)

To a solution of carboxylic acid (35) (117 mg, 0.2 mmol) and O-(tert-butyldimethyl-silyl)hydroxylamine (44 mg, 0.3 mmol) in freshly distilled $CH_2Cl_2$ (3.6 mL) cooled to 0° C., was added 1-[3-(dimethylamino)propyl]-3-ethyl carbodiimide hydrochloride (EDCI) portionwise (57.5 mg, 0.3 mmol). After stirring at rt for 20 h, the mixture was washed with $H_2O$ and the organic phase was dried and evaporated in vacuo. The residue was purified by flash chromatography on silica gel (n-hexane/EtOAc=2.5:1) to yield compound (37) (28 mg, 20% yield) as yellow oil.

$^1$H-NMR (CDCl$_3$) δ: 0.13 (s, 6H); 0.90 (s, 9H); 1.90-2.11 (m, 2H); 2.80-3.40 (m, 2H); 4.13-4.22 (m, 1H); 5.02-5.27 (m, 4H); 7.31-7.46 (m, 13H); 7.53-7.58 (m, 2H); 7.64-7.68 (m, 2H); 7.84-7.88 (m, 2H).

Preparation of the Title Compound (1a)

Trifluoroacetic acid (0.15 mL, 1.85 mmol) was added dropwise to a stirred solution of compound (37) (23 mg, 0.03 mmol) in freshly distilled $CH_2Cl_2$ (1 mL), cooled to 0° C. The solution was stirred for 5 h at 0° C. and the solvent was removed in vacuo to give a crude product that was recrystallized from $Et_2O$ and n-hexane to give (1a) (10 mg, 53% yield) as solid.

$^1$H-NMR (CDCl$_3$) δ: 1.99 (m, 2H); 3.00-3.35 (m, 2H); 4.29 (m, 1H); 5.08-5.26 (m, 4H); 7.34-7.45 (m, 13H); 7.53-7.58 (m, 2H); 7.66-7.70 (m, 2H); 7.87-7.91 (m, 2H).

Example 2

Preparation of compound (1b): (R)—N-(4-(hydroxyamino)-3-(N-isopropoxybiphenyl-4-ylsulfonamido)-4-oxobutyl)benzamide Preparation of Compound (8)

N-isopropoxy-1,1'-biphenyl-4-sulfonamide was prepared as previously described by Rossello, A. et al. (*Bioorg. Med. Chem.* 2004, 12, 2441).

Preparation of Compound (12)

Tert-butyl ester (12) was prepared from sulfonamide derivative (8) (1.08 g, 3.72 mmol) and alcohol (6) (0.76 g, 2.48 mmol) following the procedure previously described for the preparation of compound (11), as set forth in Example 1. The crude reaction mixture was purified by flash chromatography (n-hexane/AcOEt=5:1), to give (12) (1.14 g, 79% yield) as a yellow oil.

$[α]^{20}_D$=+55° (c=9.1 mg/L, CHCl$_3$);

$^1$H-NMR (CDCl$_3$) δ: 1.22-1.25 (m, 15H); 2.04 (m, 2H); 3.22-3.37 (m, 2H); 4.12 (dd, J=7.14 Hz, J=14.29 Hz, 1H); 4.43 (septet, J=6.2 Hz, 1H); 5.08 (s, 2H); 7.34 (m, 5H); 7.42-7.53 (m, 3H); 7.55-7.61 (m, 2H); 7.7-7.74 (m, 2H); 7.94-7.98 (m, 2H).

Preparation of Compound (15)

A solution of compound (12) (0.74 g, 1.27 mmol) in MeOH (80 mL) was stirred under hydrogen atmosphere in the presence of 10% Pd—C (0.20 g) and glacial acetic acid (80 mL) for 17 h at room temperature. The resulting mixture was filtered on celite and the filtrate was evaporated under reduced pressure to give (15) (0.60 g, 93% yield) as a brownish oil.

$^1$H-NMR (CDCl3) δ: 1.10 (brs, 9H); 1.20 (t, J=4.4 Hz, 6H); 2.16-2.30 (m, 2H); 3.16 (m, 2H); 4.34-4.46 (m, 2H); 7.40-7.51 (m, 3H); 7.56-7.59 (m, 2H); 7.71-7.75 (m, 2H); 8.00-8.04 (m, 2H).

$^{13}$C-NMR (CDCl3) δ: 21.15; 21.22; 27.72; 36.70; 62.97; 80.03; 82.49; 127.03; 127.45; 127.59; 127.76; 128.67; 129.14; 130.49; 133.60; 139.30; 146.89.

Preparation of Compound (17)

A solution of compound (15) (0.30 g, 0.59 mmol) in dry DMF (6 mL) was treated with benzoyl chloride (0.08 mL, 0.70 mmol) and i-Pr$_2$NEt (0.20 mL, 1.18 mmol). The reaction mixture was stirred at rt for 17 h, then was diluted with ethyl acetate, washed with $H_2O$, dried over $Na_2SO_4$ and evaporated. The crude was purified by flash chromatography (n-hexane/AcOEt=2.5:1), to give (17) (112 mg, 34% yield) as a yellow oil.

$^1$H-NMR (CDCl$_3$) δ: 1.13 (brs, 9H); 1.23 (d, J=5.1 Hz, 3H); 1.26 (d, J=4.4 Hz, 3H); 2.10-2.21 (m, 2H); 3.34-3.50 (m, 1H); 3.80-3.92 (m, 1H); 4.23 (t, J=7.1 Hz, 1H); 4.45 (septet, 1H); 7.39-7.59 (m, 10H); 7.69-7.73 (m, 2H); 7.93-7.98 (m, 2H).

Preparation of Compound (23)

Carboxylic acid (23) (89 mg, 100% yield) was prepared from ester derivative (17) (0.10 g, 0.18 mmol) following the procedure previously described for the preparation of compound (35), as per Example 1.

$^1$H-NMR (CDCl$_3$) δ: 1.20 (t, J=5.1 Hz, 6H); 1.80-2.28 (m, 2H); 3.40-3.55 (m, 1H); 3.60-3.82 (m, 1H); 4.30-4.50 (m, 2H); 6.56 (brs, 1H); 7.43-7.58 (m, 10H); 7.66-7.69 (m, 2H); 7.91-7.94 (m, 2H).

Preparation of Compound (29)

Following an analogous procedure to that used for the preparation of compound (37), in Example 1, carboxylic acid (23) (90 mg, 0.18 mmol) was coupled with O-(tert-butyldimethyl-silyl)hydroxylamine. Silica gel column chromatography (n-hexane/AcOEt=2:1) yielded the desired product (30 mg, 27% yield).

$^1$H-NMR (CDCl$_3$) δ: 0.16 (s, 6H); 0.93 (s, 9H); 1.22 (d, J=6.2 Hz, 3H); 1.28 (d, J=6.2 Hz, 3H); 2.02-2.16 (m, 2H); 3.20 (m, 1H); 3.43 (m, 1H); 4.06-4.20 (m, 1H); 4.46 (septet, 1H); 6.76 (brs, 1H); 7.35-7.65 (m, 10H); 7.73-7.77 (m, 2H); 7.87-7.91 (m, 2H); 9.01 (brs, 1H).

Preparation of the Title Compound (1b)

Following a procedure analogous to that used for the preparation of compound (1a), in Example 1, tert-butyl O-silylate (29) (30 mg, 0.05 mmol) was treated with TFA to give the desired hydroxamic acid (15 mg, 60.5% yield) after recrystallization from Et$_2$O.

$^1$H-NMR (CDCl$_3$) δ: 1.24 (t, J=6.5 Hz, 6H); 1.44-1.69 (m, 1H); 2.05-2.21 (m, 1H); 3.10-3.50 (m, 2H); 4.20-4.50 (m, 2H); 7.10 (brs, 1H); 7.30-7.55 (m, 10H); 7.59-7.63 (m, 2H); 7.86-7.90 (m, 2H).

Example 3

Preparation of compound (1c): (R)—N-hydroxy-2-(N-isopropoxybiphenyl-4-ylsulfonamido)-4-(methylsulfonamido)butanamide

Preparation of Compound (18)

A solution of compound (15) prepared according to Example 2 (0.30 g, 0.60 mmol), in dry THF (3 mL), was treated with methanesulfonyl chloride (0.05 mL, 0.60 mmol) and N-methylmorpholine (0.13 mL, 1.2 mmol). The reaction mixture was stirred at room temperature overnight, then was diluted with AcOEt, washed with H$_2$O, dried over Na$_2$SO$_4$ and evaporated. The crude was purified by flash chromatography (n-hexane/AcOEt=3:2), to give (18) (100 mg, 32% yield) as a yellow oil.

$^1$H-NMR (CDCl$_3$) δ: 1.14 (brs, 9H); 1.20-1.26 (m, 6H); 2.04 (brs, 2H); 2.95 (s, 3H); 3.29 (brs, 2H); 4.25 (t, J=7.1 Hz, 1H); 4.42 (septet, 1H); 7.43-7.54 (m, 3H); 7.58-7.62 (m, 2H); 7.74-7.78 (m, 2H); 7.96-8.00 (m, 2H).

Preparation of Compound (24)

Following a procedure analogous to that used for the preparation of compound (35), in Example 1, ester derivative (18) (100 mg, 0.19 mmol) was treated with TFA to give the desired carboxylic acid (24) (73 mg, 79% yield), after recrystallization from Et$_2$O and n-hexane.

$^1$H-NMR (CDCl$_3$) δ: 1.22 (d, J=6.2 Hz, 6H); 2.06-2.17 (m, 2H); 2.91 (s, 3H); 3.21 (brs, 2H); 4.34-4.44 (m, 2H); 7.42-7.53 (m, 3H); 7.61-7.66 (m, 2H); 7.74-7.78 (m, 2H); 7.95-7.99 (m, 2H).

Preparation of Compound (30)

Following a procedure analogous to that used for the preparation of compound (37), in Example 1, carboxylic acid (24) (70 mg, 0.15 mmol) was coupled with O-(tert-butyldimethylsilyl)hydroxylamine. Silica gel column chromatography (n-hexane/AcOEt=1:1) yielded the desired product (32 mg, 33% yield).

$^1$H-NMR (CDCl$_3$) δ: 0.15 (s, 6H); 0.93 (s, 9H); 1.20 (d, J=6.2 Hz, 3H); 1.25 (d, J=5.8 Hz, 3H); 2.00-2.15 (m, 2H); 2.83 (s, 3H); 2.89-2.99 (m, 2H); 4.23-4.29 (m, 1H); 4.40 (septet, 1H); 7.42-7.52 (m, 3H); 7.61-7.66 (m, 2H); 7.79-7.83 (m, 2H); 7.96-8.00 (m, 2H); 8.64 (brs, 1H).

Preparation of the Title Compound (1c)

Following a procedure analogous to that used for the preparation of the compound (1a), in Example 1, tert-butyl O-silylate (30) (30 mg, 0.05 mmol) was treated with TFA to give the desired hydroxamic acid (15 mg, 60% yield), after recrystallization from Et$_2$O and n-hexane.

$^1$H-NMR (CDCl$_3$) δ: 1.24 (t, J=6.4 Hz, 6H); 2.01-2.18 (m, 2H); 2.88 (s, 3H); 3.00-3.20 (m, 2H); 4.40-4.48 (m, 2H); 4.88 (brs, 1H); 7.42-7.53 (m, 3H); 7.62-7.66 (m, 2H); 7.78-7.83 (m, 2H); 7.95-7.99 (m, 2H).

Example 4

Preparation of compound (1d): (R)-4-acetamido-N-hydroxy-2-(N-isopropoxybiphenyl-4-ylsulfonamido)butanamide

Preparation of Compound (19)

Following a procedure analogous to that used for the preparation of compound (17), in Example 2, ester derivative (15) (0.30 g, 0.59 mmol) was acylated with acetyl chloride. Silica gel column chromatography (n-hexane/AcOEt=1:1) yielded the desired product (19) (60 mg, 22% yield).

$^1$H-NMR (CDCl$_3$) δ: 1.19-1.24 (m, 15H); 1.90-2.01 (m, 5H); 3.13-3.23 (m, 1H); 3.53 (m, 1H); 4.12 (m, 1H); 4.40 (septet, 1H); 6.11 (brs, 1H); 7.41-7.52 (m, 3H); 7.57-7.61 (m, 2H); 7.72-7.76 (m, 2H); 7.94-7.98 (m, 2H).

$^{13}$C-NMR (CDCl$_3$) δ: 21.17; 23.48; 27.76; 36.17; 63.59; 79.80; 82.25; 127.39; 127.52; 128.72; 129.16; 130.14; 133.80; 139.19; 146.84; 170.22.

Preparation of Compound (25)

Following a procedure analogous to that used for the preparation of compound (35), in Example 1, ester derivative (19) (60 mg, 0.12 mmol) was treated with TFA to give the desired carboxylic acid (25) (60 mg, 100% yield).

$^1$H-NMR (CDCl$_3$) δ: 1.16 (d, J=2.01, 3H); 1.19 (d, J=2.01, 3H); 1.92-2.10 (m, 5H); 3.15-3.60 (m, 2H); 4.20-4.39 (m, 2H); 6.73 (brs, 1H); 7.42-7.52 (m, 3H); 7.59-7.63 (m, 2H); 7.73-7.77 (m, 2H); 7.93-7.97 (m, 2H); 10.24 (brs, 1H).

Preparation of Compound (31)

Following a procedure analogous to that used for the preparation of compound (37), in Example 1, carboxylic acid (25) (60 mg, 0.14 mmol) was coupled with O-(tert-butyldimethylsilyl)hydroxylamine. Silica gel column chromatography (n-hexane/AcOEt=1:2) yielded the desired product (12 mg, 16% yield).

$^1$H-NMR (CDCl$_3$) δ: 0.15 (s, 6H); 0.93 (s, 9H); 1.21 (d, J=6.2 Hz, 3H); 1.25 (d, J=6.2 Hz, 3H); 1.90-2.05 (m, 5H); 2.80-3.26 (m, 2H); 4.06-4.16 (m, 1H); 4.44 (septet, 1H); 5.95 (brs, 1H); 7.42-7.53 (m, 3H); 7.58-7.65 (m, 2H); 7.76-7.80 (m, 2H); 7.92-7.96 (m, 2H); 8.90 (brs, 1H).

Preparation of the Title Compound (1d)

Following a procedure analogous to that used for the preparation of compound (1a), in Example 1, tert-butyl O-silylate (31) (12 mg, 0.02 mmol) was treated with TFA to give the desired hydroxamic acid (11 mg, 90% yield).

$^1$H-NMR (CDCl$_3$) δ: 1.23 (d, J=6.7, 6H); 1.90-2.08 (m, 5H); 3.04-3.35 (m, 2H); 4.22 (m, 1H); 4.40 (septet, 1H); 6.73 (brs, 1H); 7.42-7.52 (m, 3H); 7.59-7.63 (m, 2H); 7.76-7.80 (m, 2H); 7.92-7.96 (m, 2H).

Example 5

Preparation of compound (1e): (R)—N-hydroxy-2-(N-isopropoxybiphenyl-4-ylsulfonamido)-4-(2-phenylacetamido)butanamide Preparation of Compound (20)

Following a procedure analogous to that used for the preparation of compound (17), in Example 2, ester derivative (15) (0.30 g, 0.59 mmol) was acylated with phenylacetyl chloride. Silica gel column chromatography (n-hexane/AcOEt=2:1) yielded the desired product (55 mg, 16% yield).

$^1$H-NMR (CDCl$_3$) δ: 1.10-1.22 (m, 15H); 1.81-2.05 (m, 2H); 3.00-3.21 (m, 1H); 3.50-3.60 (m, 3H); 3.96 (t, J=7.5 Hz, 1H); 4.38 (septet, 1H); 7.28-7.37 (m, 5H); 7.43-7.54 (m, 3H); 7.57-7.62 (m, 2H); 7.68-7.73 (m, 2H); 7.80-7.84 (m, 2H).

Preparation of Compound (26)

Following a procedure analogous to that used for the preparation of compound (35), in Example 1, ester derivative (20) (55 mg, 0.09 mmol) was treated with TFA to give the desired carboxylic acid (26) (53 mg, 100% yield).

$^1$H-NMR (CDCl$_3$) δ: 1.14 (d, J=3.4, 3H); 1.17 (d, J=3.4, 3H); 1.93-2.10 (m, 2H); 3.14 (m, 1H); 3.47 (m, 1H); 3.61 (s, 2H); 4.13 (t, J=7.3 Hz, 1H); 4.33 (septet, 1H); 5.32 (brs, 1H); 6.14 (brs, 1H); 7.22-7.26 (m, 1H); 7.30-7.37 (m, 4H); 7.42-7.53 (m, 3H); 7.58-7.63 (m, 2H); 7.67-7.73 (m, 2H); 7.82-7.86 (m, 2H).

Preparation of Compound (32)

Following a procedure analogous to that used for the preparation of compound (37), in Example 1, carboxylic acid (26) (53 mg, 0.10 mmol) was coupled with O-(tert-butyldimethylsilyl)hydroxylamine to give compound (32) (54 mg, 80% yield).

Preparation of the Title Compound (1e)

Following a procedure analogous to that used for the preparation of compound (1a), in Example 1, tert-butyl O-silylate (32) (54 mg, 0.08 mmol) was treated with TFA to give the desired hydroxamic acid (30 mg, 68% yield), after recrystallization from Et$_2$O and n-hexane.

$^1$H-NMR (CDCl$_3$) δ: 1.18-1.32 (m, 6H); 1.83-2.22 (m, 2H); 3.10-3.28 (m, 2H); 3.48 (s, 2H); 4.11 (m, 1H); 4.39 (septet, 1H); 6.23 (brs, 1H); 7.16-7.36 (m, 5H); 7.43-7.47 (m, 3H); 7.57-7.61 (m, 2H); 7.67-7.72 (m, 2H); 7.86-7.90 (m, 2H).

Example 6

Preparation of compound (1f): (R)-4-acetamido-N-hydroxy-2-(N-isopropoxy-4'-methoxybiphenyl-4-ylsulfonamido)butanamide Preparation of Compound (9)

A solution of the commercially available 4'-methoxybiphenyl-4-yl sulfonyl chloride (1 g, 3.53 mmol) in anhydrous THF (8 mL) was added dropwise to a stirred and cooled (0° C.) solution of O-isopropylhydroxylamine hydrochloride (0.4 g, 3.53 mmol) and N-methylmorpholine (0.77 mL, 7.06 mmol) in anhydrous THF (8 mL). After 30 min under these conditions, the reaction mixture was stirred at room temperature for 3 days, then was diluted with AcOEt and washed with H$_2$O giving, after work-up, sulfonamide (9) (0.94 g, 83% yield) as a white solid.

Mp=162-163° C.;

$^1$H-NMR (CDCl$_3$) δ: 1.20 (d, J=6.2 Hz, 6H); 3.86 (s, 3H); 4.28 (septet, J=6.0 Hz, 1H); 6.80 (s, 1H); 6.97-7.04 (m, 2H); 7.53-7.60 (m, 2H); 7.68-7.72 (m, 2H); 7.93-7.97 (m, 2H).

Preparation of Compound (13)

Tert-butyl ester (13) was prepared from sulfonamide (9) (482 mg, 1.5 mmol) and alcohol (6) (310 mg, 1.0 mmol) following the procedure previously described for the preparation of compound (11), in Example 1. The crude reaction mixture was purified by flash chromatography (n-hexane/AcOEt=5:2), to give (13) (455 mg, 74% yield) as a yellow oil.

$^1$H-NMR (CDCl$_3$) δ: 1.21-1.32 (m, 15H); 1.90-2.10 (m, 2H); 3.10-3.50 (m, 2H); 3.86 (s, 3H); 4.06-4.16 (m, 1H); 4.43 (septet, J=6.2 Hz, 1H); 5.08 (s, 2H); 6.97-7.02 (m, 2H); 7.34 (m, 5H); 7.51-7.56 (m, 2H); 7.65-7.70 (m, 2H); 7.90-7.94 (m, 2H).

Preparation of Compound (16)

Following a procedure analogous to that used for the preparation of compound (15), ester (13) (450 mg, 0.73 mmol) was hydrogenated in the presence of 10% Pd—C to give (16) (428 mg, 100% yield).

$^1$H-NMR (CDCl$_3$) δ: 1.15-1.27 (m, 15H); 2.04-2.10 (m, 2H); 3.06 (m, 2H); 3.86 (s, 3H); 4.27 (m, 1H); 4.41 (septet, J=6.2 Hz, 1H); 6.98-7.02 (m, 2H); 7.52-7.56 (m, 2H); 7.68-7.72 (m, 2H); 7.95-7.99 (m, 2H).

Preparation of Compound (21)

Following a procedure analogous to that used for the preparation of compound (17), in Example 2, ester (16) (215 mg, 0.40 mmol) was acylated with acetyl chloride. Silica gel column chromatography (n-hexane/AcOEt=2:3) yielded the desired product (86 mg, 42% yield).

$^1$H-NMR (CDCl$_3$) δ: 1.19-1.25 (m, 15H); 1.90-2.04 (m, 5H); 3.13-3.50 (m, 2H); 3.87 (s, 3H); 4.12 (m, 1H); 4.41

(septet, 1H); 6.99-7.03 (m, 2H); 7.53-7.57 (m, 2H); 7.69-7.73 (m, 2H); 7.91-7.95 (m, 2H).

Preparation of Compound (27)

Following a procedure analogous to that used for the preparation of compound (35), in Example 1, ester (21) (81 mg, 0.15 mmol) was treated with TFA to give the desired carboxylic acid (27) (50 mg, 67% yield), after recrystallization from $Et_2O$ and n-hexane.

$^1$H-NMR ($CDCl_3$) δ: 1.15-1.22 (m, 6H); 1.88-2.05 (m, 5H); 3.19-3.35 (m, 2H); 3.84 (s, 3H); 4.24 (t, 1H); 4.37 (septet, 1H); 6.30 (brs, 1H); 6.96-7.00 (m, 2H); 7.53-7.58 (m, 2H); 7.67-7.71 (m, 2H); 7.89-7.94 (m, 2H).

Preparation of Compound (33)

Following a procedure analogous to that used for the preparation of compound (37), in Example 1, carboxylic acid (27) (50 mg, 0.10 mmol) was coupled with O-(tert-butyldimethylsilyl)hydroxylamine. Silica gel column chromatography (n-hexane/AcOEt=1:2) yielded the desired product (45 mg, 71% yield).

$^1$H-NMR ($CDCl_3$) δ: 0.15 (s, 6H); 0.92 (s, 9H); 1.23-1.27 (m, 6H); 1.91-2.00 (m, 5H); 3.00-3.20 (m, 2H); 3.87 (s, 3H); 4.06-4.13 (m, 1H); 4.43 (septet, 1H); 5.89 (brs, 1H); 6.98-7.03 (m, 2H); 7.56-7.60 (m, 2H); 7.72-7.76 (m, 2H); 7.88-7.93 (m, 2H); 8.80 (brs, 1H).

Preparation of the Title Compound (1f)

Following a procedure analogous to that used for the preparation of compound (1a), tert-butyl O-silylate (33) (43 mg, 0.07 mmol) was treated with TFA to give the desired hydroxamic acid (31 mg, 90% yield), after recrystallization from $Et_2O$ and n-hexane.

Mp=83-85° C.;

$^1$H-NMR ($CDCl_3$) δ: 1.20-1.26 (m, 6H); 1.94-2.04 (m, 5H); 3.02-3.40 (m, 2H); 3.86 (s, 3H); 4.22 (m, 1H); 4.45 (septet, 1H); 6.09 (brs, 1H); 6.98-7.02 (m, 2H); 7.55-7.59 (m, 2H); 7.71-7.75 (m, 2H); 7.89-7.94 (m, 2H).

Example 7

Preparation of compound (1g): (R)—N-hydroxy-2-(N-isopropoxy-4'-methoxybiphenyl-4-ylsulfonamido)-4-(2-phenylacetamido)butanamide Preparation of Compound (22)

Following a procedure analogous to that used for the preparation of compound (17), in Example 2, ester (16) (200 mg, 0.37 mmol) was acylated with phenylacetyl chloride. Silica gel column chromatography (n-hexane/AcOEt=3:2) yielded the desired product (53 mg, 24% yield).

$^1$H-NMR ($CDCl_3$) δ: 1.16-1.25 (m, 15H); 1.90-2.05 (m, 2H); 3.12 (m, 2H); 3.57 (s, 2H); 3.87 (s, 3H); 3.94 (t, J=7.5 Hz, 1H); 4.37 (septet, 1H); 6.98-7.04 (m, 2H); 7.31-7.37 (m, 5H); 7.52-7.57 (m, 2H); 7.64-7.68 (m, 2H); 7.77-7.81 (m, 2H).

Preparation of Compound (28)

Following a procedure analogous to that used for the preparation of compound (35), in Example 1, ester (22) (48 mg, 0.08 mmol) was treated with TFA to give the desired carboxylic acid (28) (46 mg, 100% yield).

$^1$H-NMR ($CDCl_3$) δ: 1.15 (d, J=1.8 Hz, 3H); 1.18 (d, J=1.8 Hz, 3H); 1.93-2.10 (m, 2H); 3.10 (m, 2H); 3.56 (s, 2H); 3.86 (s, 3H); 4.15 (m, 1H); 4.37 (septet, 1H); 6.98-7.02 (m, 2H); 7.30-7.39 (m, 5H); 7.54-7.58 (m, 2H); 7.63-7.67 (m, 2H); 7.80-7.84 (m, 2H).

Preparation of Compound (34)

Following a procedure analogous to that used for the preparation of compound (37), in Example 1, carboxylic acid (28) (42 mg, 0.07 mmol) was coupled with O-(tert-butyldimethylsilyl)hydroxylamine. Silica gel column chromatography (n-hexane/AcOEt=2:1) yielded the desired product (17 mg, 32% yield).

$^1$H-NMR ($CDCl_3$) δ: 0.15 (s, 6H); 0.92 (s, 9H); 1.17-1.25 (m, 6H); 1.91-1.95 (m, 2H); 3.00-3.20 (m, 2H); 3.50 (s, 2H); 3.87 (s, 3H); 4.01-4.06 (m, 1H); 4.39 (septet, 1H); 5.75 (brs, 1H); 6.98-7.02 (m, 2H); 7.21-7.34 (m, 5H); 7.54-7.59 (m, 2H); 7.67-7.71 (m, 2H); 7.82-7.87 (m, 2H).

Preparation of the Title Compound (1g)

Following a procedure analogous to that used for the preparation of compound (1a), tert-butyl O-silylate (34) (15 mg, 0.02 mmol) was treated with TFA to give the desired hydroxamic acid (10 mg, 77% yield), after recrystallization from $Et_2O$ and n-hexane.

$^1$H-NMR ($CDCl_3$) δ: 1.19-1.22 (m, 6H); 1.94-1.98 (m, 2H); 3.00-3.20 (m, 2H); 3.51 (s, 2H); 3.86 (s, 3H); 4.10-4.16 (m, 1H); 4.41 (septet, 1H); 5.89 (brs, 1H); 6.97-7.01 (m, 2H); 7.21-7.32 (m, 5H); 7.53-7.57 (m, 2H); 7.65-7.69 (m, 2H); 7.83-7.87 (m, 2H).

Example 8

Preparation of compound (1h): (R)-benzyl 4-(hydroxyamino)-4-oxo-3-(N-(2-(2-(piperazin-1-yl)ethoxy)ethoxy)biphenyl-4-ylsulfonamido)butylcarbamate Preparation of Compound (61)

To a solution of 1-[2-(2-hydroxyethoxy)ethyl]piperazine (60) (5.0 g, 28.7 mmol) in $CH_2Cl_2$ (20 mL) wad added dropwise a solution of di-tert-butyldicarbonate (6.9 g, 31.5 mmol) in $CH_2Cl_2$ (20 mL) at 0° C. After stirring at room temperature for 12 h, the solution was diluted with $Et_2O$, washed with a saturated solution of $NaHCO_3$, with brine, dried ($Na_2SO_4$) and concentrated to yield the Boc-protected derivative (61) (7.2 g, 92% yield).

$^1$H-NMR ($CDCl_3$) δ: 1.43 (s, 9H); 2.45 (t, J=4.9 Hz, 4H); 2.57 (t, J=5.3 Hz, 2H); 3.44 (t, J=5.1 Hz, 4H); 3.56-3.67 (m, 6H); 4.17 (t, J=5.6 Hz, 1H).

$^{13}$C-NMR ($CDCl_3$) δ: 28.47; 43.46; 53.16; 57.97; 61.86; 67.69; 72.44; 79.69; 155.00

Preparation of Compound (62)

Diethyl azodicarboxylate (DEAD) (2.15 mL, 13.65 mmol) was added dropwise to a solution containing alcohol (61) (2.50 g, 9.10 mmol), N-hydroxyphthalimide (1.48 g, 9.10 mmol) and triphenylphosphine (3.58 g, 13.6 mmol) in anhydrous THF (100 mL), under nitrogen atmosphere. The resulting solution was stirred overnight at rt and evaporated under reduced pressure to afford a crude product, which was purified by flash chromatography on silica gel (n-hexane/AcOEt=4:1) to yield (62) (4.30 g, 98% yield) as a pure yellow oil.

$^1$H-NMR (CDCl$_3$) δ: 1.44 (s, 9H); 2.38 (t, J=4.9 Hz, 4H); 2.50 (t, J=5.6 Hz, 2H); 3.39 (t, J=5.3 Hz, 4H); 3.64 (t, J=5.6 Hz, 2H); 3.82 (t, J=4.2 Hz, 2H); 4.37 (t, J=4.3 Hz, 2H); 7.72-7.86 (m, 4H).

Preparation of Compound (55)

Hydrazine hydrate (1.73 mL, 35.87 mmol) was added to a solution of compound (62) (4.30 g, 10.25 mmol) in ethanol (210 mL). After stirring at room temperature for 14 h the mixture was filtered and the filtrate concentrated. The residue was diluted with AcOEt, the precipitate was removed by filtration and the filtrate was evaporated to yield the desired O-alkylhydroxylamine (55) (2.15 g, 72.6% yield).

$^1$H-NMR (CDCl$_3$) δ: 1.45 (s, 9H); 2.45 (t, J=4.9 Hz, 4H); 2.61 (t, J=5.8 Hz, 2H); 3.43 (t, J=5.1 Hz, 4H); 3.58-3.65 (m, 4H); 3.80-3.85 (m, 2H).

Preparation of Compound (10)

Following a procedure analogous to that used for the preparation of compound (7), in Example 1, O-alkylhydroxylamine (55) (2.85 g, 9.86 mmol) was reacted with biphenyl-4-sulfonyl chloride (56). Silica gel column chromatography (AcOEt) yielded the desired sulfonamide (3.05 g, 61% yield).

$^1$H-NMR (CDCl$_3$) δ: 1.44 (s, 9H); 2.44 (t, J=4.9 Hz, 4H); 2.58 (t, J=5.6 Hz, 2H); 3.43 (t, J=5.3 Hz, 4H); 3.61 (t, J=5.5 Hz, 2H); 3.67-3.71 (m, 2H); 4.10-4.15 (m, 2H); 7.41-7.53 (m, 3H); 7.58-7.63 (m, 2H); 7.71-7.75 (m, 2H); 7.97-8.01 (m, 2H).

Preparation of Compound (14)

Tert-butyl ester (14) was prepared from sulfonamide (10) (1.18 g, 2.33 mmol) and alcohol (6) following the procedure previously described for the preparation of compound (11), in Example 1. The crude reaction mixture was purified by flash chromatography (n-hexane/AcOEt=1:5), to give the desired product (1.39 g, 75% yield) as a yellow oil.

$^1$H-NMR (CDCl$_3$) δ: 1.33 (s, 9H); 1.43 (s, 9H); 1.74-1.98 (m, 2H); 2.42 (m, 4H); 2.58 (t, J=5.3 Hz, 2H); 3.12-3.26 (m, 2H); 3.40 (m, 4H); 3.56-3.65 (m, 4H); 4.09-4.41 (m, 3H); 5.05 (s, 2H); 5.22 (br s, 1H); 7.32 (m, 5H); 7.40-7.74 (m, 7H); 7.96-8.00 (m, 2H).

Preparation of Compound (36)

Following a procedure analogous to that used for the preparation of compound (35), in Example 1, ester (14) (1.39 g, 1.74 mmol) was treated with TFA to give the desired carboxylic acid (36) (1.30 g, 86% yield), after recrystallization from Et$_2$O.

$^1$H-NMR (CDCl$_3$) δ: 1.80-2.05 (m, 2H); 3.19-3.29 (m, 6H); 3.40 (m, 4H); 3.62 (m, 10H); 4.15 (m, 2H); 4.29 (t, J=6.5 Hz, 1H); 5.01 (s, 2H); 5.35 (brs, 1H); 7.29 (m, 5H); 7.43-7.52 (m, 3H); 7.57-7.63 (m, 2H); 7.70-7.74 (m, 2H); 7.90-7.94 (m, 2H).

Preparation of the Title Compound (1h)

Following a procedure analogous to that used for the preparation of compound (37), in Example 1, carboxylic acid (36) (0.14 g, 0.16 mmol) was coupled with O-(tert-butyldimethylsilyl)hydroxylamine. Silica gel column chromatography (CHCl$_3$/MeOH=9:1) yielded the desired hydroxamic acid (13 mg, 12% yield).

$^1$H-NMR (CDCl$_3$) δ: 1.80-2.00 (m, 2H); 2.47-3.17 (m, 16H); 4.13 (m, 3H); 4.92 (s, 2H); 6.25 (brs, 1H); 7.18 (m, 5H); 7.38-7.64 (m, 7H); 7.96 (m, 2H).

Example 9

Preparation of compound (2): (R)-4-(1,3-dioxoisoindolin-2-yl)-N-hydroxy-2-(N-isopropoxy-4'-methoxybiphenyl-4-ylsulfonamido)butanamide Preparation of Compound (40)

Following a procedure analogous to that used for the preparation of compound (6), in Example 1, (S)-α-hydroxy-1,3-dioxo-2-isoindolinebutyric acid (39) (1.0 g, 4.0 mmol) was treated with N,N-dimethylformamide di-tert-butyl acetal. Silica gel column chromatography (n-hexane/AcOEt=3:2) yielded the desired ester (530 mg, 43% yield), as a white solid.

Mp=122-123° C.;

$^1$H-NMR (CDCl$_3$) δ: 1.46 (s, 9H); 1.87-2.23 (m, 2H); 3.02 (d, J=5.3 Hz, 1H); 3.86 (t, J=7.3 Hz, 2H); 4.07-4.16 (m, 1H); 7.69-7.75 (m, 2H); 7.80-7.87 (m, 2H).

Preparation of Compound (43)

Tert-butyl ester (43) was prepared from sulfonamide (9) (400 mg, 1.24 mmol) and alcohol (40) (250 mg, 0.82 mmol) following the procedure previously described for the preparation of compound (11). The crude reaction mixture was purified by flash chromatography (n-hexane/AcOEt=2:1), to give the desired product (217 mg, 43% yield).

$^1$H-NMR (CDCl$_3$) δ: 1.24-1.29 (m, 15H); 2.10-2.30 (m, 2H); 3.51-3.74 (m, 2H); 3.87 (s, 3H); 4.06-4.23 (m, 1H); 4.46 (septet, 1H); 6.98-7.03 (m, 2H); 7.52-7.88 (m, 10H).

Preparation of Compound (46)

Following a procedure analogous to that used for compound (35), ester (43) (205 mg, 0.33 mmol) was treated with TFA to give the desired carboxylic acid (46) (135 mg, 74% yield), after recrystallization from Et$_2$O.

Mp=185-187° C.;

$^1$H-NMR (CDCl$_3$) δ: 1.21 (d, J=6.2 Hz, 3H); 1.27 (d, J=6.2 Hz, 3H); 2.10-2.28 (m, 2H); 3.61 (m, 2H); 3.87 (s, 3H); 4.33 (m, 1H); 4.46 (septet, 1H); 6.98-7.02 (m, 2H); 7.50-7.54 (m, 4H); 7.65-7.85 (m, 6H).

Preparation of Compound (48)

Following a procedure analogous to that used for the preparation of compound (37), carboxylic acid (46) (130 mg, 0.23 mmol) was coupled with O-(tert-butyldimethylsilyl)hydroxylamine. Silica gel column chromatography (n-hexane/AcOEt=3:2) yielded the desired product (110 mg, 70% yield).

$^1$H-NMR (CDCl$_3$) δ: 0.26 (s, 6H); 1.00 (s, 9H); 1.23 (d, J=6.2 Hz, 3H); 1.30 (d, J=6.2 Hz, 3H); 2.15-2.30 (m, 2H); 3.30-3.60 (m, 2H); 3.89 (s, 3H); 4.03 (m, 1H); 4.43 (septet, 1H); 6.98-7.02 (m, 2H); 7.16 (m, 2H); 7.36-7.41 (m, 2H); 7.61 (m, 4H); 7.68-7.72 (m, 2H); 8.72 (brs, 1H).

Preparation of Compound (2)

Following a procedure analogous to that used for the preparation of compound (1a), tert-butyl O-silylate (48)

(100 mg, 0.14 mmol) was treated with TFA to give the desired hydroxamic acid (61 mg, 77%), after recrystallization from Et$_2$O and n-hexane.

Mp=75-76° C.;
$^1$H-NMR (CDCl$_3$) δ: 1.23 (d, J=6.2 Hz, 3H); 1.30 (d, J=6.2 Hz, 3H); 2.12-2.32 (m, 2H); 3.40-3.53 (m, 2H); 3.88 (s, 3H); 4.02-4.20 (m, 1H); 4.46 (septet, 1H); 6.98-7.02 (m, 2H); 7.29-7.39 (m, 2H); 7.42-7.46 (m, 2H); 7.63 (m, 4H); 7.72-7.76 (m, 2H).

Example 10

Preparation of compound (3) (R)-4-(1,3-dioxoisoindolin-2-yl)-N-hydroxy-2-(N-isopropoxy-4-phenoxyphenylsulfonamido)butanamide Preparation of Compound (41)

Following a procedure analogous to that used for the preparation of compound (7), O-isopropylhydroxylamine (54) (415 mg, 3.72 mmol) was reacted with 4-phenoxybenzenesulfonyl chloride (58) to give the desired sulfonamide (41) (989 mg, 86% yield).
$^1$H-NMR (CDCl$_3$) δ: 1.19 (d, J=6.2 Hz, 6H); 4.25 (septet, J=6.2 Hz, 1H); 6.71 (s, 1H); 7.03-7.10 (m, 4H); 7.19-7.27 (m, 1H); 7.38-7.46 (m, 2H); 7.83-7.88 (m, 2H).

Preparation of Compound (44)

Tert-butyl ester (44) was prepared from sulfonamide (41) (378 mg, 1.23 mmol) and alcohol (40) following the procedure previously described for compound (11). The crude reaction mixture was purified by flash chromatography (n-hexane/AcOEt=7:2), to give the desired product (253 mg, 51% yield).
$^1$H-NMR (CDCl$_3$) δ: 1.18-1.45 (m, 15H); 1.99-2.38 (m, 2H); 3.56-3.74 (m, 2H); 4.06-4.15 (m, 1H); 4.43 (septet, J=6.2 Hz, 1H); 6.94-6.98 (m, 2H); 7.09-7.12 (m, 2H); 7.21-7.28 (m, 2H); 7.39-7.47 (m, 2H); 7.67-7.83 (m, 5H).

Preparation of Compound (47)

Following a procedure analogous to that used for the preparation of compound (35), ester (44) (250 mg, 0.42 mmol) was treated with TFA to give the desired carboxylic acid (47) (164 mg, 71%), after recrystallization from Et$_2$O and n-hexane.
$^1$H-NMR (CDCl$_3$) δ: 1.20 (d, J=6.2 Hz, 3H); 1.25 (d, J=6.2 Hz, 3H); 2.10-2.30 (m, 2H); 3.55-3.75 (m, 2H); 4.25-4.35 (m, 1H); 4.44 (septet, J=6.2 Hz, 1H); 6.88-6.92 (m, 2H); 7.09-7.13 (m, 2H); 7.21-7.28 (m, 2H); 7.39-7.47 (m, 2H); 7.69-7.84 (m, 5H).

Preparation of Compound (49)

Following a procedure analogous to that used for the preparation of compound (37), carboxylic acid (47) (160 mg, 0.30 mmol) was coupled with O-(tert-butyldimethylsilyl)hydroxylamine to give the desired product (178 mg, 87% yield).
$^1$H-NMR (CDCl$_3$) δ: 0.26 (s, 6H); 1.00 (s, 9H); 1.21 (d, J=6.2 Hz, 3H); 1.26 (d, J=6.2 Hz, 3H); 2.10-2.31 (m, 2H); 3.40-3.65 (m, 2H); 3.90-4.10 (m, 1H); 4.40 (septet, J=6.2 Hz, 1H); 6.59 (brs, 1H); 7.08-7.13 (m, 2H); 7.22-7.30 (m, 2H); 7.41-7.49 (m, 2H); 7.58-7.62 (m, 2H); 7.69-7.83 (m, 5H).

Preparation of the Title Compound (3)

Following a procedure analogous to that used for the preparation of compound (1a), tert-butyl O-silylate (49) (170 mg, 0.25 mmol) was treated with TFA to give the desired hydroxamic acid (3) (97 mg, 68% yield), after recrystallization from Et$_2$O and n-hexane.
$^1$H-NMR (CDCl$_3$) δ: 1.22 (d, J=6.2 Hz, 3H); 1.26 (d, J=6.2 Hz, 3H); 2.07-2.28 (m, 2H); 3.43-3.65 (m, 2H); 4.05-4.20 (m, 1H); 4.44 (septet, J=6.2 Hz, 1H); 6.70-6.83 (m, 2H); 7.09-7.13 (m, 2H); 7.22-7.29 (m, 2H); 7.40-7.48 (m, 2H); 7.64-7.83 (m, 5H).

Example 11

Preparation of compound (4) (R)-4-(1,3-dioxoisoindolin-2-yl)-2-(4'-ethoxy-N-isopropoxybiphenyl-4-ylsulfonamido)-N-hydroxybutanamide Preparation of Compound (42)

Following a procedure analogous to that used for the preparation of compound (7), O-isopropylhydroxylamine (54) (436 mg, 3.91 mmol) was reacted with 4-bromobenzenesulfonyl chloride (59) to give the desired sulfonamide (42) (870 mg, 75%).
$^1$H-NMR (CDCl$_3$) δ: 1.18 (d, J=6.2 Hz, 6H); 4.25 (septet, J=6.2 Hz, 1H); 6.80 (s, 1H); 7.66-7.70 (m, 2H); 7.75-7.80 (m, 2H).

Preparation of Compound (45)

Tert-butyl ester (45) was prepared from sulfonamide (42) (864 mg, 2.94 mmol) and alcohol (40) following the procedure previously described for the preparation of compound (11). The crude reaction mixture was purified by flash chromatography (n-hexane/AcOEt=5:1), to give the desired product (720 mg, 63% yield).
$^1$H-NMR (CDCl$_3$) δ: 1.19-1.40 (m, 15H); 2.05-2.20 (m, 2H); 3.55-3.80 (m, 2H); 4.02-4.20 (m, 1H); 4.43 (septet, J=6.2 Hz, 1H); 7.60-7.76 (m, 6H); 7.80-7.87 (m, 2H).

Preparation of Compound (50)

A mixture of ester (45) (200 mg, 0.34 mmol), 4-ethoxyphenylboronic acid (96 mg, 0.58 mmol), Pd(PPh$_3$)$_4$ (20 mg, 0.017 mmol) and K$_3$PO$_4$ (166 mg, 0.78 mmol) in 4.5 mL dioxane/H$_2$O 5:1 was heated to 85° C. under nitrogen. After 2 h, the reaction mixture was diluted with sat. solution of NaHCO$_3$, extracted with ACOEt and dried over Na$_2$SO$_4$. The organic layer was concentrated in vacuo and the crude product was purified by flash chromatography on silica gel (n-hexane/AcOEt=4:1) to give (50) (193 mg, 88% yield).
$^1$H-NMR (CDCl$_3$) δ: 1.20-1.39 (m, 15H); 1.45 (t, J=6.9 Hz, 3H); 2.04-2.35 (m, 2H); 3.50-3.80 (m, 2H); 4.05-4.15 (m, 3H); 4.46 (septet, J=6.2 Hz, 1H); 6.97-7.01 (m, 2H); 7.51-7.88 (m, 10H).

Preparation of Compound (51)

Following a procedure analogous to that used for the preparation of compound (35), ester (50) (193 mg, 0.30 mmol) was treated with TFA to give the desired carboxylic acid (51) (150 mg, 87%), after recrystallization from Et$_2$O and n-hexane.
$^1$H-NMR (CDCl$_3$) δ: 1.21 (d, J=6.2 Hz, 3H); 1.24 (d, J=6.2 Hz, 3H); 1.46 (t, J=6.9 Hz, 3H); 2.10-2.30 (m, 2H);

3.50-3.75 (m, 2H); 4.10 (q, J=6.9 Hz, 2H); 4.22-4.50 (m, 2H); 6.97-7.01 (m, 2H); 7.48-7.53 (m, 4H); 7.65-7.85 (m, 6H).

Preparation of Compound (52)

Following a procedure analogous to that used for the preparation of compound (37), carboxylic acid (51) (140 mg, 0.25 mmol) was coupled with O-(tert-butyldimethylsilyl)hydroxylamine. Silica gel column chromatography (n-hexane/AcOEt=2:1) yielded the desired product (120 mg, 71% yield).
$^1$H-NMR (CDCl$_3$) δ: 0.26 (s, 6H); 1.00 (s, 9H); 1.23 (d, J=6.2 Hz, 3H); 1.30 (d, J=6.2 Hz, 3H); 1.47 (t, J=6.9 Hz, 3H); 2.10-2.30 (m, 2H); 3.30-3.60 (m, 2H); 3.90-4.05 (m, 1H); 4.11 (q, J=6.9 Hz, 2H); 4.43 (septet, J=6.2 Hz, 1H); 6.99-7.01 (m, 2H); 7.10-7.22 (m, 2H); 7.35-7.39 (m, 2H); 7.60-7.71 (m, 6H); 8.70 (brs, 1H).

Preparation of the title compound (4) Following a procedure analogous to that used for the preparation of compound (1a), tert-butyl O-silylate (52) (120 mg, 0.17 mmol) was treated with TFA to give the desired hydroxamic acid (4) (83 mg, 82%), after recrystallization from Et$_2$O and n-hexane.
$^1$H-NMR (CDCl$_3$) δ: 1.24 (d, J=6.2 Hz, 3H); 1.30 (d, J=6.2 Hz, 3H); 1.46 (t, J=6.9 Hz, 3H); 2.10-2.35 (m, 2H); 3.40-3.60 (m, 2H); 4.05-4.16 (m, 3H); 4.46 (septet, J=6.2 Hz, 1H); 6.96-7.01 (m, 2H); 7.31-7.44 (m, 4H); 7.63-7.75 (m, 6H).

Example 12

Preparation of compound (64): benzyl 3-(N-isopropoxybiphenyl-4-ylsulfonamido)propylcarbamate Carbamate (64) was prepared from sulfonamide (8) (400 mg, 1.37 mmol) and commercial alcohol (63) following the procedure previously described for the preparation of compound (11). The crude reaction mixture was purified by flash chromatography (n-hexane/AcOEt=3:1), to give the desired product (400 mg, 87% yield).
$^1$H-NMR (CDCl$_3$) δ: 1.23-1.27 (m, 8H); 1.76-1.89 (m, 2H); 3.30 (q, J=62 Hz, 2H); 4.54 (septet, J=6.2 Hz, 1H); 5.08 (s, 2H); 7.34 (m, 5H); 7.41-7.53 (m, 3H); 7.59-7.63 (m, 2H); 7.72-7.76 (m, 2H); 7.88-7.93 (m, 2H)

Example 13

Preparation of Compound (1i)

Preparation of Compound (65)

To a solution of compound (55) of example 8 (1.76 g; 6 mmol) in THF (15 ml) at 0° C. was added N-methylmorpholine (0.66 ml, 6 mmol) and a solution of 4'-methoxy[1,1'-biphenyl]-4-sulfonyl chloride (1.69 g, 6 mmol) in THF (15 ml). The reaction mixture was stirred at room temperature for 3 days, then concentrated. The residue was taken up with ethyl acetate, washed with water and the organic phase was concentrated to obtain an orange oil. The crude product was purified by flash chromatography (EtOAc) to give compound (65) as a yellow oil in 75% yield.
1H-NMR (CDCl$_3$, 200 MHz): 7.95 (d, 2H); 7.68 (d, 2H); 7.55 (d, 2H); 7.0 (d, 2H); 4.12 (m, 2H); 3.86 (s, 3H); 3.67 (m, 4H); 3.6 (m, 4H); 3.42 (t, J=5.3 Hz, 4H); 2.56 (t, J=5.6 Hz, 2H); 2.42 (t, J=4.95 Hz, 4H); 1.44 (s, 9H).

Preparation of Compound (66)

DEAD (0.153 ml, 0.97 mmol) was added dropwise, at 0° C., to a solution of sulfonamide (65) (458.8 mg; 0.97 mmol), compound (6) of example 1 (300 mg, 0.97 mmol) and triphenylphosphine (255 mg; 0.97 mmol) in dry THF (16 ml).

The mixture was stirred at room temperature overnight then concentrated and purified by flash chromatography (hexane/ethyl acetate 1/5) to give compound (66) as an oil in 70% yield.
1H-NMR (CDCl$_3$, 200 MHz): 7.95 (d, J=8.6 Hz, 2H); 7.57 (m, 4H); 7.26 (s, 5H); 7.0 (d, J=8.8 Hz, 2H); 5.18 (m, 1H); 5.06 (s, 2H); 4.33 (m, 1H); 4.14 (m, 2H); 3.87 (s, 3H); 3.62 (m, 4H); 3.39 (m, 4H); 3.21 (m, 2H); 2.56 (t, J=5.4 Hz, 2H); 2.4 (m, 4H); 1.92 (m, 2H); 1.44 (s, 9H), 1.34 (s, 9H).

Preparation of Compound (1i)

To a solution of tert-Butyl ester (66) (800 mg, 0.966 mmol) in dry CH$_2$Cl$_2$ (12 ml), TFA (7.4 ml, 96.6 mmol) was added dropwise at 0° C. The reaction mixture was stirred at 0° C. for 1 h and then 4 h at room temperature. The solvent and TFA were removed in vacuo to give carboxylic acid (1i), as di-trifluoroacetate salt, as a white foam in 79% yield.
1H-NMR (CDCl$_3$, 200 MHz): 9.45 (bs, $^+$NH$_2$, $^+$NH); 8.0 (d, J=7.8 Hz, 2H); 7.68 (m, 4H); 7.4 (s, 5H); 7.1 (d, J=8.2 Hz, 2H); 5.6 (s, 1H); 5.13 (s, 2H); 4.27 (m, 3H); 3.97 (s, 3H); 3.78 (m, 10H); 3.44 (m, 4H); 1.98 (m, 2H).

Example 14

Preparation of Compound (1j)

To a solution of acid (1i) (150 mg, 0.167 mmol) in dry CH$_2$Cl$_2$ (4 ml) was added O-(tert-Butyldimethylsilyl)hydroxylamine (79 mg, 0.534 mmol) and EDCI (96 mg, 0.501 mmol). The reaction mixture was stirred at room temperature for 5 h then concentrated and the residue was dissolved in EtOAc and washed with water. The organic phase was dried (Na$_2$SO$_4$) and evaporated in vacuo. Thus obtained white solid (140 mg) was dissolved in dry CH$_2$Cl$_2$ (3 ml) and treated with TFA (0.8 ml). The reaction mixture was stirred at 0° C. for 1 h then allowed to reach room temperature and stirred for 4 h. The solution was concentrated to obtain a brown oil that was triturated with a mixture of CH$_2$Cl$_2$/Et$_2$O to give a brown solid hydroxamic acid (1j), as di-trifluoroacetate, in 50% yield.
1H-NMR (CDCl$_3$, 200 MHz): 7.86 (d, J=7.2 Hz, 2H); 7.56 (m, 4H); 7.24 (s, 5H); 6.94 (d, J=8.2 Hz, 2H); 5.73 (s, 1H); 5.1 (s, 2H); 4.1 (m, 4H); 3.82 (s, 3H); 3.53 (m, 8H); 3.25 (m, 4H); 2.05 (m, 2H).

Example 15

Preparation of Compound (1k)

To a solution of (1j) (40 mg, 0.04 mmol) in dry DMSO (1 ml) was added 2,5-dioxopyrrolidine-1-yl propionate (10 mg, 0.534 mmol) and TEA (10 drops, pH=8). The reaction mixture was stirred at room temperature for 24 h then were added 10 ml of Et$_2$O. The reaction was stopped and the solution cooled to −15° C. then left to reach 0° C. The ethyl ether layer was decanted and the residual yellow oil concentrated in vacuo. The pure compound (1k) was obtained after chromatography (CH$_2$Cl$_2$/MeOH) as a colorless oil in 24% yield.
1H-NMR (CDCl$_3$, 200 MHz): 7.88 (d, J=8.2 Hz, 2H); 7.6 (m, 4H); 7.26 (s, 5H); 6.96 (d, J=8.8 Hz, 2H); 5.09 (s, 2H);

4.34 (m, 3H); 3.87 (s, 3H); 3.62 (m, 6H); 3.45 (m, 4H); 2.59 (m, 2H); 2.46 (m, 4H); 2.28 (q, J=7.5 Hz, 2H); 1.68 (m, 2H); 1.11 (t, J=7.5 Hz, 3H).

Example 16

Preparation of a Compound of the Invention Comprising a Metalloproteases Inhibitor of Formula (I) Labelled with One Optical Imaging Moiety, Having the Following Formula (Compound 5 of Scheme 7)

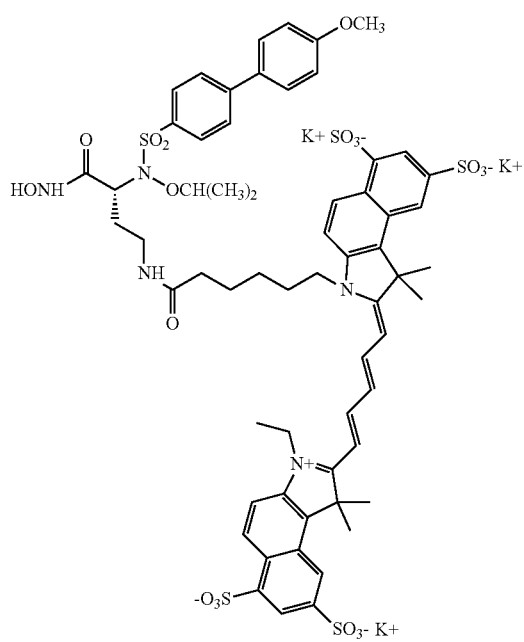

The title compound was prepared according to the following scheme:

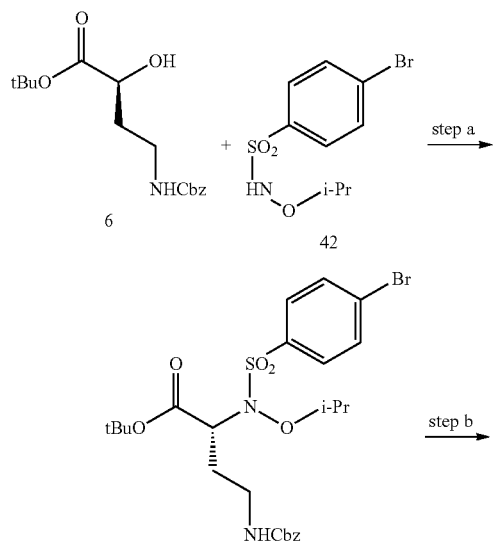

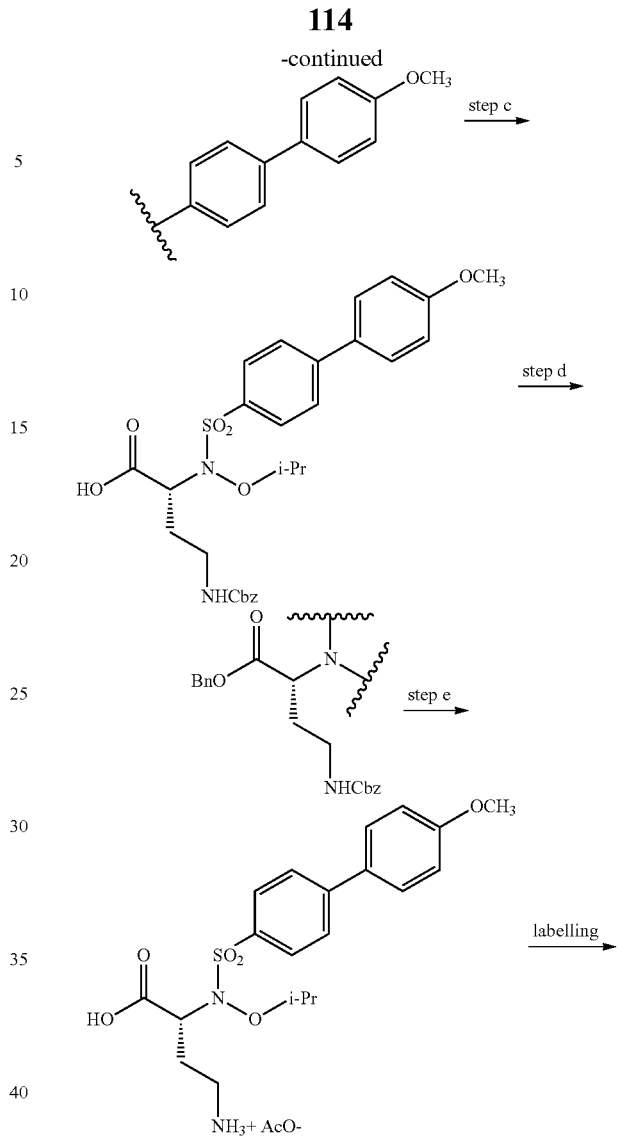

Step a

To a solution of sulfonamide 42 (2.29 g; 7.77 mmol) as prepared in example 11, alcohol 6 (1.85 g, 5.98 mmol) as prepared in example 1, triphenylphosphine (4.7 g; 17.9 mmol) in dry THF (77 ml), DIAD (2.9 ml, 14.9 mol) was added dropwise at 0° C.

The mixture was stirred at room temperature overnight then concentrated and purified by flash chromatography (hexane/ethyl acetate 8/3) to give the resulting compound of step (a) as a yellow oil in 67% yield.

1H-NMR (CDCl$_3$, 200 MHz): 7.7 (m, 4H); 7.35 (s, 5H); 5.09 (s, 2H); 4.39 (hept., J=6.2 Hz, 1H); 4.09 (m, 1H); 3.2 (m, 2H); 1.98 (m, 2H); 1.24 (s, 9H); 1.19 (ds, J=6.2 Hz, 6H).

Step b

A mixture of the compound of previous step (a) (700 mg, 1.96 mmol) and p-methoxyphenylboronic acid (309 mg, 2.03 mmol) was dissolved in dioxane/water (12/2.6 ml), then added with Tetrakis(triphenylphosphine)palladium(0) (69 mg, 0.06 mmol) and K$_3$PO$_4$ (584 mg, 2.75 mmol).

The reaction mixture was stirred at 80° C. for 30 minutes. The mixture was then cooled to room temperature and neutralized with NaHCO$_3$. The product was extracted with ethyl acetate and the organic phase was washed with brine, dried (Na$_2$SO$_4$) and concentrated in vacuo, then purified by flash chromatography (hexane/ethyl acetate) to obtain the compound of step (b) as an oil in 78% yield.

1H-NMR (CDCl$_3$, 200 MHz): 7.92 (d, J=8.2 Hz, 2H); 7.68 (d, J=8.2 Hz, 2H); 7.54 (d, J=8.4 Hz, 2H); 7.35 (s, 5H); 7.0 (d, J=8.4 Hz, 2H); 5.08 (s, 2H); 4.43 (hept., J=6 Hz, 1H); 4.1 (m, 1H); 3.87 (s, 3H); 3.23 (m, 2H); 1.98 (m, 2H); 1.24 (s, 9H), 1.2 (ds, J=6 Hz, 6H).

Step c

To a solution of the tert-Butyl ester of step (b) (380 mg, 0.64 mmol) in dry CH$_2$Cl$_2$ (6 ml), TFA (2.9 ml, 38 mmol) was added dropwise at 0° C. The reaction mixture was stirred at 0° C. for 1 h and 4 h at room temperature. After that, the solvent and TFA were removed to the corresponding acid as a solid in 84% yield.

1H-NMR (CDCl$_3$, 200 MHz): 7.9 (d, J=8.2 Hz, 2H); 7.67 (d, J=8.2 Hz, 2H); 7.56 (d, J=8.4 Hz, 2H); 7.33 (s, 5H); 6.98 (d, J=8.4 Hz, 2H); 5.06 (s, 2H); 4.42 (hept., J=6.4 Hz, 1H); 4.27 (m, 1H); 3.86 (s, 3H); 3.33 (m, 2H); 2.0 (m, 2H); 1.22 (ds, J=6.4 Hz, 6H).

Step d

To a solution of O-Benzylhydroxylamine HCl (142 mg, 0.89 mmol) in CH$_2$Cl$_2$ (16 ml) it was added N-methylmorpholine (0.1 ml, 0.9 mmol), then the acid of step (c) dissolved in CH$_2$Cl$_2$ (9 ml) and EDCI (170.6 mg, 0.89 mmol).

The reaction mixture was stirred at room temperature for 24 h, then diluted with CH$_2$Cl$_2$ and washed with brine, dried (Na$_2$SO$_4$) and concentrated. The crude product was purified by flash chromatography (hexane/ethyl acetate 1/1) to give the corresponding benzyloxy compound as an oil in 65% yield.

1H-NMR (CDCl$_3$, 200 MHz): 7.9 (d, J=8.2 Hz, 2H); 7.67 (d, J=8.2 Hz, 2H); 7.55 (d, J=8.4 Hz, 2H); 7.32 (s, 5H); 7.34 (s, 5H); 7.0 (d, J=8.4 Hz, 2H); 5.06 (s, 2H); 4.96 (m, 1H); 4.37 (hept., J=6.4 Hz, 1H); 3.88 (s, 3H); 3.12 (m, 2H); 2.02 (m, 2H); 1.23 (ds, J=6.4 Hz, 6H).

Step e

The compound of step (d) (70 mg, 0.106 mmol) was dissolved in a mixture of MeOH/CH$_3$COOH (1/1, 20 ml) and then Pd/C 10% (70 mg) was added therein. The resulting suspension was stirred under hydrogen atmosphere at room temperature. After 20 h the mixture was filtered through Celite and the filtrate was concentrated in vacuo to give the corresponding hydroxamic acid derivative as a white solid in 75% yield.

1H-NMR (CD$_3$OD, 200 MHz): 7.95 (d, J=8.2 Hz, 2H); 7.89 (d, J=8.2 Hz, 2H); 7.71 (d, J=7.9 Hz, 2H); 7.06 (d, J=7.9 Hz, 2H); 4.42 (m, 2H); 3.86 (s, 3H); 2.76 (m, 2H); 1.94 (s, 3H); 1.66 (m, 2H); 1.22 (ds, 6H).

Preparation of the Title Compound (5 of Scheme 7)

CyDye5.5 mono NHS ester (1 mg, 0.886 µmol) was dissolved in DMSO (500 µl) and added to a solution of the compound of step (e) (0.4 mg, 0.8 µmol) in DMSO (500 µl). One portion of triethylamine (25 µl) was then added to the reaction mixture. The reaction mixture was left under argon atmosphere and under stirring in the dark, at room temperature for 23 h, then it was added cold Et$_2$O (10 ml) and stirring was continued for 10 minutes. The formation of a blue precipitate was observed. The solution was frozen at −15° C., then left to reach room temperature, the solvents decanted and the precipitate was dried (under vacuum in the dark), to give the title compound as a blue solid in quantitative yields (1.19 mg).

C$_{61}$H$_{66}$N$_5$O$_{19}$S$_5$K$_3$ (MW=1450.82)

Example 17

Preparation of a Compound of the Invention Comprising a Metalloproteases Inhibitor of Formula (I) Labelled with One Optical Imaging Moiety, Having the Following Formula (Compound 6a of Scheme 9)

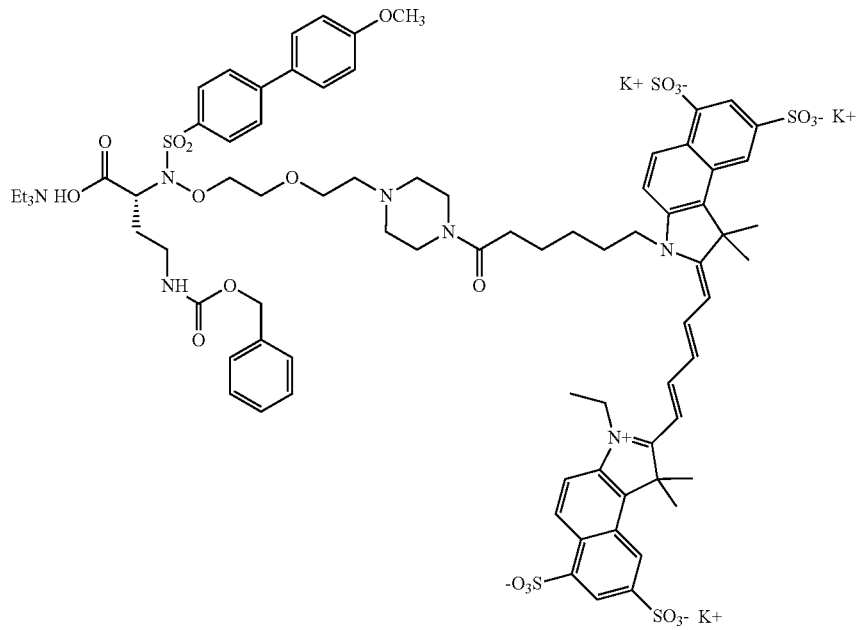

Preparation of the Title Compound (6a)

CyDye5.5 mono NHS ester (1 mg, 0.886 μmol) was dissolved in DMSO (400 μl) and added to a solution of the compound (1i) of example 13 (0.72 mg, 0.797 μmol) in DMSO (400 μl). One portion of triethylamine (50 μl) was then added to the reaction mixture. The reaction mixture was left under argon atmosphere and under stirring in the dark, at room temperature for 23 h, then it was added cold Et$_2$O (10 ml) and stirring was continued for 10 minutes. The formation of a blue precipitate was observed. The solution was frozen at −15° C., then left to reach room temperature, the solvents decanted and the precipitate was dried (under vacuum in the dark), to give the title compound as a blue solid in 80% yields (1.09 mg).

$C_{74}H_{80}N_6O_{21}S_5K_3$ (MW=1666.1)

Example 18

Preparation of a Compound of the Invention Comprising a Metalloproteases Inhibitor of Formula (I) Labelled with One Optical Imaging Moiety, Having the Following Formula (Compound 6b of Scheme 9)

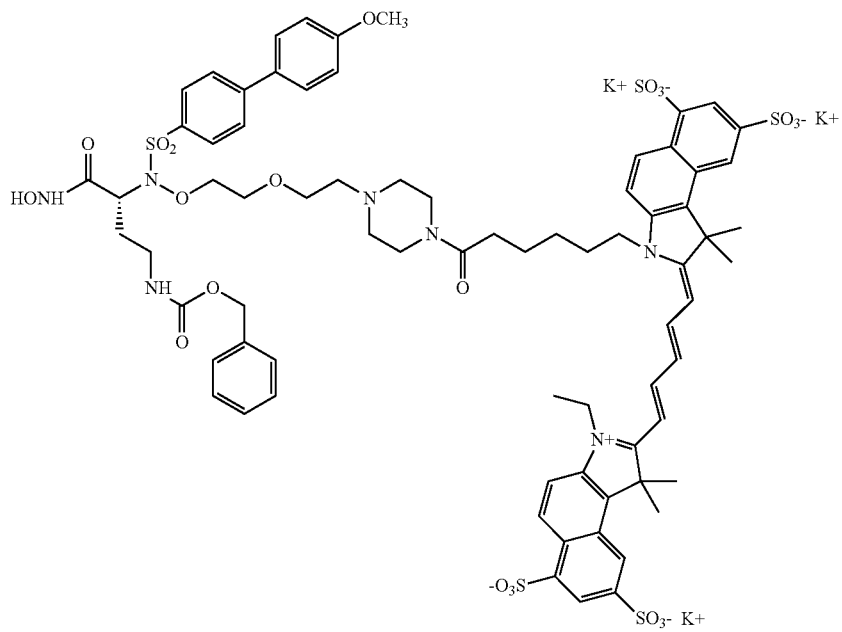

Preparation of the Title Compound (6b)

CyDye5.5 mono NHS ester (1 mg, 0.886 μmol) was dissolved in DMSO (400 μl) and added to a solution of the compound (1j) of example 14 (0.73 mg, 0.797 μmol) in DMSO (400 μl). One portion of triethylamine (50 μl) was then added to the reaction mixture. The reaction mixture was left under argon atmosphere and under stirring in the dark, at room temperature for 23 h, then it was added cold Et$_2$O (10 ml) and stirring was continued for 10 minutes. The formation of a blue precipitate was observed. The solution was frozen at −15° C., then left to reach room temperature, the solvents decanted and the precipitate was dried (under vacuum in the dark), to give the title compound as a blue solid in 80% yields (1.07 mg).

$C_{74}H_{82}N_7O_{22}S_5K_3$ (MW=1699.1)

Example 19

Preparation of a Compound of the Invention Comprising Two Residues of a Metalloproteases Inhibitor of Formula (I) Labelled with one Optical Imaging Moiety, Having the Following Formula (Compound 7 of Scheme 10)

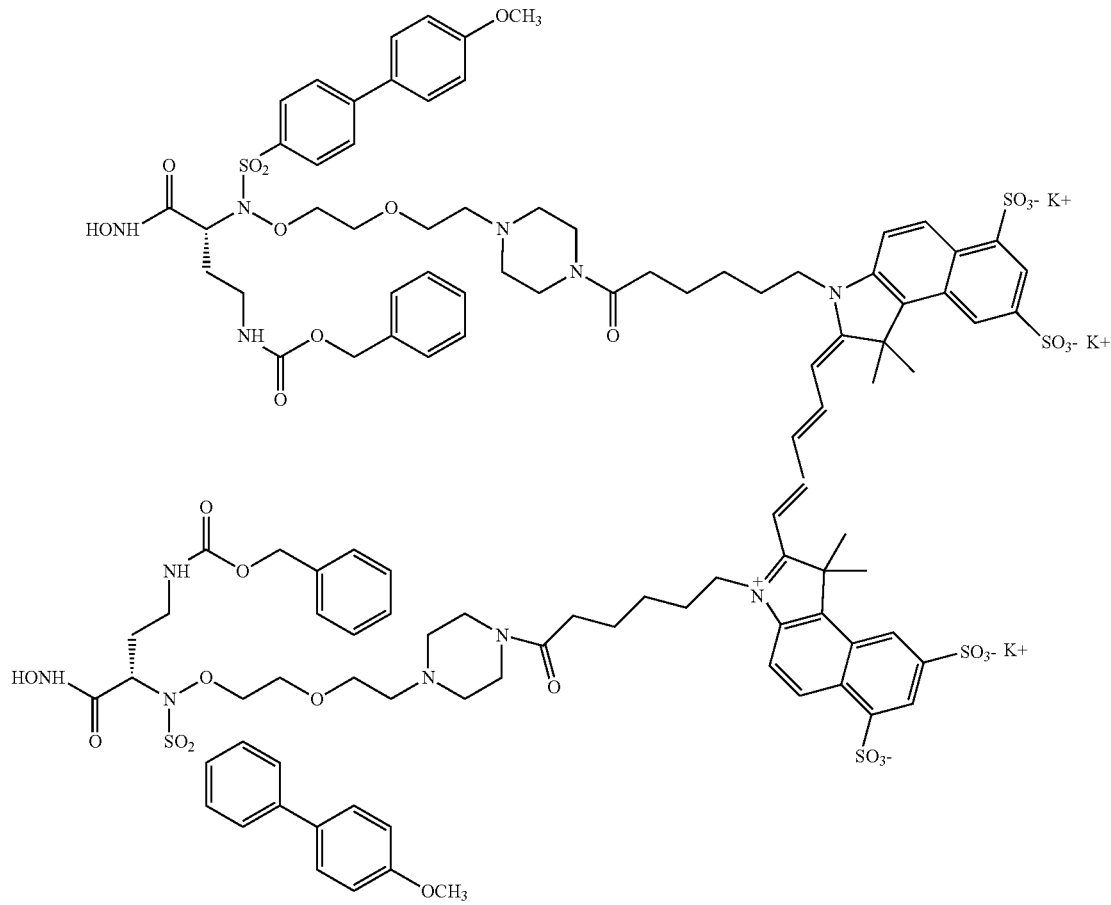

Preparation of the Title Compound (7)

CyDye5.5 bis NHS ester (5 mg, 3.81 µmol) was dissolved in DMSO (1 ml) and added to a solution of the compound (1j) of example 14 (6.27 mg, 6.86 pimp in DMSO (1 ml). One portion of triethylamine (0.5 ml) was then added to the reaction mixture. The reaction mixture was left under argon atmosphere and under stirring in the dark, at room temperature for 23 h, then it was added cold $Et_2O$ (10 ml) and stirring was continued for 10 minutes. The formation of a blue precipitate was observed. The solution was frozen at −15° C., then left to reach room temperature, the solvents decanted and the precipitate was dried (under vacuum in the dark), to give the title compound as a blue solid in 71% yields (6 mg).

$C_{111}H_{130}N_{12}O_{32}S_6K_3$ (MW=2454)

Example 20

Preparation of a Compound of the Invention Comprising a Metalloproteases Inhibitor of Formula (I) Labelled with One MRI Imaging Moiety, Having the Following Formula (Compound 8 of Scheme 11)

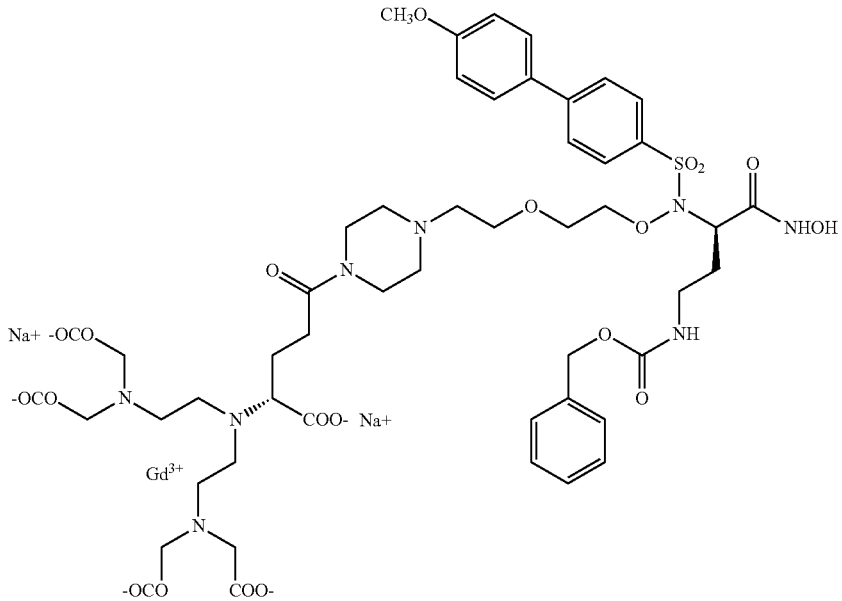

Preparation of Compound (21) of Scheme 11

To a solution of acid (20) of scheme 11 (0.039 mmol) and HBTU (0.048 mmol) in dry CH$_2$Cl$_2$ (0.5 ml) it was added dropwise a solution of compound (1j) of example 14 (0.022 mmol) and DIPEA (0.11 mmol) in dry CH$_2$Cl$_2$ (0.5 ml). The reaction mixture was stirred at room temperature for 18 h then, a further amount of CH$_2$Cl$_2$ (5 ml) was added. The solution was washed with saturated aqueous NaHCO$_3$ (2×5 ml) and then with 1M aqueous KHSO$_4$. The organic phase was separated, dried (Na$_2$SO$_4$) and concentrated to give a yellow oil. The crude product was purified by flash chromatography (9:1 DCM/MeOH) to obtain the compound (21) as a colorless oil in 17% yield (5.2 mg)

C$_{69}$H$_{106}$N$_8$O$_{20}$S (MW=1399.7)

Preparation of Compound (21a) of Scheme 11

A solution of compound (21) (0.0064 mmol) in TFA/DCM was stirred 5 h at room temperature. The mixture was evaporated and the residue purified by trituration with Et$_2$O to obtain a white solid in 84% yield.

C$_{50}$H$_{68}$N$_8$O$_{20}$S (MW=1133.18)

$^1$H-NMR ((CD$_3$)$_2$SO-d$_6$, 200 MHz): 8.1 (s, 1H); 7.89 (d, 4H); 7.72 (m, J=8.6 Hz, 2H); 7.34 (s, 5H); 7.06 (d, J=8.6 Hz, 2H); 5.00 (s, 2H); 3.82 (s, 3H); 3.6-3.05 (m, 22H); 2.9-2.66 (m, 14H); 2.46-1.90 (m, 4H).

Preparation of the Title Compound 8

By working according to known methods in the art, the compound (21a) of the previous step may be suitably converted into the corresponding Gd chelated complex.

Example 21

Preparation of Compounds as Per Scheme 1 BIS (ST228) Distilled water (3 ml) and 4-amino-(S)-2-hydroxybutyric acid (1 g, 8.4 mmol) and sodium hydroxide (672 mg, 16.8 mmol) were mixed and cooled down below 5° C. Then a solution of propionyl chloride (861 µl, 9.24 mmol) in 2 ml 1,4-dioxane was gently dropped to the cooled mixture. After 2 h at room temperature the reaction was stopped and concentrated in vacuo at 10° C., its pH was allowed to 1-2 or less by adding 1N aqueous HCl. The resulting mixture was concentrated. Purification by chromatography (Isolute® Si II (50 g), CH$_2$Cl$_2$/methanol 9/1) gave ST228 as an oil in 57% yield $^1$H-NMR (200 MHz, acetone-d$_6$) δ: 7.74 (m, 1H); 3.94 (m, 1H); 3.12 (m, 2H); 2.08 (q, J=7 Hz, 2H); 1.98-1.52 (m, 2H); 0.97 (t, J=7 Hz, 3H).

(EN222) Acetyl chloride (0.65 ml, 9.2 mmol) was added slowly at 0° C. to ST288 (700 mg, 4 mmol), the mixture allowed to rich room temperature and stirred 20 h. The crude product an orange oil obtained after concentration of the mixture was used in the next step without further purification (quantitative yield).

$^1$H-NMR (200 MHz, DMSO-d$_6$) δ: 7.86 (m, 1H); 4.78 (m, 1H); 3.11 (m, 2H); 2.08 (q, J=7 Hz, 2H); 1.95-1.50 (m, 2H); 1.90 (s, 3H); 0.97 (t, J=7 Hz, 3H).

(ST231) A solution of EN222 (840 mg, 3.87 mmol) in CH$_2$Cl$_2$ (20 ml) was added to a mixture of O-benzylhydroxylamine.HCl (740 mg, 4.64 mmol) and N-Methylmorpholin (510 µl, 4.64 mmol) in 10 ml CH$_2$Cl$_2$, then EDC (1.01 g, 5.42 mmol) was added. The mixture was stirred 24 h. Then dissolved with 20 ml of CH$_2$Cl$_2$, washed with brine, dried (Na$_2$SO$_4$) and concentrated. The crud product was purified by flash chromatography to obtain ST231 as an oil in 55% yield.

$^1$H-NMR (200 MHz, CDCl$_3$) δ: 9.68 (s, 1H); 7.37 (m, 5H); 6.98 (s, 1H); 4.99 (m, 1H); 4.91 (s, 2H); 3.43-3.12 (m, 2H); 2.15 (q, J=7 Hz, 2H); 2.06 (s, 3H); 2.03 (m, 2H); 1.11 (t, J=7 Hz, 3H).

(ST232) To a solution of ST231 (310 mg, 0.96 mmol) in 10 ml THF was added Ph$_3$P (1.05 g, 2.88 mmol), benzyl alcohol (100 μl, 0.96 mmol) and then dropwise at 0° C. DIAD (473 μl, 2.4 mmol).

The yellow solution was allowed to rich room temperature and stirred for 5 h. The concentration of the reaction solution furnished the crude product which was purified by flash chromatography to give compound ST232 as an colorless oil in 28%.

$^1$H-NMR (200 MHz, CDCl$_3$) δ: 7.34 (m, 5H); 7.30 (m, 5H); 5.62 (m, 1H); 5.33 (s, 2H); 5.19 (t, J=6.9 Hz, 1H); 5.00 (s, 2H); 3.31-3.02 (m, 2H); 2.05 (q, J=7 Hz, 2H); 1.94 (s, 3H); 1.91 (m, 2H); 1.08 (t, J=7 Hz, 3H).

(ST233): Could be obtained by treatment of ST232 with LiOH resulting in free hydroxyl functionality.

Example 22

Preparation of Compounds as Per Scheme 2 bis (ST154) Acetyl chloride (5 ml) was added slowly at 0° C. to S-(+)-α-hydroxy-1,3-dioxo-2-isoindoline butyric acid, 39, (365 mg, 1.46 mmol), the mixture allowed to rich room temperature and stirred 3 h. The crude product an oil obtained after concentration of the mixture was used in the next step without further purification (quantitative yield).

$^1$H-NMR (200 MHz, CDCl$_3$) δ: 7.88-7.70 (m, 4H); 5.02 (m, 1H); 3.86 (m, 2H); 2.40-2.15 (m, 2H); 2.12 (m, 3H)

(ST160) To a solution of ST154 (420 mg, 1.44 mmol) in CH$_2$Cl$_2$ (5 ml) was added a solution of O-benzylhydroxylamine.HCl (267 mg, 1.73 mmol) in CH$_2$Cl$_2$ (10 ml) and at 0° C. N-Methylmorpholin (200 μl, 1.73 mmol) in 10 ml CH$_2$Cl$_2$, then EDC (387 mg, 1.73 mmol) was added. The mixture was stirred 20 h. Then dissolved with 20 ml of CH$_2$Cl$_2$, washed with brine, dried (Na$_2$SO$_4$) and concentrated. The crud product was purified by flash chromatography to obtain ST160 as a solid in 54% yield.

$^1$H-NMR (200 MHz, CDCl$_3$) δ: 8.96 (s, 1H); 7.88-7.70 (m, 4H); 7.37 (m, 5H); 4.93 (s, 2H); 3.78 (m, 2H); 2.22 (m, 2H); 1.99 (s, 3H).

(ST220) To a solution of ST160 (100 mg, 0.25 mmol) in 4 ml THF was added Ph$_3$P (196 mg, 0.75 mmol), benzyl alcohol (26 μl, 0.25 mmol) and then dropwise at 0° C. DIAD (120 μl, 0.62 mmol).

The yellow solution was allowed to rich room temperature and stirred for 3 h. The concentration of the reaction solution furnished the crude product which was purified by flash chromatography to give compound EN220 as an oil in 34%.

$^1$H-NMR (200 MHz, CDCl$_3$) δ: 7.85-7.68 (m, 4H); 7.33 (m, 5H); 7.26 (m, 5H); 5.31 (m, 2H); 5.18 (m, 1H); 4.98 (s, 2H); 3.43 (m, 2H); 2.13 (m, 2H); 1.94 (s, 3H)

(EN220a): Could be obtained by treatment of EN220 with LiOH resulting in free hydroxyl functionality.

(EN221) To a solution of EN220 (40 mg, 0.08 mmol) in 10 ml MeOH was added Pd/C (12 mg), and Pd(OH)$_2$ (12 mg) and stirred at room temperature under H$_2$ atmosphere for 11 h. The reaction mixture was filtered and the filtrate concentrated. The product was obtained after a purification by chromatography (Isolute SiII, 5 g) in 52% yield as a white solid.

$^1$H-NMR (200 MHz, DMSO-d$_6$) δ: 10.697 (s, 1H); 8.83 (s, 1H); 7.88-7.83 (m, 4H);); 4.71 (m, 1H); 3.67 (m, 2H); 2.00 (m, 2H); 1.99 (s, 3H)

Example 23

Preparation of Compounds as Per Scheme 4 BIS

ST221) To a solution of 2-[2-(Fmocamino)ethoxy]ethanol (500 mg, 1.52 mmol) in THF (15 ml) was added Ph$_3$P (600 mg, 2.28 mmol), N-hydroxyphtalimide (250 mg, 1.52 mmol) and then at 0° C. DIAD (450 μl, 2.28 mmol). The reaction mixture was stirred at room temperature 5 h (TLC control n-hexane/ethylacetate 1:1). The solvent was evaporated to give an orange oil. The product was obtained in 57% yield as a white solid after a chromatographic purification (n-hexane/ethylacetate 1:1).

$^1$H-NMR (200 MHz, CDCl$_3$) δ: 7.74 (m, 7H); 7.33 (m, 5H); 5.69 (m, 1H); 4.39 (m, 2H); 4.36 (m, 2H); 4.24 (m, 1H); 3.81 (m, 2H); 3.62 (m, 2H); 3.40 (m, 2H).

ST222) ST222 (256 mg, 0.89 mmol) in 15 ml EtOH$_{(abs)}$ was treated with NH$_2$NH$_2$.H$_2$O (3.11 mmol) and the mixture stirred for 20 h at room temperature The white precipitate was filtered, the filtrate concentrated and dissolved in 15 ml of ethylacetate, then filtered again. Thus obtained filtrate was concentrated in vacuo to give the product as a colorless oil in 69% yield which was used in the next step without a further purification.

$^1$H-NMR (200 MHz, CDCl$_3$) δ: 7.49 (m, 8H); 6.07 (s, 2H); 4.42 (m, 1H); 4.10 (m, 1H); 3.84 (m, 2H); 3.64 (m, 4H); 3.49 (m, 2H); 2.87 (m, 2H).

ST224) To a solution of ST222 (210 mg, 0.61 mmol) in 3 ml THF was added N-Methylmorpholin (67 μl, 0.61 mmol) and then a solution of 4'-Methoxy[1,1'-biphenyl]-4-sulphonyl chloride 56 (192.3 mg, 0.68 mmol) in 3 ml THF. The reaction was left at room temperature for 24 h. Ethylacetate was added, the organic phase washed with water, then dried and concentrated. Thus obtained orange oil was subjected to flash column chromatography (n-hexane/ethylacetate 1:1). The product a white solid was obtained in 18% yield.

$^1$H-NMR (200 MHz, CDCl$_3$) δ: 7.97-7.92 (m, 2H); 7.83-7.78 (m, 2H); 7.72-7.67 (m, 2H); 7.61-7.46 (m, 6H); 7.35 (s, 1H); 7.00-6.95 (m, 4H); 5.11 (m, 1H); 4.10 (m, 1H); 4.13 (m, 2H); 3.86 (bs, 6H); 3.65 (m, 2H); 3.55 (m, 2H); 3.15 (m, 2H).

(A) Could be obtained from ST244 applying an method for Fmoc cleavage.*

(STAR8 and STAR 9) Could be obtained from compound A according to the procedure described for STAR6 and STAR7 respectively.

Example 24

Preparation of Compounds as Per Scheme 10 BIS (ST229) A solution of compound 10 (190 mg, 0.4 mmol) in 4 ml CH$_2$Cl$_2$ was treated at 0° C. with TFA (1.24 ml, 16.12 mmol). The reaction solution was stirred at 0° C. for an hour and then for 4 h at room temperature. The evaporation of the solvents gave a brown oil which was purified by chromatography (Isolute® Si II (5 g)). ST229 was obtained in 80% yield as an oil.

$^1$H-NMR (200 MHz, CDCl$_3$) δ: 7.96-7.92 (m, 2H); 7.70-7.66 (m, 2H); 7.56-7.52 (m, 2H); 7.00-6.96 (m, 2H); 4.08 (m, 2H); 3.85 (s, 3H); 3.68 (m, 4H); 3.33 (m, 8H); 3.00 (m, 2H).

$^{13}$C-NMR (200 MHz, CDCl$_3$) δ: 160.95; 146.89; 135.17; 129.73; 129.22; 127.69; 115.31; 76.12; 70.19; 67.20; 56.18; 50.54; 43.07; 31.73.

STAR 7: "reaction in the dark": To a solution of CyDye5.5 bis NHS ester (1 mg, 0.76 μmol) in DMSO (200 μl) was added a solution of compound ST229 (0.73 mg, 1.67 μmol) and Et₃N (10 μl) in DMSO (400 μl). The reaction mixture was left under argon atmosphere stirring in the dark at room temperature for 20 h, then added cold Et₂O (10 ml) and stirred for 10 min, formation of a blue precipitate was observed. The solution was frozen at −15° C. then left to rich RT, the solvents were decanted and the precipitate was dried. The HPLC analysis of blue precipitate (Colonna: Zorbax Eclipse XDB8 4.6×150 mm; (NH₄OAc 0.001% aqueous solution/CH₃CN) gradient of CH₃CN from 5% to 60% in 25 min, Flow=1.2 ml/min, UV 650 nm) indicated the product $T_R$=16.98 min (47%).

STAR6: "reaction in the dark": CyDye5.5 mono NHS ester (1 mg, 0.886 μmol) was dissolved in DMSO (500 μl) and added to a solution of compound ST229 (0.38 mg, 0.87 μmol) in DMSO (500 μl) then to the mixture was added in one portion Et₃N (25 μl). The reaction mixture was left under argon atmosphere stirring in the dark at RT for 23 h, then was added cold Et₂O (10 ml) and stirred for 10 min, formation of a blue precipitate was observed. The solution was frozen at −15° C. then left to rich RT, the solvents were decanted and the precipitate was dried in vacuo.

Example 25

Preparation of Compounds as Per Scheme 10 Tert

Compounds ST223 and ST224 are the building blocks for the synthesis of "piperazine free" inhibitor of MMPs and the corresponding CyDye 5.5 mono- and bis-labelled derivatives.

Structure of "piperazine free" CyDye5.5 mono- and bis-labelled MMPIs:

STAR8

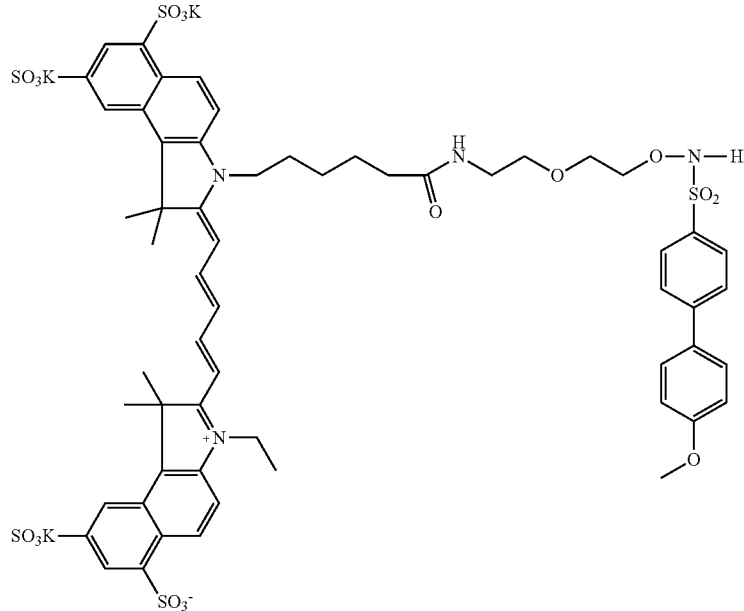

STAR9

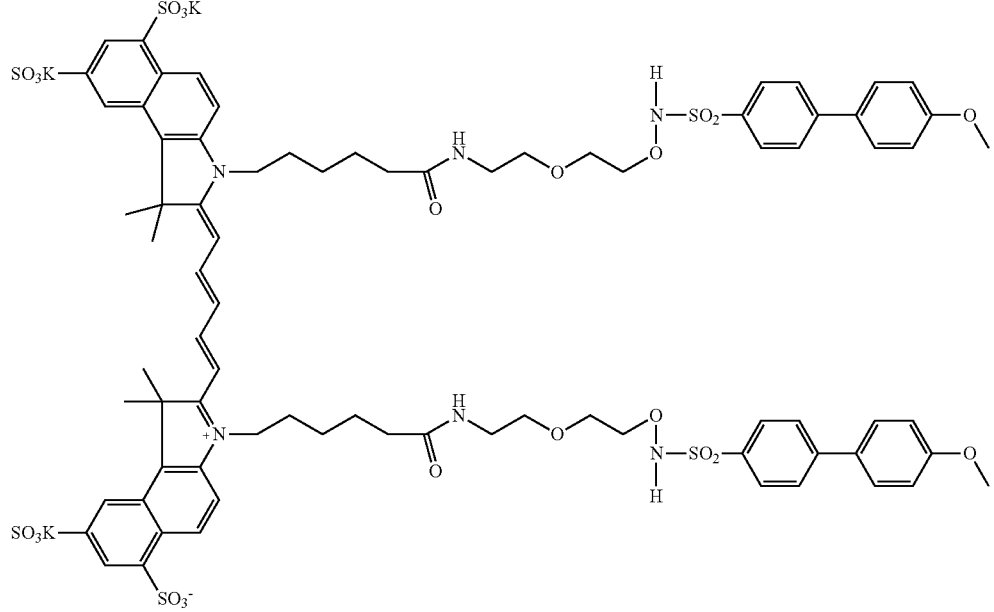

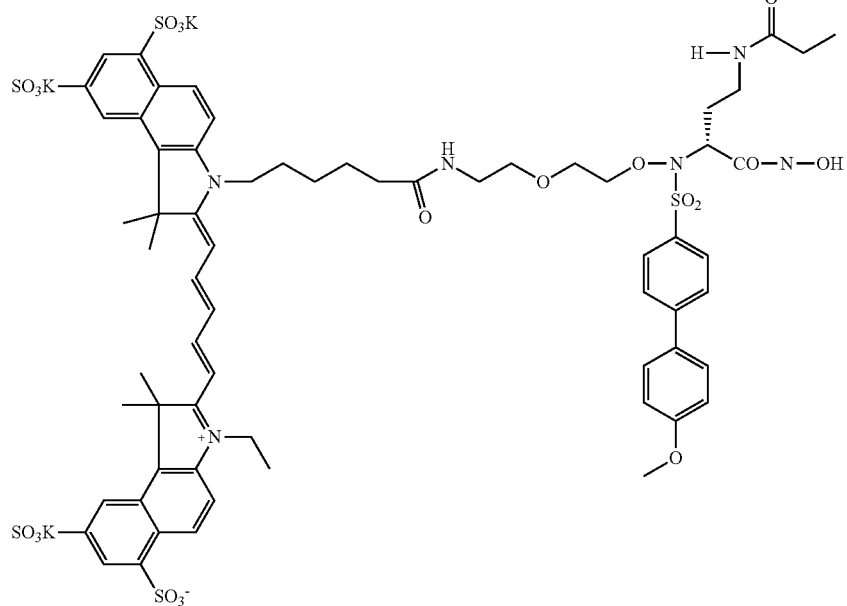
STAR10M
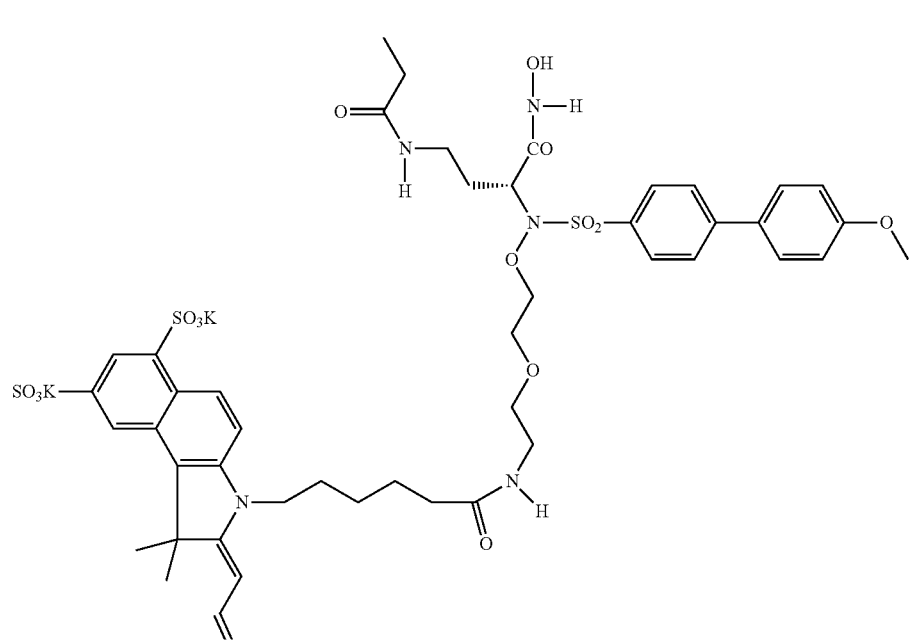
STAR10D

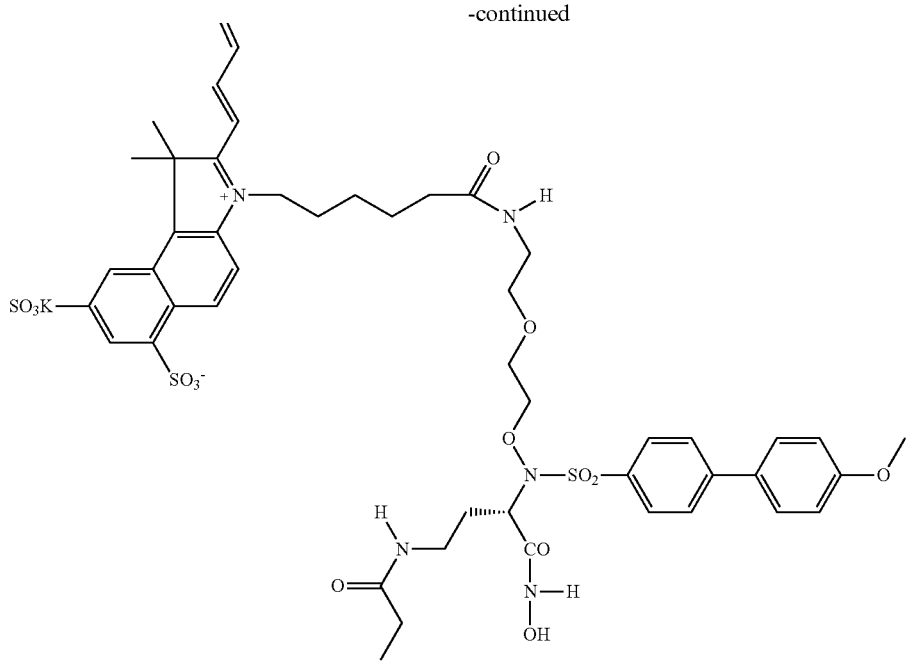

Example 26

MMP Inhibition Assays

Recombinant human progelatinase A (pro-MMP-2) and B (pro-MMP-9) from transfected mouse myeloma cells, MMP-16 and MMP-14 catalytic domains were supplied by Prof. Gillian Murphy (Department of Oncology, University of Cambridge, UK). Pro-MMP-1, pro-MMP-8, pro-MMP-3 and pro-MMP-13 were purchased from Calbiochem, MMP-12 was furnished from RDSystems.

Proenzymes were activated immediately prior to use with p-aminophenylmercuric acetate (APMA 2 mM for 1 h at 37° C. for MMP-2, MMP-1 and MMP-8, 1 mM for 1 h at 37° C. for MMP-9 and MMP-13). Pro-MMP-3 was activated with trypsin 5 µg/mL for 30 min at 37 C.° followed by soybean trypsin inhibitor (SBTI) 62 µg/mL.

For assay measurements, the inhibitor stock solutions (DMSO, 100 mM) were further diluted, at 7 different concentrations (0.01 nM-300 µM) for each MMP in the fluorimetric assay buffer (FAB: Tris 50 mM, pH=7.5, NaCl 150 mM, $CaCl_2$ 10 mM, Brij 35 0.05% and DMSO 1%). Activated enzyme (final concentration 2.9 nM for MMP-2, 2.7 nM for MMP-9, 1.5 nM for MMP-8, 0.3 nM for MMP-13, 5 nM for MMP-3, 1 nM for MMP-14cd, 15 nM for MMP-16cd and 2.0 nM for MMP-1, 1 nM for MMP12) and inhibitor solutions were incubated in the assay buffer for 4 h at 25° C. After the addition of 200 µM solution of the fluorogenic substrate Mca-Arg-Pro-Lys-Pro-Val-Glu-Nva-Trp-Arg-Lys(Dnp)-$NH_2$ (Sigma) for MMP-3 and Mca-Lys-Pro-Leu-Gly-Leu-Dap(Dnp)-Ala-Arg-$NH_2$ (Bachem) (Neumann, U.; Kubota, H.; Frei, K.; Ganu, V.; Leppert, D. *Anal. Biochem.* 2004, 328, 166) for all the other enzymes in DMSO (final concentration 2 µM), the hydrolysis was monitored every 15 sec. for 20 min. recording the increase in fluorescence ($\lambda_{ex}$=325 nm, $\lambda_{em}$=395 nm) using a Molecular Device SpectraMax Gemini XS plate reader. The assays were performed in triplicate in a total volume of 200 µl per well in 96-well microtitre plates (Corning, black, NBS). Control wells lack inhibitor. The MMP inhibition activity was expressed in relative fluorescent units (RFU). Percent of inhibition was calculated from control reactions without the inhibitor. $IC_{50}$ was determined using the formula: $V_i/V_o$=1/(1+[I]/$IC_{50}$), where $V_i$ is the initial velocity of substrate cleavage in the presence of the inhibitor at concentration [I] and $V_o$ is the initial velocity in the absence of the inhibitor. Results were analyzed using SoftMax Pro software and GraFit software.

TABLE 1

| Compound | $IC_{50}$ MMP-2 (nM) | $IC_{50}$ MMP-13 (nM) | $IC_{50}$ MMP-14 (nM) |
| --- | --- | --- | --- |
| Reference compound 1j of example 14 | 0.3 ± 0.03 | 0.2 ± 0.01 | 27 ± 1 |
| Compound 6b of example 18 | 0.6 ± 0.06 | 0.17 ± 0.02 | 67 ± 3.4 |
| Compound 6a of example 17 | 73.5 ± 5.7 | 50 ± 4.3 | — |
| Compound 5 of example 16 | 56 ± 8 | 82 ± 13 | — |
| Compound 7 of example 19 | 0.93 ± 0.1 | 0.69 ± 0.036 | 177 ± 10 |
| Compound 21a of example 20 | 0.2 ± 0.03 | 0.085 ± 0.0057 | 3.98 ± 0.6 |

As clearly indicated in the above table 1, some representative compounds of the invention (see compounds of examples 16 to 20) resulted to be endowed with a significant affinity against the tested enzymes.

Surprisingly, based on this highly sensible method for assessing the inhibitory activity against the tested enzymes, the compounds of the invention resulted to be endowed with an affinity against the tested enzymes at least comparable to that exerted by the parent compounds from which they derive, thus demonstrating that labelling according to the invention does not impair, at least to a significant extent, the affinity over the metalloproteases.

In addition, the representative compound 6b of the invention of example 18, being properly labelled with a fluorescent moiety, was tested against a panel of metalloproteases, in comparison to the parent compound of formula (I) from which it derives (compound 1j of example 14) and, also, in comparison to another structurally close compound of formula (I) bearing an acyl group (e.g. propionyl) in place of the fluorescent group (compound 1k of example 15). The formulae of these compounds are reported below:

Compound 6b of the Invention of Example 18:

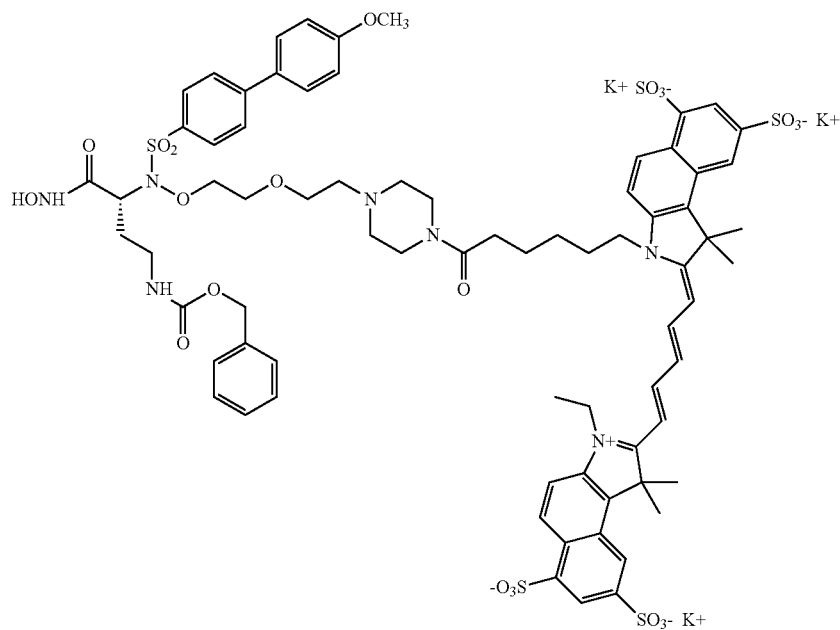

Reference Compound (1j) of Formula (I) of Example 14:

Reference Compound (1k) of Formula (I) of Example 15:

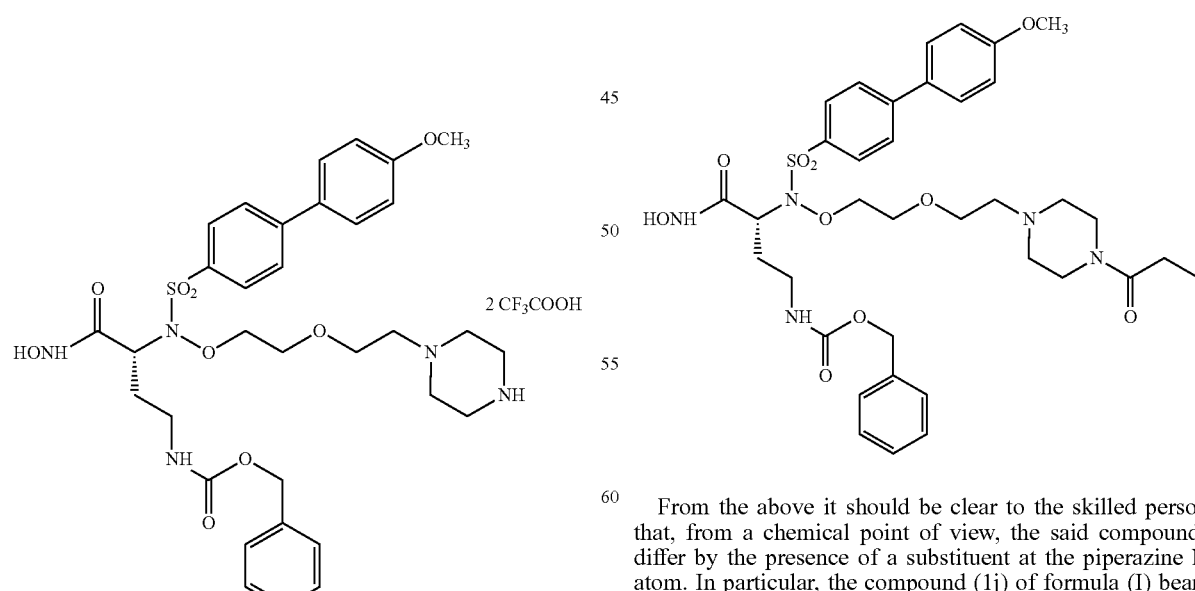

From the above it should be clear to the skilled person that, from a chemical point of view, the said compounds differ by the presence of a substituent at the piperazine N atom. In particular, the compound (1j) of formula (I) bears a H atom and is in the form of di-trifluoroacetate salt, the compound (1k) of formula (I) bears a propionyl group and, finally, the compound (6b) of the invention bears, in that same position, the bulky fluorescent substituent.

Affinity data for the said compounds against a panel of metalloproteases is reported in Table 2 below.

TABLE 2

| IC$_{50}$ (nM) | Compound of the invention of Ex. 18 | Reference Compound 1j | Reference Compound 1k |
|---|---|---|---|
| MMP-2 | 0.6 ± 0.06 | 0.3 ± 0.03 | 47.9 ± 4.9 |
| MMP-3 | 53 ± 4.5 | 39 ± 3.3 | 1990 ± 90 |
| MMP-8 | 6.5 ± 0.6 | 3.2 ± 0.2 | — |
| MMP-9 | 3.3 ± 0.1 | 1.7 ± 0.14 | 187 ± 11 |
| MMP-12 | 0.67 ± 0.06 | 0.4 ± 0.05 | 22 ± 4 |
| MMP-13 | 0.17 ± 0.02 | 0.2 ± 0.01 | 24.4 ± 2.5 |
| MMP-14 | 67 ± 3.4 | 27 ± 1 | 1698 ± 305 |
| MMP-16 | 30 ± 2.3 | 10 ± 1 | 1262 ± 59 |

Collected data for the representative compound of the invention over the parent compound (1j) of formula (I), towards the selected panel of metalloproteases, clearly demonstrate that labelling with an imaging moiety, in particular with the selected fluorescent moiety, does not impair its affinity to the metalloproteases.

The said advantageous effect is even more surprisingly by considering corresponding data for the other structurally close compound (1k) of formula (I).

In fact, whilst a comparison between compounds (1j) and (1k) demonstrates that the presence of a substituent, in particular of an acyl group like propionyl, appears to be responsible for a decreased affinity to the tested metalloproteases, though to a different extent, the presence of a bulky group in that same position, e.g. of the selected fluorescent moiety, unexpectedly provides for a significant increased affinity to the metalloproteases themselves.

Because all of the above, the instant compounds of the invention prove to be powerful tools for the diagnostic imaging of body organs, tissues, areas or districts wherein an overexpression of metalloproteases may occur.

In addition, when properly labelled with radiotherapeutic moieties, the compounds of the invention may be also used in therapy, for the treatment of those pathologies associated with the above over-expression.

The invention claimed is:

1. A compound comprising one or two residues of the metalloprotease inhibitor of formula (I), labelled with one optically active imaging moiety

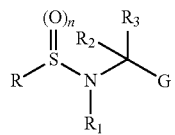
(I)

wherein:
 R is a group of formula —Ar—X—Ar' (II) wherein Ar is a phenylene group, X is a single bond or a divalent linker selected from the group consisting of —O—, —S— and —NH— and Ar' is a phenyl group; the said Ar and Ar' being optionally substituted by one or more groups selected from the group consisting of straight or branched C$_1$-C$_4$ alkyl, straight or branched C$_1$-C$_4$ alkoxy, and halogen atoms;

R$_1$ is —Ra or —ORa wherein Ra is a group of formula (III)

$$—(CH_2)_p—Z—(CH_2)_r—W \qquad (III)$$

wherein p is 1 or 2; Z is a divalent linker selected from —O— and —NH—; r is 1 or 2; and W is phenyl or a 5 or 6 membered heterocycle, each of which is optionally substituted by one or more groups selected from —NH$_2$, —COR', —COOR', —SO$_2$NHR' wherein R' is or a straight or branched C1 to C4 alkyl group;

one of R$_2$ and R$_3$ is H, and the other is a zinc binding group selected from —COOH and —CONHOH;

G is a group of formula —(CH$_2$)$_m$—N(R$_4$)(R$_5$);

R$_4$ is a group selected from —CORc, —COORc, and —S(O)$_2$Rc, wherein Rc is selected from aryl, straight or branched alkyl, and an arylalkyl group having from 1 to 4 carbon atoms in the alkyl chain;

R$_5$ is H;

n is 2;

m is 2;

or a pharmaceutically acceptable salt thereof and wherein:
 (i) the optically active imaging moiety is a fluorescent moiety selected from the group consisting of fluorescin, 5-carboxyfluorescein, indocyanine green, Cy5, Cy5.5 and derivatives thereof including Cy5.5 mono NH ester and Cy5.5 bis NHS ester;
 (ii) the one or two residues of the metalloprotease inhibitor of formula (I) and the optically active imaging moiety are directly conjugated to each other and the conjugation occurs between a carboxyl or amino function of the optically active imaging moiety and the amino or carboxyl function of the metalloprotease inhibitors of formula (I) so as to form carboxamido bonds.

2. The compound according to claim 1 wherein the metalloprotease inhibitor or inhibitors of formula (I) are selected from the group consisting of:

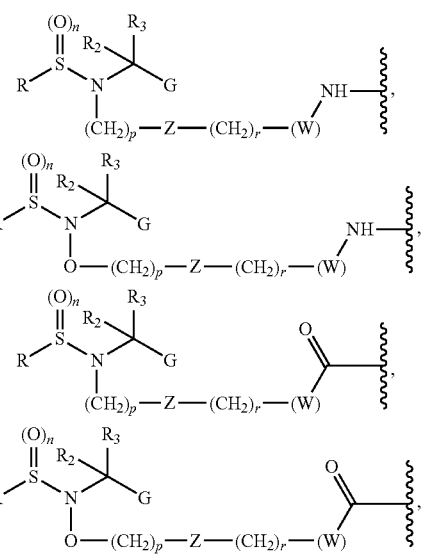

-continued

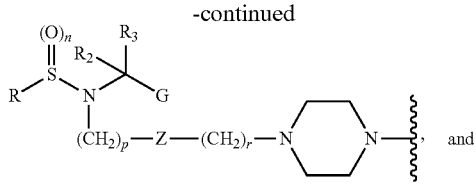

, and

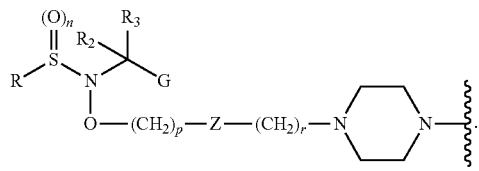

.

wherein R, n, $R_1$, $R_2$, $R_3$, m, G, p, Z, r and W are as defined in claim 1 and the ( ⁓⁓ ) represents the point of attachment with the rest of the molecule.

3. The compound according to claim 1 wherein $R_1$ is ORa.

4. A contrast agent for optical imaging agent comprising a compound according to claim 1.

5. A pharmaceutical composition comprising, as an active ingredient, an effective amount of an imaging agent, the agent comprising one or two residues of the metalloprotease inhibitors of formula (I) labelled with one optically active imaging moiety or the physiologically acceptable salts thereof, as defined in claim 1, together with pharmaceutically acceptable carriers, diluents or excipients.

6. A method for the in vivo detection and diagnosis of pathological conditions associated with an impaired expression of metalloproteases in a mammal, wherein the method comprises administering to said mammal an effective amount of a compound as defined in claim 1, and detecting and diagnosing said pathological conditions associated with impaired expression of metalloproteases in said mammal.

7. A method for the in vitro detection and measurement of an impaired expression of metalloproteases in a biological sample, wherein the method comprises contacting the said biological sample with an effective amount of a compound as defined in claim 1, and detecting and measuring said impaired expression of metalloproteases in said biological sample.

8. A compound according to claim 1 selected from the group consisting of:

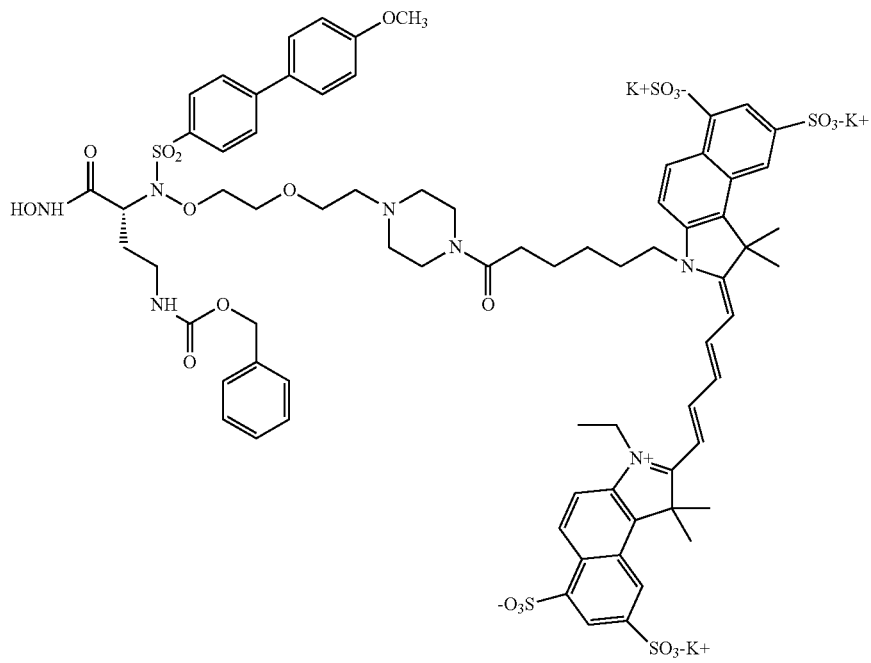

Compound 6b

Compound 6a
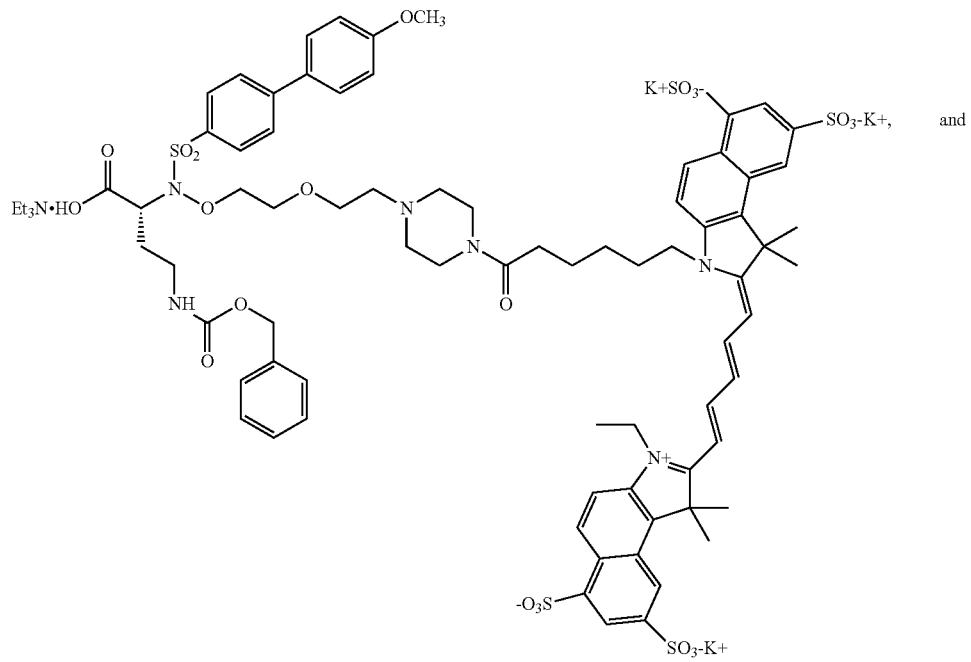
Compound 7
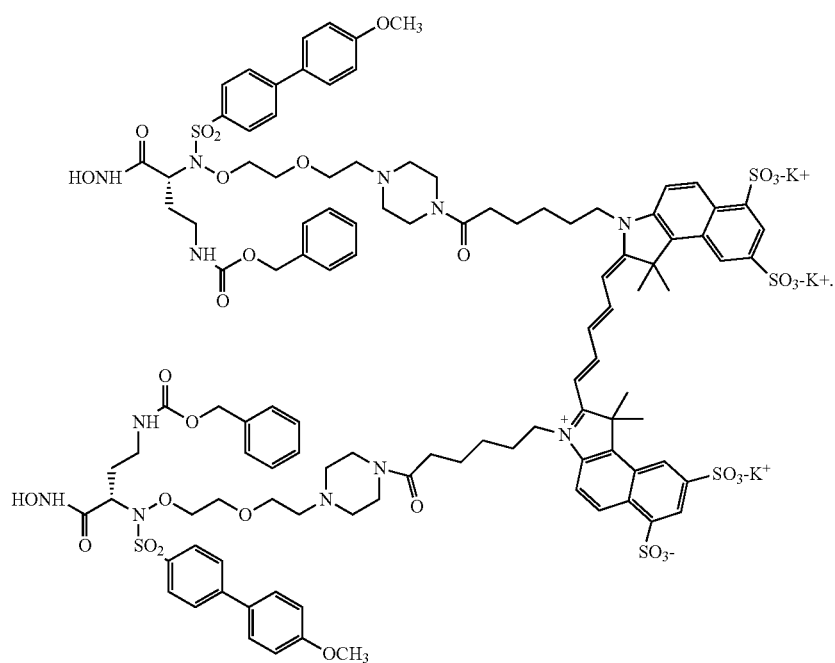

9. A compound selected from the group consisting of:
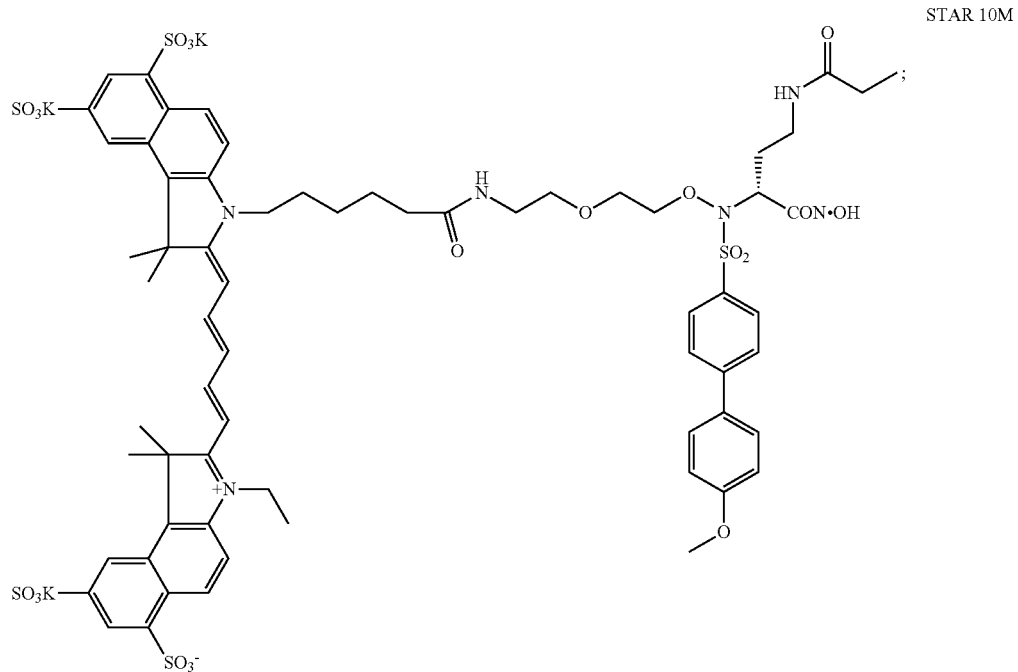
STAR 10M
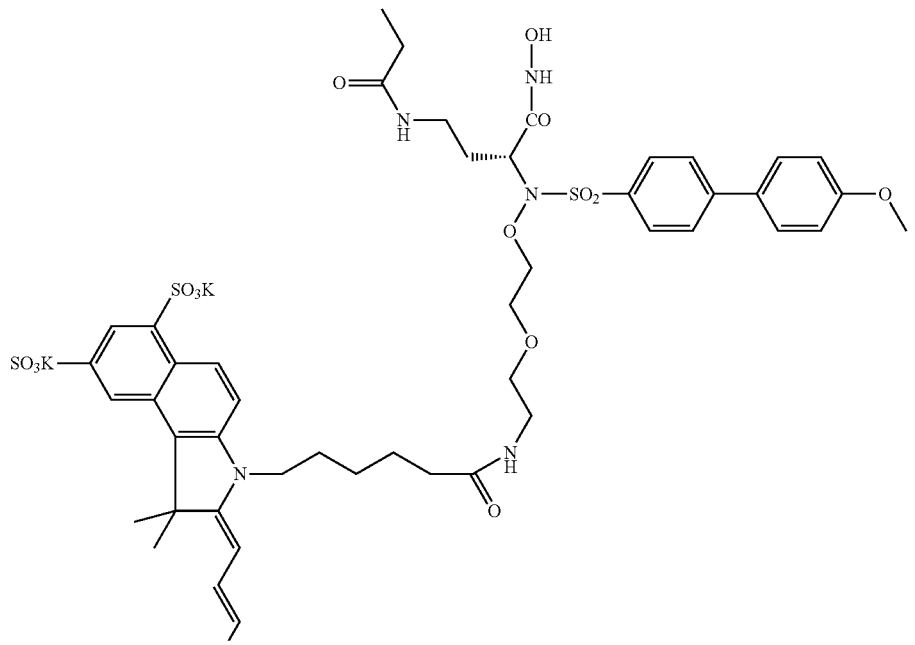
STAR10D -continued
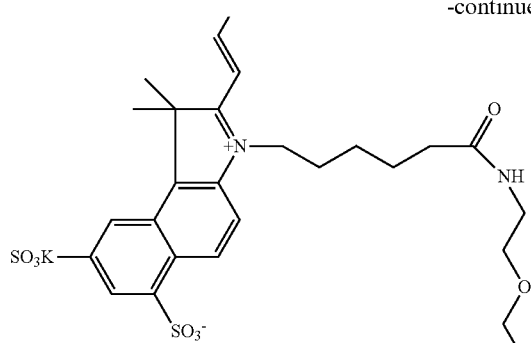
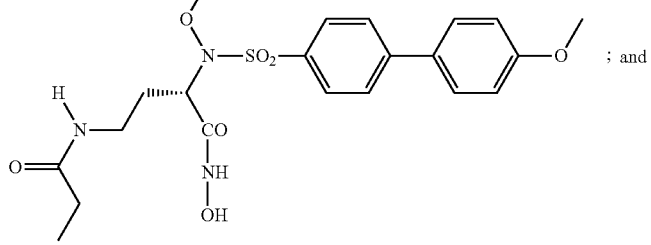
Compound 5
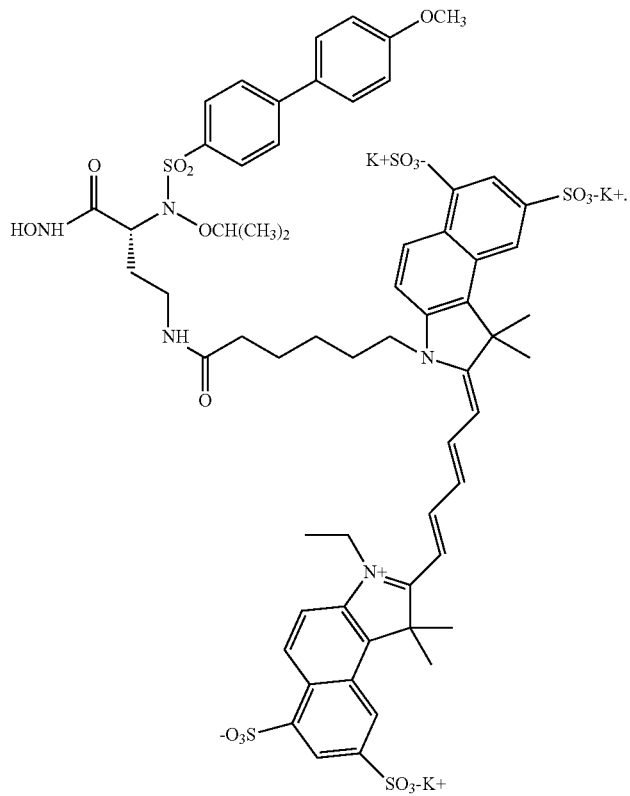
* * * * *